United States Patent
Grawunder et al.

(10) Patent No.: US 8,716,194 B2
(45) Date of Patent: May 6, 2014

(54) IDENTIFICATION OF ANTIGEN OR LIGAND-SPECIFIC BINDING PROTEINS

(75) Inventors: Ulf Grawunder, U.G. Hersberg (CH); Jorn Stitz, Basel (CH)

(73) Assignee: 4-Antibody AG, Basel (CH)

( * ) Notice: Subject to any disclaimer, the term of this patent is extended or adjusted under 35 U.S.C. 154(b) by 0 days.

(21) Appl. No.: 13/248,487

(22) Filed: Sep. 29, 2011

(65) Prior Publication Data
US 2012/0021491 A1  Jan. 26, 2012

Related U.S. Application Data

(62) Division of application No. 12/397,957, filed on Mar. 4, 2009.

(60) Provisional application No. 61/125,886, filed on Apr. 29, 2008.

(30) Foreign Application Priority Data

Mar. 5, 2008 (EP) .................................... 08004096

(51) Int. Cl.
    *C40B 40/08* (2006.01)
(52) U.S. Cl.
    USPC ............................................. 506/17
(58) Field of Classification Search
    None
    See application file for complete search history.

(56) References Cited

U.S. PATENT DOCUMENTS

| | | |
|---|---|---|
| 5,686,279 A | 11/1997 | Finer et al. |
| 5,780,225 A | 7/1998 | Wigler et al. |
| 5,834,256 A | 11/1998 | Finer et al. |
| 5,858,740 A | 1/1999 | Finer et al. |
| 5,876,961 A | 3/1999 | Crowe et al. |
| 6,051,427 A | 4/2000 | Finer et al. |
| 6,218,187 B1 | 4/2001 | Finer et al. |
| 6,291,158 B1 | 9/2001 | Winter et al. |
| 6,291,159 B1 | 9/2001 | Winter et al. |
| 6,291,160 B1 | 9/2001 | Lerner et al. |
| 6,291,161 B1 | 9/2001 | Lerner et al. |
| 6,319,707 B1 | 11/2001 | Adam et al. |
| 6,331,415 B1 | 12/2001 | Cabilly et al. |
| 6,479,243 B1 | 11/2002 | Wigler et al. |
| 6,506,604 B2 | 1/2003 | Finer et al. |
| 6,544,771 B1 | 4/2003 | Riviere et al. |

(Continued)

FOREIGN PATENT DOCUMENTS

| | | |
|---|---|---|
| EP | 0523949 B1 | 1/1993 |
| EP | 1041143 A2 | 10/2000 |

(Continued)

OTHER PUBLICATIONS

Harfst et al. (2005) Immunology Letters vol. 101 p. 173-184.

(Continued)

*Primary Examiner* — Christian Boesen
(74) *Attorney, Agent, or Firm* — Lathrop & Gage LLP; James H. Velema, Esq.; Andrew T. Wilkins, Esq.

(57) ABSTRACT

The present invention discloses novel methods for the generation, expression and screening of diverse collections of binding proteins such as antibodies or fragments thereof in vertebrate host cells in vitro, for the identification and isolation of ligand- or antigen-specific binding proteins. The methods disclosed herein allow the expression of diverse collections of binding proteins from at least one vector construct, which optionally can give rise to collections of diverse binding proteins upon transfer and expression into vertebrate host cells in situ.

14 Claims, 34 Drawing Sheets

(56) References Cited

U.S. PATENT DOCUMENTS

| | | | |
|---|---|---|---|
| 6,635,424 | B2 | 10/2003 | Wigler et al. |
| 6,680,192 | B1 | 1/2004 | Lerner et al. |
| 6,969,586 | B1 | 11/2005 | Lerner et al. |
| 7,189,841 | B2 | 3/2007 | Lerner et al. |
| 7,252,991 | B2 | 8/2007 | Finer et al. |
| 2002/0123057 | A1 | 9/2002 | Zauderer et al. |
| 2004/0038304 | A1 | 2/2004 | Bremel et al. |
| 2005/0196755 | A1 | 9/2005 | Zauderer et al. |
| 2006/0019395 | A1 | 1/2006 | Marasco |
| 2010/0009869 | A1 | 1/2010 | Bremel et al. |

FOREIGN PATENT DOCUMENTS

| | | |
|---|---|---|
| EP | 1340088 B1 | 9/2003 |
| EP | 1495146 B1 | 1/2005 |
| EP | 1830190 A2 | 9/2007 |
| WO | WO-89/12823 A1 | 12/1989 |
| WO | WO-90/13660 A2 | 11/1990 |
| WO | WO-92/01047 A1 | 2/1992 |
| WO | WO-92/02551 A1 | 2/1992 |
| WO | WO-95/01997 A1 | 1/1995 |
| WO | WO-98/24893 A2 | 6/1998 |
| WO | WO-02/066630 A1 | 8/2002 |
| WO | WO 02/102855 A2 | 12/2002 |
| WO | WO-03/017935 A2 | 3/2003 |
| WO | WO-03/054197 A2 | 7/2003 |
| WO | WO-03/068819 A1 | 8/2003 |
| WO | WO-03/083075 A2 | 10/2003 |
| WO | WO03/083077 A2 | 10/2003 |
| WO | WO-2004/051266 A1 | 6/2004 |
| WO | WO-2004/076677 A2 | 9/2004 |
| WO | WO-2004/106377 A1 | 12/2004 |
| WO | WO-2008/055795 A1 | 5/2008 |

OTHER PUBLICATIONS

Schier et al. (1996) Journal of Molecular Biology vol. 255 p. 28-43.
Alt, Frederick et al., "Organization and Reorganization of Immunoglobulin Genes in A-MuLV Transformed Cells: Rearrangement of Heavy but Not Light Chain Genes," Cell, vol. 27:381-390 (1981).
Bachl, Jürgen et al., "Hypermutation targets a green fluorescent protein-encoding transgene in the presence of immunoglobulin enhancers," Eur. J. Immunol., vol. 29:1383-1389 (1999).
Baker, Monya, "Upping the ante on antibodies," Nature Biotechnology, vol. 23(9): 1065-1072 (2005).
Bender, Eckhard et al., "Recombinant human antibodies: linkage of an Fab fragment from a combinatorial library to an Fc fragment for expression in mammalian cell culture," Hum. Antibod. Hybridomas, vol. 4:74-79 (1993).
Boder, Eric T. et al., "Directed evolution of antibody fragments with monovalent femtomolar antigen-binding affinity," PNAS, vol. 97(20):10701-10705 (2000).
Clackson, Tim et al., "Making antibody fragments using phage display libraries," Nature, vol. 352:624-628 (1991).
Clark, Mike, "Antibody humanization: a case of the 'Emperor's new clothes'?" Immunology Today, vol. 21(8):397-402 (2000).
Dunn, Ian S., "Assembly of Functional Bacteriophage Lambda Virions Incorporating C-Terminal Peptide or Protein Fusions with the Major Tail Protein," J. Mol. Biol., vol. 248:497-506 (1995).
Efimov, Vladimir P. et al., "Bacteriophage T4 as a Surface Display Vector," Virus Genes, vol. 10(2):173-177 (1995).
Gossen, Manfred et al., Tight control of gene expression in mammalian cells by tetracyclin-responsive promoters, Proc. Natl. Acad. Sci. USA, vol. 89:5547-5551 (1992).
Grawunder, Ulf et al., "Antigen receptor gene rearrangement," Current Opinion in Immunology, vol. 10:172-180 (1998).
Green, Larry L. et al., "Regulation of B Cell Development by Variable Gene Complexity in Mice Reconstituted with Human Immunoglobulin Yeast Artificial Chromosomes," J. Exp. Med., vol. 188(3):483-495 (1998).

Hanes, Jozef et al., "In vitro selection and evolution of functional proteins by using ribosome display," Proc. Natl. Acad. Sci. USA, vol. 94:4937-4942 (1997).
Hanes, Jozef et al., "Picomolar affinity antibodies from a fully synthetic naive library selected and evolved by ribosome display," Nature Biotechnology, vol. 18:1287-1292 (2000).
Hoogenboom, Hennie R. et al., "Natural and designer binding sites made by phage display technology," Immunology Today, vol. 21(8):371-378 (2000).
Kieke, Michele C. et al., "Isolation of anti-T cell receptor scFv mutants by yeast surface display," Protein Engineering, vol. 10(11):1303-1310 (1997).
Kieke, Michele C. et al., "Selection of function T cell receptor mutants from a yeast surface-display library," Proc. Natl. Acad. Sci. USA, vol. 96:5651-5656 (1999).
Köhler, G. et al., "Continuous cultures of fused cells secreting antibody of predefined specificity," Nature, vol. 256:495-497 (1975).
Kitamura, Toshio et al., "Efficient screening of retroviral cDNA expression libraries," Proc. Nati. Acad. Sci. USA, vol. 92:9146-9150 (1995).
Li, Min, "Applications of display technology in protein analysis," Nature Biotechnology, vol. 18:1251-1256 (2000).
Li, Yue-Sheng et al., The Regulated Expression of B Lineage Associated Genes during B Cell Differentiation in Bone Marrow and Fetal Liver, J. Exp. Med., vol. 178:951-960 (1993).
Lipovsek, Dasa et al., "In-vitro protein evolution by ribosome display and mRNA display," Journal of Immunological Methods, vol. 290:51-67 (2004).
Maruyama, Ichiro N. et al., "Xfoo: A X phage vector for the expression of foreign proteins," Proc. Natl. Acad. Sci. USA, vol. 91:8273-8277 (1994).
Maynard, Jennifer et al., "Antibody Engineering," Annu. Rev. Biomed. Eng., vol. 2:339-376 (2000).
Papavasiliou, F. Nina et al., "Somatic Hypermutation of Immunoglogulin Genes: Merging Mechanisms for Genetic Diversity," Cell, vol. 109:S35-S44 (2002).
Pear, Warren S. et al., "Efficient and Rapid Induction of a Chronic Myelogenous Leukemia-Like Myeloproliferative Disease in Mice Receiving P210 bcr/abl-Transduced Bone Marrow," Blood, vol. 92(10):3780-3792 (1998).
Ren, Z.J. et al., "Phage display of intact domains at high copy number: A system based on SOC, the small outer capsid protein of bacteriophage T4," Protein Science, vol. 5:1833-1843 (1996).
Rosenberg, Naomi et al., The Effect of Helper Virus on Abelson Virus-induced Transformation of Lymphoid Cells, J. Exp. Med., vol. 147:1126-1141 (1978).
Santini, Claudia et al., "Efficient Display of an HCV cDNA Expression Library as C-terminal Fusion to the Capsid Protein D of Bacteriophage Lambda," J. Mol. Biol., vol. 282:125-135 (1998).
Shimizu, Takeyuki et al., VpreBINpreB2/X5 Triple-Deficient Mice Show Impaired B Cell Development but Functional Allelic Exclusion of the IgH Locus, The Journal of Immunology, vol. 168:6286-6293 (2002).
Shinkai, Yoichi et al., "RAG-2-Deficient Mice Lack Mature Lymphocytes Owing to Inability to Initiate V(D)J Rearrangement," Cell, vol. 68:855-867 (1992).
Smith, George P., "Filamentous Fusion Phage: Novel Expression Vectors That Display Cloned Antigens on the Virion Surface," Science, vol. 228:1315-1317 (1985).
Sternberg, Nat et al., "Display of peptides and proteins on the surface of bacteriophage X.," Proc. Natl. Acad. Sci. USA, vol. 92:1609-1613 (1995).
Stitz, J. et al., "Screening of retroviral cDNA libraries for factors involved in protein phosphorylation in signaling cascades," Nucleic Acids Research, vol. 33(4):e39 (2005).
Traggiai, Elisabetta et al., "Development of a Human Adaptive Immune System in Cord Blood Cell-Transplanted Mice," Science, vol. 304:104-107 (2004).
Akamatsu, Yoshiko et al., "Essential Residues in V(D)J Recombination Signals," The Journal of Immunology, vol. 153:4520-4529 (1994).

(56) References Cited

OTHER PUBLICATIONS

Papavasiliou, Fotini et al., "Control of immunoglobulin gene rearrangements in developing B cells," Current Opinion in Immunology, vol. 9:233-238 (1997).

Shuh, Maureen et al., "V(D)J recombination of chromosomally integrated, wild-type deletional adn inversional substrates occur at similar frequencies with no preference for orientation," Immunology Letters, vol. 97:69-80 (2005).

Partial European Search Report for Application No. 09003076.8, dated Jul. 27, 2009.

International Search Report for Application No. PCT/EP2009/001525, dated Jul. 24, 2009.

Holt, Lucy J. et al., "Domain antibodies: proteins for therapy," Trends in Biotechnology, vol. 21(11):484-490 (2003).

Hoogenboom, Hennie R., "Selecting and screening recombinant antibody libraries," Nature Biotechnology, vol. 23 (9):1105-1116 (2005).

Little, M. et al., "Of mice and men: hybridoma and recombinant antibodies," Immunology Today, vol. 21(8):364-370 (2000).

European Office Action for Application No. 09003076.8, dated Apr. 7, 2010.

Wolkowicz, Roland et al., "Retroviral Technology—Applications for Expressed Peptide Libraries," Frontiers in Bioscience, vol. 8:d603-d619 (2003).

European Office Action for Application No. 09003076.8, dated Dec. 27, 2010.

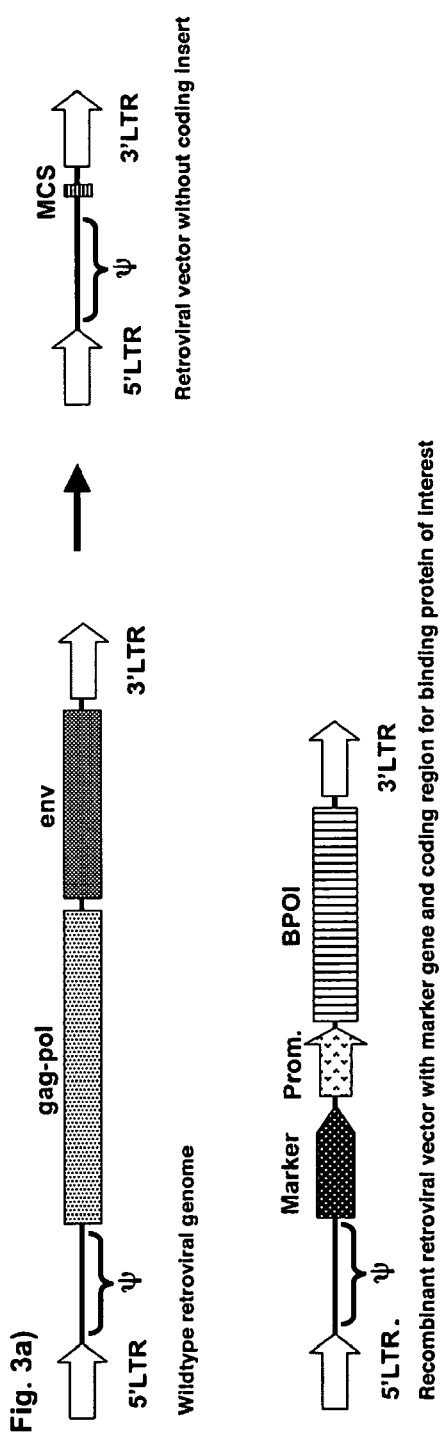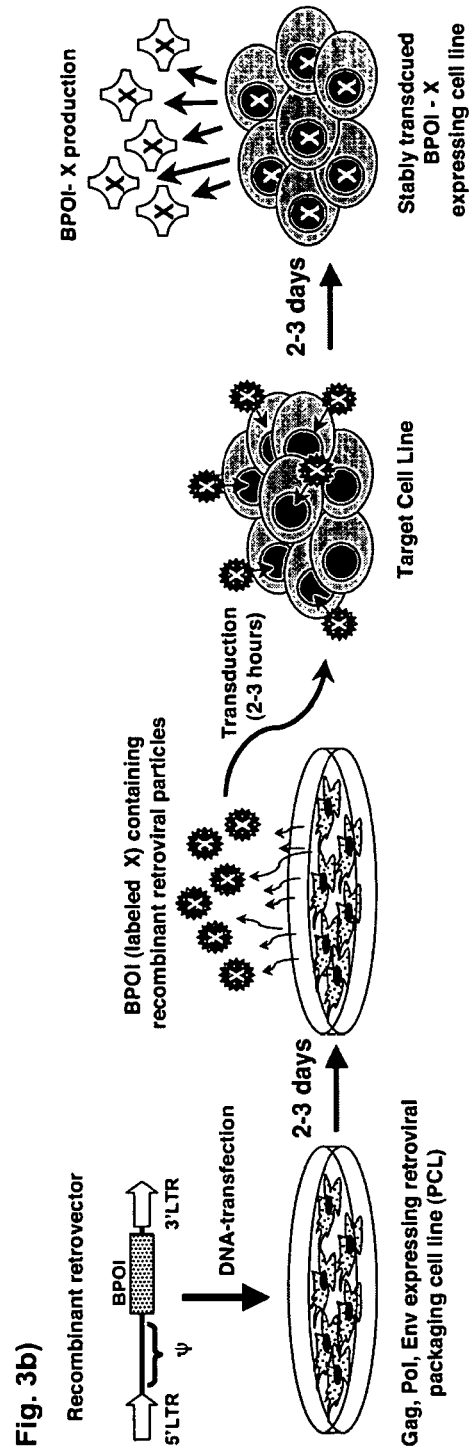
Fig. 3a)
Fig. 3b)

▶ and ◀ : 23 basepair recombination signal sequences (RSSs)   ▷ and ◁ : 12 basepair RSSs
LTR : long terminal repeat        ψ : packaging signal        v : stop codon

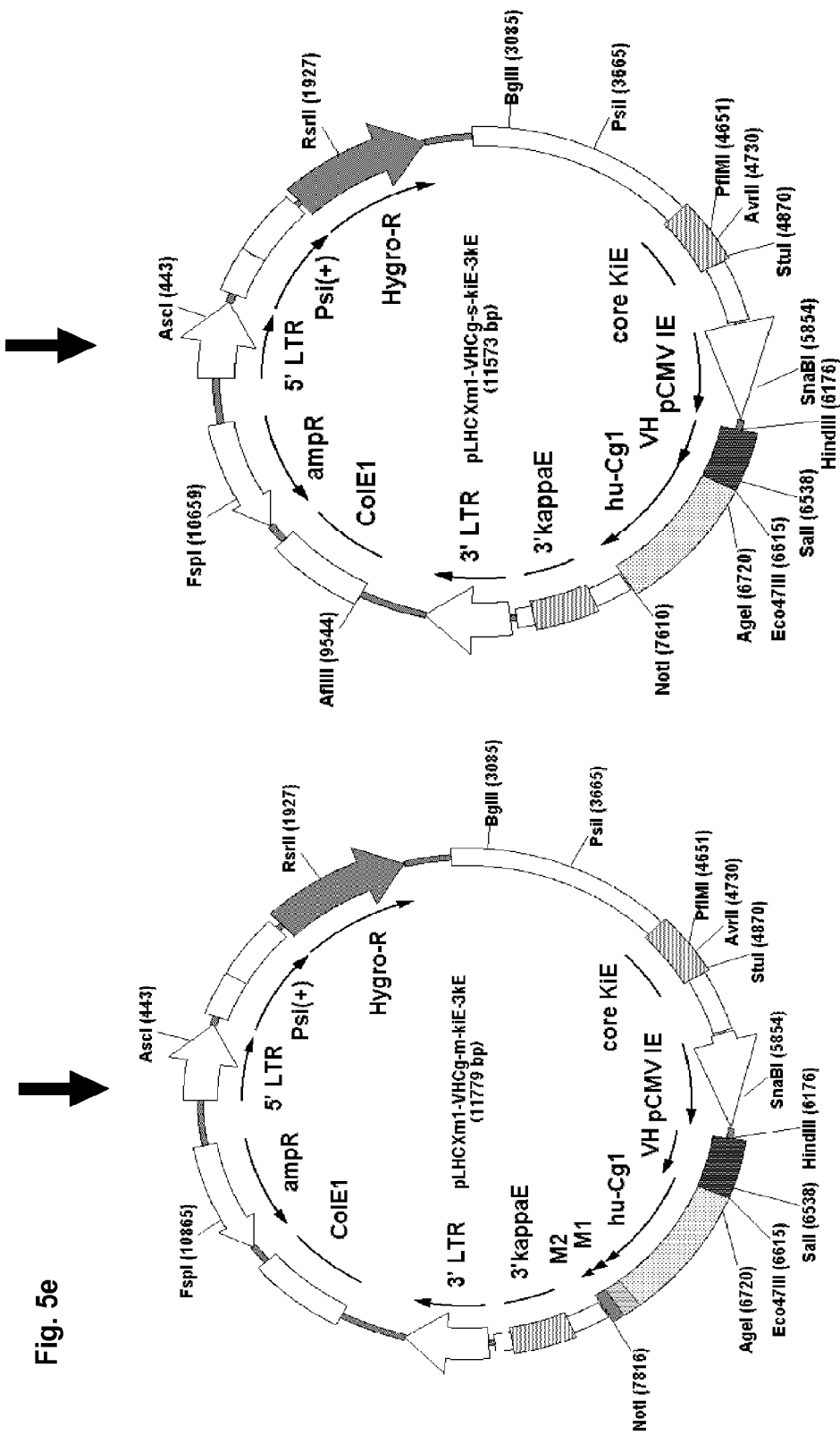

Fig. 6a
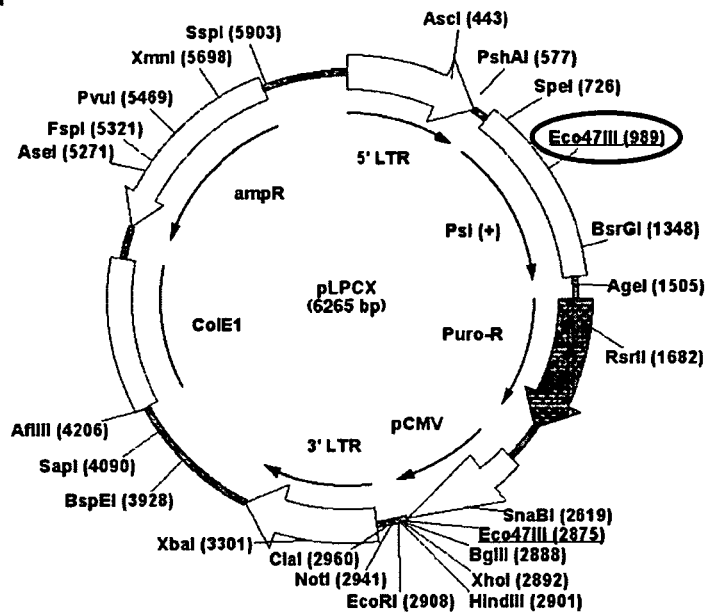
removal of Eco47III site by site-directed mutagenesis
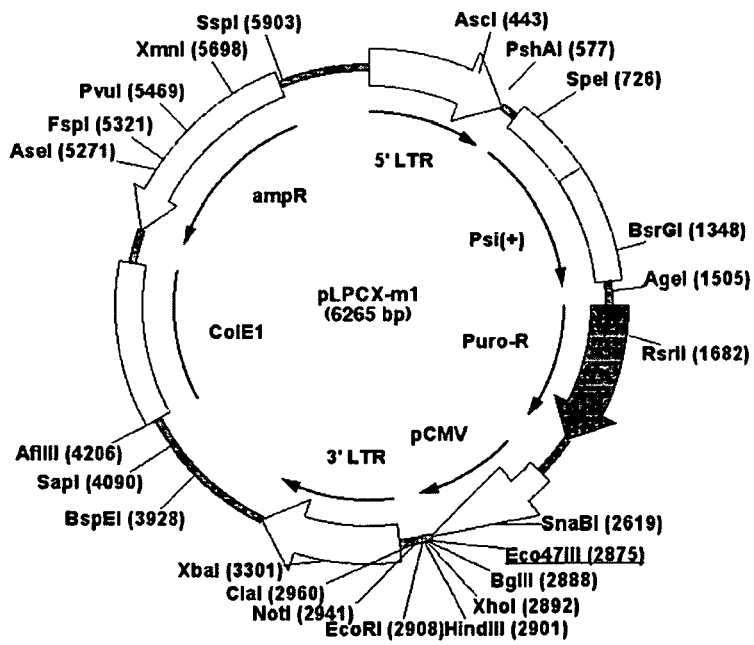

4.) Ligation of mutated EGFP ORF as HindIII/Eco47III fragments from pCR4-Topo EGFPmut into pLHCXm1-VHCγ-s and into pLHCXm1-VHCγ-s-κiE-3'κE

Fig. 10 a)

nt 313-> .. GGC AAC TAC AAG ACC CGC ...
aa 105->      G   N   Y   K   T   R
         wt EGFP sequence SpeI
                 ┌────────┐
nt.313-> .. GGC AAC TAg tat ACC CGC ...
aa 105->      G   N   •   Y   T   R
         mutated EGFP sequence b)
```
  1▶ ATGGTGAGCAAGGGCGAGGAGCTGTTCACCGGGGTGGTGCCCATCCTGGTCGAGCTGGACGGCGATGTAAACGGCCACAAGTTCAGCGTGTCCGGCGAGG
     TACCACTCGTTCCCGCTCCTCGACAAGTGGCCCACCACTCGGGACCTGACCTGCCGCTGCCACCTCCATTTGCCGGTGTTCAAGTCGCACAGGCCGCTCC
  1▶  M  V  S  K  G  E  E  L  F  T  G  V  V  P  I  L  V  E  L  D  G  D  V  N  G  H  K  F  S  V  S  G  E
101▶ GCGAGGGCGATGCCACCTACGGCAAGCTGACCCTGAAGTTCATCTGCACCACCGGCAAGCTGCCCGTGCCCTGGCCCACCCTCGTGACCACCCTGACCTA
     CGCTCCCGCTACGGTGGATGCCGTTCGACTGGGACTTCAAGTAGACGTGGTGGCCGTTCGACGGGCACGGGACCGGGTGGGAGCACTGGTGGGACTGGAT
 34▶  G  E  G  D  A  T  Y  G  K  L  T  L  K  F  I  C  T  T  G  K  L  P  V  P  W  P  T  L  V  T  T  L  T  Y
201▶ CGGCGTGCAGTGCTTCAGCCGCTACCCCGACCATATGAAGCAGCACGACTTCTTCAAGTCCGCCATGCCCGAGGGCTACGTCCAGGAGCGCACCATCTTC
     GCCGCACGTCACGAAGTCGGCGATGGGGCTGGTATACTTCGTCGTGCTGAAGAAGTTCAGGCGGTACGGGCTCCCGATGCAGGTCCTCGCGTGGTAGAAG
 67▶  G  V  Q  C  F  S  R  Y  P  D  H  M  K  Q  H  D  F  F  K  S  A  M  P  E  G  Y  V  Q  E  R  T  I  F
                                 SpeI (316)
301▶ TTCAAGGACGACGGCAACTAgtatACCCCCGCGGTGAGTTCAAGGGCACACCCTGGTGAACCGCATCGAGCTGAAGGGCATCGACTTCAAGGAG
     AAGTTCCTGCTGCCGTTGATcataTGGGGCGCGGCCCACTCAAGTTCCCGTGTGGGACCACTTGGCGTAGCTCGACTTCCCGTAGCTGAAGTTCCTC
101▶  F  K  D  D  G  N  •  Y  T  R  A  E  V  K  F  E  G  D  T  L  V  N  R  I  E  L  K  G  I  D  F  K  E
401▶ GACGGCAACATCCTGGGGCACAAGCTGGAGTACAACTACAACAGCCACAACGTCTATATCATGGCCGACAAGCAGAAGAACGGCATCAAGGTGAACTTCA
     CTGCCGTTGTAGGACCCCGTGTTCGACCTCATGTTGATGTTGTCGGTGTTGCAGATATAGTACCGGCTGTTCGTCTTCTTGCCGTAGTTCCACTTGAAGT
134▶  D  G  N  I  L  G  H  K  L  E  Y  N  Y  N  S  H  N  V  Y  I  M  A  D  K  Q  K  N  G  I  K  V  N  F
501▶ AGATCCGCCACAACATCGAGGACGGCAGCGTGCAGCTCGCCGACCACTACCAGCAGAACACCCCCATCGGCGACGGCCCCGTGCTGCTGCCCGACAACCA
     TCTAGGCGGTGTTGTAGCTCCTGCCGTCGCACGTCGAGCGGCTGGTGATGGTCGTCTTGTGGGGGTAGCCGCTGCCGGGGCACGACGACGGGCTGTTGGT
167▶  K  I  R  H  N  I  E  D  G  S  V  Q  L  A  D  H  Y  Q  Q  N  T  P  I  G  D  G  P  V  L  L  P  D  N  H
601▶ CTACCTGAGCTACCAGTCCGCCCTGAGCAAAGACCCCAACGAGAAGCGCGATCACATGGTCCTGCTGGAGTTCGTGACCGCCGCCGGGATCACTCTCGGC
     GATGGACTCGATGGTCAGGCGGGACTCGTTTCTGGGGTTGCTCTTCGCGCTAGTGTACCAGGACGACCTCAAGCACTGGCGGCGGCCCTAGTGAGAGCCG
200▶  Y  L  S  T  Q  S  A  L  S  K  D  P  N  E  K  R  D  H  M  V  L  L  E  F  V  T  A  A  G  I  T  L  G
701▶ ATGGACGAGCTGTACAAG
     TACCTGCTCGACATGTTC
234▶  M  D  E  L  Y  K
```

IDENTIFICATION OF ANTIGEN OR LIGAND-SPECIFIC BINDING PROTEINS

The present application is a divisional application of U.S. patent application Ser. No. 12/397,957 filed Mar. 4, 2009, which claims priority to U.S. Provisional Patent Application No. 61/125,886 file Apr. 29, 2008 and European Patent Application No. 08004096.7 filed Mar. 5, 2008. The entire contents of each of the above documents are incorporated herein by reference.

FIELD OF THE INVENTION

The present invention discloses novel methods for the generation, expression and screening of diverse collections of binding proteins in vertebrate cells in vitro, allowing the identification and isolation of ligand- or antigen-reactive binding proteins. In particular, the present invention relates to methods for the retroviral expression, isolation and identification of at least one nucleotide sequence encoding a binding protein such as an antibody or fragment thereof specific for a desired antigen or ligand.

BACKGROUND

Display technologies have played an important role in the isolation of specific high-affinity binding proteins for diagnostic and therapeutic applications in a vast number of disorders and diseases. These technologies extend into the broad field of antibody engineering, synthetic enzymes, proteomics, and cell-free protein synthesis. Biomolecular display technologies, which allow the construction of a large pool of modularly coded biomolecules, their display for property selection, and rapid characterisation (decoding) of their structures, are particularly useful for accessing and analyzing protein diversity on a large scale. Recently, in vitro display technologies have come to prominence due to the isolation of antibodies by phage display, ribosome display and microbial display, which have now become mainstream antibody and protein engineering platforms. However, microbial expression and display systems suffer from limitations in particular for the expression of large, dimeric vertebrate proteins, like antibodies. This is due to the general inability to express full-length antibodies in such expression systems, which requires the display of engineered antibody fragments, but also due to the lack of glycosylation, absence of chaperone proteins, lack of subcellular compartments and eukaryotic cell specific protein trafficking, that individually and collectively result in protein folding artefacts in microbially expressed mammalian proteins. Recently, in vitro display methods have also been developed employing eukaryotic host cells, including yeast, plants and mammalian cells. Yeast and plant cell expression systems also suffer from a lack of glycosylation and specific vertebrate and mammalian cell-specific chaperones, so that the same limitations with regard to protein folding apply for the expression of vertebrate proteins in such systems. Expression, proper protein folding and posttranslational modification of large recombinant proteins, like antibodies, can only be expected to occur with reasonable efficiency and quality in vertebrate expression systems, ideally expressing proteins in the phylogenetically most closely related cell system.

Therefore, therapeutically interesting proteins, like antibodies from rodents or humans, are ideally expressed in rodent or human cells, and it is not surprising that only expression systems from such species are approved by regulatory authorities for the production of clinically-grade full-length therapeutic antibodies. However, vertebrate and mammalian cell based expression systems are laborious, require long-time frames to establish stably producing cell lines and clones, and an efficient and controlled genetic modification of such cells is often not trivial and therefore makes these systems less attractive for screening and display methods. For instance, DNA transfection methods cannot be controlled for the number of DNA constructs that are either transiently or stably incorporated into transfected cells, which precludes clonal expression of protein libraries and therefore a clean gene to phenotype screen. The alternative viral systems either lack a proper control of clonal expression, a stable maintenance of the genetic constructs, and/or suffer from the fact that such systems often cause cytopathic effects in the target cells (e.g. vaccinia virus expression), such that protein clones either cannot be displayed and/or sequentially enriched for a particular phenotype, like e.g. specific binding to an antigen.

It is thus an object of the present invention to provide a method that clearly overcomes all of the above-mentioned limitations and drawbacks of prior art prokaryotic and eukaryotic gene expression and selection systems. The method according to the invention utilises stable retroviral expression of binding proteins such as, in particular, antibodies in mammalian cells, in particular B lymphocytic cell lines, such that stable and preferably clonal expression of antibody proteins is achieved in the presence of proper glycosylation, chaperone proteins and protein trafficking, ensuring proper protein folding and allowing efficient and, if desired, repeated screening for antigen-binding antibody clones. Since the preferred embodiment of the method according to the invention is based on the retroviral expression of antibodies or fragments thereof in precursor lymphocytes the technology disclosed herein is termed 'Retrocyte Display' (for retroviral preB lymphocyte display).

SUMMARY OF THE INVENTION

The present invention generally relates to the provision of therapeutic or diagnostic antibodies or fragments thereof. In particular, it relates to the identification and selection of antigen-reactive antibodies with fully human amino acid sequences that are of interest for therapeutic applications. The embodiments of the invention involve retroviral expression vectors enabling the expression of diverse collections of binding proteins, including antibodies or fragments thereof, in vertebrate, preferably mammalian, cells and methods for the efficient isolation of ligand- or antigen-reactive molecules. The present invention provides novel methods for the generation of diverse collections of binding proteins, such as antibodies or fragments thereof, by three alternative methods. First, by chain shuffling of at least one heavy or light chain molecule against a diverse collection (library) of light or heavy chains, (chain-shuffling approach), or second, by diversification of at least one combination of an antibody heavy and light chain after retroviral transduction into vertebrate cells in situ by somatic mutation of retrovirally transduced expression constructs (somatic mutation approach), or third, by V(D)J recombination of retrovirally transduced expression constructs containing the coding regions for variable binding domains of antibodies in "quasi-germline" configuration, i.e. still separated into V, optionally D and J gene segments (V(D)J recombination approach). It is to be understood that diverse collections of binding proteins, including antibodies or fragments thereof, can also be generated by any combination of the above-mentioned methods. Preferably, said binding proteins or antibodies or fragments thereof are displayed on the surface of precursor lymphocytes.

The present invention particularly provides methods allowing the stable, and optionally clonal, expression of diverse collections of binding proteins, preferably antibodies, in vertebrate cells using retroviral transduction, which greatly facilitates the amplification, isolation, and cloning of binding protein encoding genes, in comparison to alternative, plasmid-based or non-integrating virus-based vertebrate expression systems known in the art. As a representative but not limiting example, the retroviral transduction of murine precursor lymphocytes that are incapable of expressing endogenous antibodies is disclosed, such that only heterologous, recombinant antibodies are expressed in the host cells as membrane-bound antibodies. Furthermore, the invention illustrates how cells that express ligand- or antigen-reactive binding proteins, such as antibodies or fragments thereof, can be isolated and optionally expanded in vitro, in order to iteratively enrich for a population of antigen-reactive binder cells, from which genes encoding antigen- or ligand-reactive binding proteins can subsequently be cloned and sequenced by standard molecular biology procedures known in the art (FIG. 1).

Although a preferred embodiment of the method according to the invention is directed to the retroviral expression of binding proteins, preferably human, full-length antibodies, it can likewise be used for the expression of any fragment thereof (e.g. single chain $F_v$ or $F_{ab}$ fragments of antibodies). Retroviral transduction protocols are disclosed which optionally allow (i) delivery of single binding protein encoding constructs into single target cells, in order to ensure clonal expression of binding proteins in the host cells; (ii) shuffling of at least one expression construct encoding a first polypeptide chain with at least one expression construct encoding a second polypeptide chain, thereby generating a functional multimeric binding protein (e.g. an antibody molecule); (iii) somatic mutation of at least one expression construct encoding at least one binding protein upon transduction of vertebrate cells in situ; and (iv) generation of binding protein expression from at least one expression construct by the mechanism of V(D)J recombination upon retroviral transduction into vertebrate cells in situ.

In order to achieve somatic mutation of binding protein encoding constructs in situ, retroviral expression vectors and their utilization are disclosed, wherein said vectors contain cis-regulatory genetic elements targeting somatic hypermutation to protein encoding sequences, preferably via an activation-induced cytidine deaminase (AID) pathway (Papavasiliou & Schatz, 2002), or by using other enzymes targeting somatic mutations to binding protein encoding sequences. For the generation of diverse collections of binding proteins, preferably antibodies or fragments thereof, by V(D)J recombination in situ, retroviral vector constructs and their utilization are disclosed, wherein said constructs contain variable (V), optionally diversity (D), and joining (J) gene segments arranged in "quasi-germline" configuration allowing assembly of coding regions for immunoglobulin or immunoglobulin-like binding proteins via recombination activating gene (RAG)-mediated rearrangement of the gene segments by the process known as V(D)J recombination (Grawunder et al., 1998).

According to a further aspect, the present invention further illustrates how retrovirally transduced cells stably expressing diverse collections of recombinant binding proteins are subsequently labelled by binding to at least one ligand or antigen of interest, and how cells binding to the aforementioned ligand or antigen of interest are detected by appropriate secondary reagents. Methods for the specific labelling of ligand- or antigen-reactive cells and their enrichment or isolation, preferably by high-speed fluorescent activated cell sorting (FACS), are described. Due to the stable expression phenotype of retrovirally transduced cells, it is described how antigen-reactive cells may optionally be isolated and again expanded in tissue culture, such that optionally iterative cycles of antigen labelling, antigen-directed enrichment, and expansion of ligand or antigen-reactive cells can be performed, until subcloning of the cells is performed allowing the identification of the nucleotide coding region for antigen-reactive antibodies by standard PCR cloning methods (FIG. 1).

The methods disclosed herein allow the expression of diverse collections of antibody chains or fragments thereof from at least one vector construct, which optionally can give rise to collections of diverse binding proteins upon transfer and expression into vertebrate cells in situ. Expression of antibody chains in vertebrate cells is preferably mediated by retroviral transduction.

As such, a first aspect of the present invention refers to a method for the isolation and identification of at least one nucleotide sequence encoding an antibody or fragment thereof specific for a desired antigen or ligand, comprising the steps of:

(a) transducing at least one retroviral expression construct encoding an antibody or fragment thereof into vertebrate host cells;

(b) expressing said antibody or fragment thereof in said vertebrate host cells;

(c) enriching vertebrate host cells expressing said antibody or fragment thereof on the basis of its ability to bind to said desired antigen or ligand; and (d) isolating and identifying said at least one nucleotide sequence encoding said antibody or fragment thereof from the retrovirally transduced and enriched vertebrate host cells.

In addition to the aforementioned steps, step (d) may be preceded by a step of expanding the enriched vertebrate host cells in tissue culture. Furthermore, step (c) may be followed by a step of expanding the enriched vertebrate host cells in tissue culture, after which step (c) is repeated at least once before step (d) is carried out.

To achieve clonal expression of at least one antibody it is preferable to control the retroviral transduction such that the majority of retrovirally transduced cells are genetically modified by only one recombinant retroviral construct per antibody chain integrating in to the host cell genome. Therefore, in one embodiment of the present invention, retroviral transduction is performed at a multiplicity of infection (MOI) of equal to or less than 0.1.

An antibody according to a method of the present invention is preferably a full-length antibody. A fragment of an antibody may be selected from the group consisting of: a heavy chain, a light chain, a single $V_H$ domain, a single $V_L$ domain, a scFv fragment, a Fab fragment, and a F(ab')2 fragment. The antibody or fragment(s) thereof may have a naturally occurring amino acid sequence, an artificially engineered amino acid sequence or a combination thereof.

Whilst the method of the present invention is used preferably for the isolation and identification of at least one nucleotide sequence encoding an antibody chain, it would be apparent to a person skilled in the art that the method of the present invention can also be used for the isolation and identification of at least one nucleotide sequence encoding any monomeric or multimeric cell surface receptor belonging to the Ig-superfamily, and any functional fragment thereof, or a monomeric or multimeric cell surface receptor belonging to the TNFα-receptor superfamily, or any fragment thereof.

Furthermore, where the binding protein is a full-length antibody, the full-length antibody is selected from the group consisting of a fully human antibody, a humanized antibody, in which CDR regions of a non-human antibody or antibodies have been grafted onto a human antibody framework, and a chimeric antibody, in which variable region domains from one vertebrate species are combined with constant region domains of another vertebrate species, with the constant domain of the chimeric antibody preferably being derived from a human antibody or antibodies.

In an embodiment of the methods disclosed herein, the vertebrate host cells may be derived from a group of species comprising cartilaginous fish, bony fish, amphibians, reptilia, birds and mammals. The group of species of mammals may include pigs, sheep, cattle, horses and rodents. The group of rodents may further comprise mice, rats, rabbits and guinea pigs. In a preferred embodiment of the present invention, the vertebrate host cell species is mouse (*Mus musculus*).

The vertebrate host cells for use in a method of the present invention can be derived from any vertebrate organ, but are preferably derived from lymphocyte lineage cells. The preferred lymphocytes for use in the present invention are of the B cell lineage, because these cells express antibody-specific chaperone proteins, and because accessory molecules, like Igα and Igβ required to mediate cell surface anchoring of antibodies are expressed in these cells. More preferably, the B cells are precursor B lymphocytes, as preB cells can be found that do not express any endogenous antibody chains. In fact, the preferred lymphocytes as utilised in the present invention are unable to express endogenous antibody polypeptides including components of the so-called surrogate light chain, encoded by the genes lambda-5, VpreB1 and VpreB2. Therefore, the preferred lymphocytes express accessory membrane proteins facilitating membrane deposition of antibody molecules, such as the B cell specific Igα and Igβ molecules, but they lack expression of any endogenous antibody polypeptide or surrogate light chain component. However, it shall be noted that it may be possible to express Igα and Igβ molecules ectopically, by methods known in the art, e.g. stable transfection with expression vectors for these proteins. In a preferred embodiment of the present invention, antibody molecules are anchored to the cell membrane of lymphocytes via endogenously expressed Igα and Igβ proteins, which are naturally expressed in murine pre-B lymphocytes.

The methods disclosed herein include procedures allowing the isolation of cells displaying desired binding characteristics for a ligand or antigen of interest and the isolation of genes encoding a desired binding protein of interest. The preferred method of retroviral expression of an antibody in vertebrate cells disclosed herein allows for stable and preferably clonal expression of antibodies, which greatly facilitates the amplification, isolation, and cloning of antibody encoding genes, in comparison to alternative, plasmid-based or non-integrating virus-based vertebrate expression systems known in the art. The disclosed methods allow for efficient generation of diverse collections of binding proteins in vitro by either:

(i) shuffling of at least one expression construct encoding at least one polypeptide chain of a multimeric binding protein (like e.g. a heavy chain of an antibody), with at least one expression construct encoding at least one matching polypeptide chain (like e.g. a light chain of an antibody) generating a functional multimeric binding protein (like e.g. an antibody);

(ii) somatic mutation of at least one expression vector encoding at least one binding protein upon transfer into vertebrate cells in situ;

(iii) somatic recombination of V (variable), optionally D (diversity), and J (joining) gene segments encoding variable binding domains of immunoglobulins and immunoglobulin-like molecules contained in at least one expression vector upon transfer into vertebrate cells in situ, by the process known as V(D)J recombination; or (iv) by any combination of procedures (i), (ii), and (iii).

According to a preferred embodiment, the at least one nucleotide sequence is a plurality of nucleotide sequences that comprise an antibody heavy chain sequence and multiple antibody light chain sequences, or—in the alternative—comprise an antibody light chain sequence and multiple antibody heavy chain sequences.

According to another preferred embodiment, the antibody or fragment thereof comprises a variable binding domain encoded by the at least one retroviral expression construct enabling V(D)J recombination in order to generate a coding sequence for a variable binding domain upon retroviral transduction or In a further preferred embodiment, step (b) of the above method is performed under mutagenizing conditions, preferably via the expression of activation induced cytidine deaminase (AID) which is either endogenously or ectopically expressed, wherein the ectopic expression of AID is performed under inducible conditions.

In one aspect of the above method, the at least one retroviral expression construct encoding said antibody or fragment thereof contains a combination of cis-regulatory promoter and enhancer elements allowing the targeting of AID mediated somatic mutation to a variable binding domain encoded by the expression construct, wherein the promoter and enhancer elements are selected from the group consisting of (a) immunoglobulin heavy chain promoter, intron enhancer (EμH) and 3'α enhancer elements, (b) immunoglobulin κ light chain promoter, κ intron enhancer (κiE) and 3'κ enhancer (3'κE) elements, (c) immunoglobulin λ light chain promoter, λ2-4 and λ3-1 enhancer elements, and (d) any functional combination thereof.

Figure 2A:
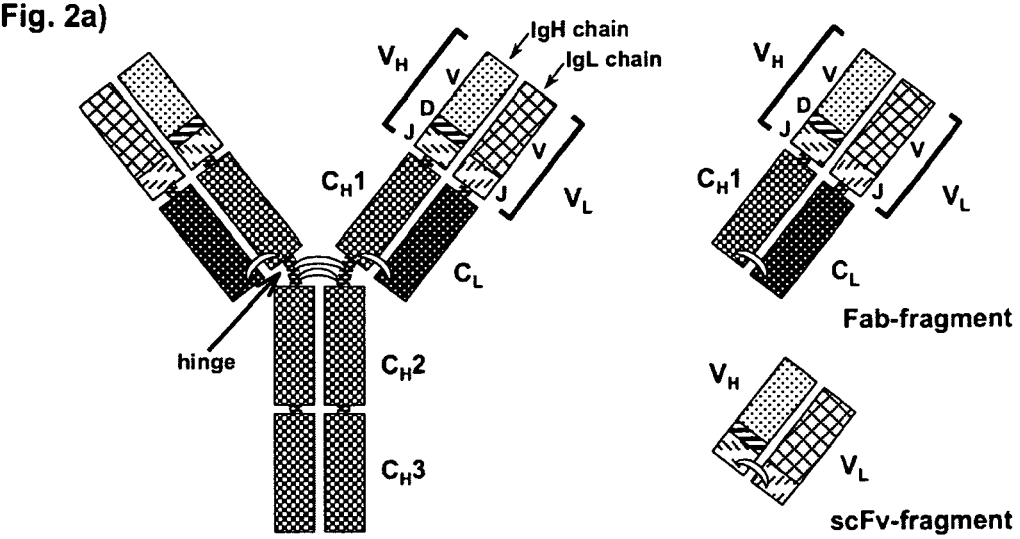
FIG. 2a) shows the schematic structure of an IgG antibody (left), which is characterized by a characteristic Y-shaped structure and is composed of two identical immunoglobulin (Ig) heavy and light chains, comprising four ($V_H$—$C_H1$-$C_H2$-$C_H3$) and two immunoglobulin domains ($V_L$—$C_L$), respectively. The V-domains are the highly variable antigen binding regions of IgH and IgL chains, whereas the $C_H$ and $C_L$ domains represent the constant region domains. The variable region domains of IgH chains are encoded by V, D and J gene segments, whereas the variable region domains of IgL chains are encoded by only V and J gene segments, which need to be assembled from germline immunoglobulin gene loci (FIG. 2b) and 2c) during early B lymphopoiesis, by the process known as V(D)J recombination.

Antibody IgH and IgL chains are covalently held together by disulphide bridges, which couple the identical IgH chains together at a location close to the flexible hinge region, i.e. between the $C_H1$ and $C_H2$ domains, whereas additional disulphide bridges between the $C_H1$ and $C_L$ domains, as depicted, are covalently coupling IgH and IgL chains (FIG. 2a left).

Fab fragments are univalent fragments of full-length antibodies only containing $V_H$—$C_H1$/$V_L$—$C_L$ domains coupled by a natural disulphide bridge, which can either be derived by enzymatic papain cleavage from full-length antibodies, or which can be expressed as recombinant proteins by expressing $C_H2$-$C_H3$ deleted IgH chains together with IgL chains. Additional fragments of fully human antibodies are single chain variable domain fragments (scFv-fragments), which only comprise the variable region domains of IgH and IgL chains that are coupled by a synthetic linker or an artificial disulphide bridge. The expression of either full-length antibodies, or antibody fragments, as the depicted Fab and scFv fragments, may also be expressed as binding proteins in order to realize the invention.

Figure 2B:
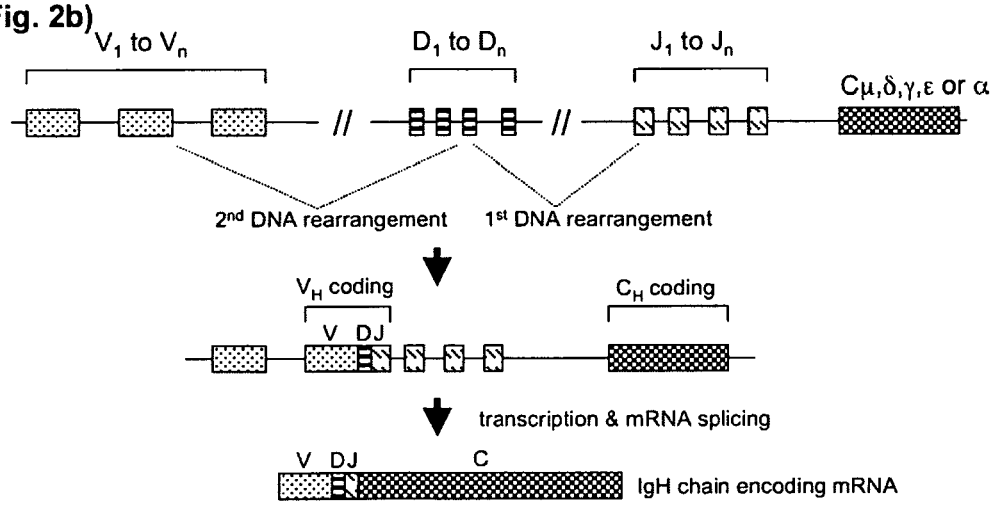
FIG. 2: (a) This figure illustrates the schematic structure of antibodies or immunoglobulins and fragments thereof, which are the preferred binding proteins according to the disclosed invention.

FIG. 2b) schematically depicts the process of V(D)J recombination occurring on a germline IgH chain allele, resulting in the assembly of the coding regions of antibody $V_H$ domains. The variable domains of IgH chains in vertebrate species are encoded by a multitude of V, D and J gene segments, which are separated in germline configuration. During V(D)J recombination occurring during early lymphopoiesis, one selected V, D and J gene segment is site-specifically rearranged to generate a unique coding region for an antibody $V_H$ domain. V(D)J recombination in the IgH chain locus is an ordered process and starts with rearrangement of a selected D to a selected J gene segment, usually on both IgH chain alleles. Only after D to J gene rearrangement, one selected V region is site-specifically joined to the already assembled DJ region, thereby generating a V-D-J ORF encoding the $V_H$ domain. The process of V(D)J recombination is dependent on the expression of precursor lymphocyte specific recombination activating genes (RAG) 1 and 2.

Figure 2C:
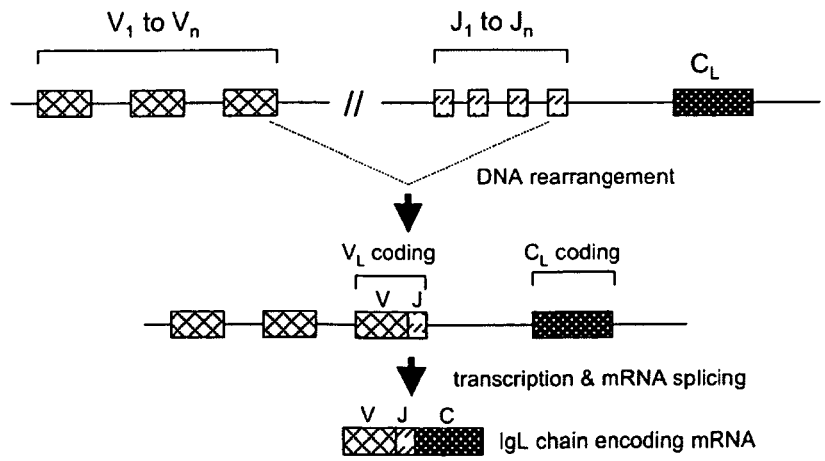

FIG. 2c) schematically depicts the process of V(D)J recombination occurring on a germline IgL chain allele, resulting in the assembly of the coding regions of antibody $V_L$ domains. The variable domains of IgL chains in vertebrate species are encoded only by V and J gene segments, which are separated in germline configuration, similar to the gene segments in the IgH chain locus. The generation of an antibody $V_L$ domains requires only one site-specific V(D)J recombination event, as depicted.

FIG. 3: This figure schematically illustrates the principle of stable genetic modification of target cells for the expression of a binding protein of interest (BPOI) such as an antibody (alternatively labelled "X") by retroviral transduction.

FIG. 3a) depicts the schematic organization of a wild-type retroviral genome (upper left), in which the genes for the structural and functional proteins Gag, Pol and Env are located in between so-called 5' and 3' long-terminal repeat (LTR) sequences flanking the retroviral genome. The 5'LTRs are important for the expression of the retroviral genes and also for the replication of the retroviral genome in the infected host cell. Another important region in the retroviral genome is the ψ (Psi) packaging signal, which is required for the packaging of the retroviral RNA during replication and/or production of retroviral particles.

For the generation of recombinant retroviral particles, the gag, pol and env genes may be removed from a wild-type retroviral genome, so that only 5' and 3' LTRs and the ψ (Psi) packaging signal remains. For the construction of recombinant retroviral vectors it is then convenient to introduce a multiple cloning site (MCS) containing several unique and convenient restriction enzyme sites. This design, as depicted on top/right, represents the simplest retroviral transfer vector.

For the expression of recombinant retroviruses allowing the expression of a recombinant protein (e.g. a binding protein of interest (BPOI) "X") such as an antibody, minimally an open reading frame (ORF) of a BPOI needs to be inserted into an "empty" retroviral transfer vector, as the 5'LTR region has a promoter activity able to drive expression of any downstream positioned gene. However, in order to improve expression levels, expression of a gene of interest (e.g. a BPOI-"X") may optionally be driven by an additional heterologous promoter (Prom.), and optional addition of a marker gene, e.g. downstream of the 5'LTR promoter and ψ packaging signal, as depicted here, may allow selection and/or tracking of retrovirally transduced constructs.

FIG. 3b) schematically illustrates the procedure of retroviral transduction of target cells resulting in the stable expression of a BPOI-"X" such as an antibody. For this, first, a recombinant retroviral construct containing an expression cassette for a BPOI-"X" is transiently transfected into a retroviral packaging cell line (PCL), expressing structural and functional retroviral proteins Gag, Pol and Env of a wild-type retrovirus (left). A retroviral PCL can be generated by either stably or transiently transfecting expression constructs for the Gag, Pol and Env proteins into a suitable and easy to transfect cell line (e.g. standard human 293 HEK cells, or mouse NIH 3T3 fibroblasts). Two to three days post transfection, the recombinant retroviral genomes, containing the BPOI-"X" gene are packaged into replication incompetent retroviral particles, which accumulate in the cell culture supernatant of the PCL. The retroviral particles are replication incompetent, because they lack the genes for the functional retroviral Gag, Pol and Env proteins and therefore, they can deliver their genetic payload into a target cell only once, a process that is called retroviral transduction, or single round infection. During retroviral transduction the packaged RNA of a recombinant retrovirus is introduced into the target cells, where it is reverse transcribed into cDNA, which is then stably integrated into the target cell genome. Two to three days after retroviral transduction, a gene of interest, like the BPOI-"X", is then permanently expressed by the target cells, due to the integration of the cDNA retroviral construct into the host cell genome.

Figure 4:
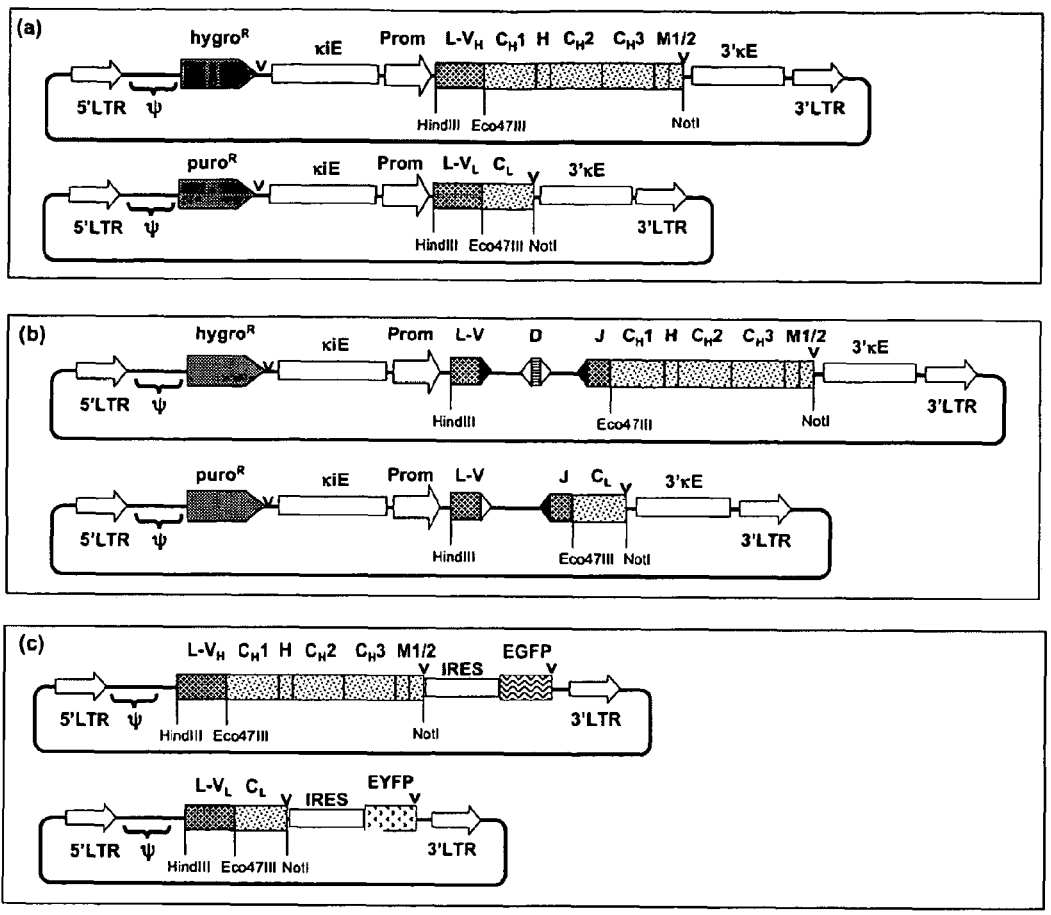

FIG. 4: This figure shows the schematic design of preferred types of retroviral expression constructs that can be used to realize the invention. The drawing depicts the schematic design of retroviral vectors contained in a standard DNA cloning plasmid backbone (closed black line); the relevant genes and regions for the retroviral genome are highlighted. One preferred vector generation, depicted in panel (a), whose detailed cloning is described in FIGS. 5 and 6, and provided in Example 1, contains the cDNA coding regions for human Igγ$_1$H chains and IgκL chains driven by a strong constitutive CMV promoter (Prom) and flanked up- and downstream by the Igκ intron enhancer (κiE) and 3'κ enhancer (3'κE) elements, promoting somatic hypermutation to the V coding regions of the IgH and IgL chains. The retroviral IgH and IgL chain expression constructs additionally contain open reading frames for the antibiotic resistance markers hygromycinB (hygro$^R$) and puromycin (puro$^R$), respectively, allowing the selection of stable integration of the IgH and IgL chain constructs applying respective antibiotic drug selection to cultures of retrovirally transduced vertebrate cells. In addition, convenient, unique restriction enzyme sites are highlighted, allowing the straightforward replacement of V coding regions with HindIII and Eco47III, or the replacement of the entire IgH and IgL chain coding regions by using the restriction enzymes HindIII and NotI. This way, from one existing IgH or IgL chain expression construct different V regions and even entire collections of V regions can easily be cloned into the disclosed expression vectors.

(b) In this panel, another class of preferred vectors is described, which carry a replacement of the variable coding region by a DNA fragment, in which the variable coding region is still separated into V, D and J gene segments (for the IgH construct) and V and J gene segments (for the IgL chain construct) in "quasi-germline" configuration. While otherwise identical to the retroviral expression vectors provided in (a) these V(D)J-recombination competent retroviral vectors first need to undergo site-specific rearrangement of the V, optionally D and J gene segments, in order to generate a coding region for a variable binding domain of a IgH or IgL chain. The detailed cloning of such a vector allowing the expression of IgH chains after V(D)J recombination is described in FIG. 11.

A unique feature of these constructs is their capability to generate diverse V domain coding regions in V(D)J recombination active cells in situ, e.g. in precursor lymphocytes expressing endogenous RAG1 and RAG2 proteins. Because the process of V(D)J recombination is not precise, a diverse collection of variable coding region sequences may result from one individual retroviral vector within a given set of V, D and J gene segments for IgH, or a given set of V and J gene segments for IgL. The diversity in the joining of V, optionally D and J gene segments is due to a combination of exonuclease activity, TdT mediated N-region addition, and P nucleotide generation, which may all contribute individually or jointly to coding joint diversification. As the V, D and J gene segments have been cloned in a fashion that different V, D and J gene segment family members can be easily replaced by unique restriction enzyme sites, a limited number of constructs generated and introduced into V(D)J recombination competent host cells, can result in an enormous diversity of in situ generated binding protein diversity. As these vectors contain additional κiE and 3'κE elements, conferring somatic hypermutation to an V(D)J-rearranged V domain coding region, a primary in situ generated collection of diverse binding proteins can optionally further be mutagenized by an AID-dependent somatic hypermutation process. This way, the entire process of generation of antibody diversity in vivo, can be recapitulated in situ and in vitro using the disclosed retroviral constructs and host cells exhibiting V(D)J recombination activity (e.g. precursor lymphocytes), and in which AID mediated somatic hypermutation is active, or can be activated.

(c) This panel schematically depicts yet another design of retroviral constructs that can be used to realize the invention. Here, the expression of the IgH and IgL coding regions is driven by the 5'LTR promoter of the retroviral backbone and the expression of IgH and IgL chains is coupled to the expression of GFP and YFP autofluorescence markers, respectively, allowing the tracking and isolation of IgH and IgL expressing cells simply by analyzing the transduced cells for green and yellow fluorescence. These constructs are very useful for controlling the multiplicity of infection of "selector cells" without further labelling procedures.

A legend of symbols used in FIGS. 4a) to c) for important DNA sequences included in the construct is provided. The subdivision of the IgH and IgL coding regions into variable domains ($V_H$ and $V_L$) all containing endogenous leader (L) sequences, hinge (H), constant ($C_H1$, $C_H2$, $C_H3$, $C_L$), and membrane-spanning coding regions (M1/2, because this region is encoded by two exons) is provided for a better understanding of the illustrations.

Figure 5A:
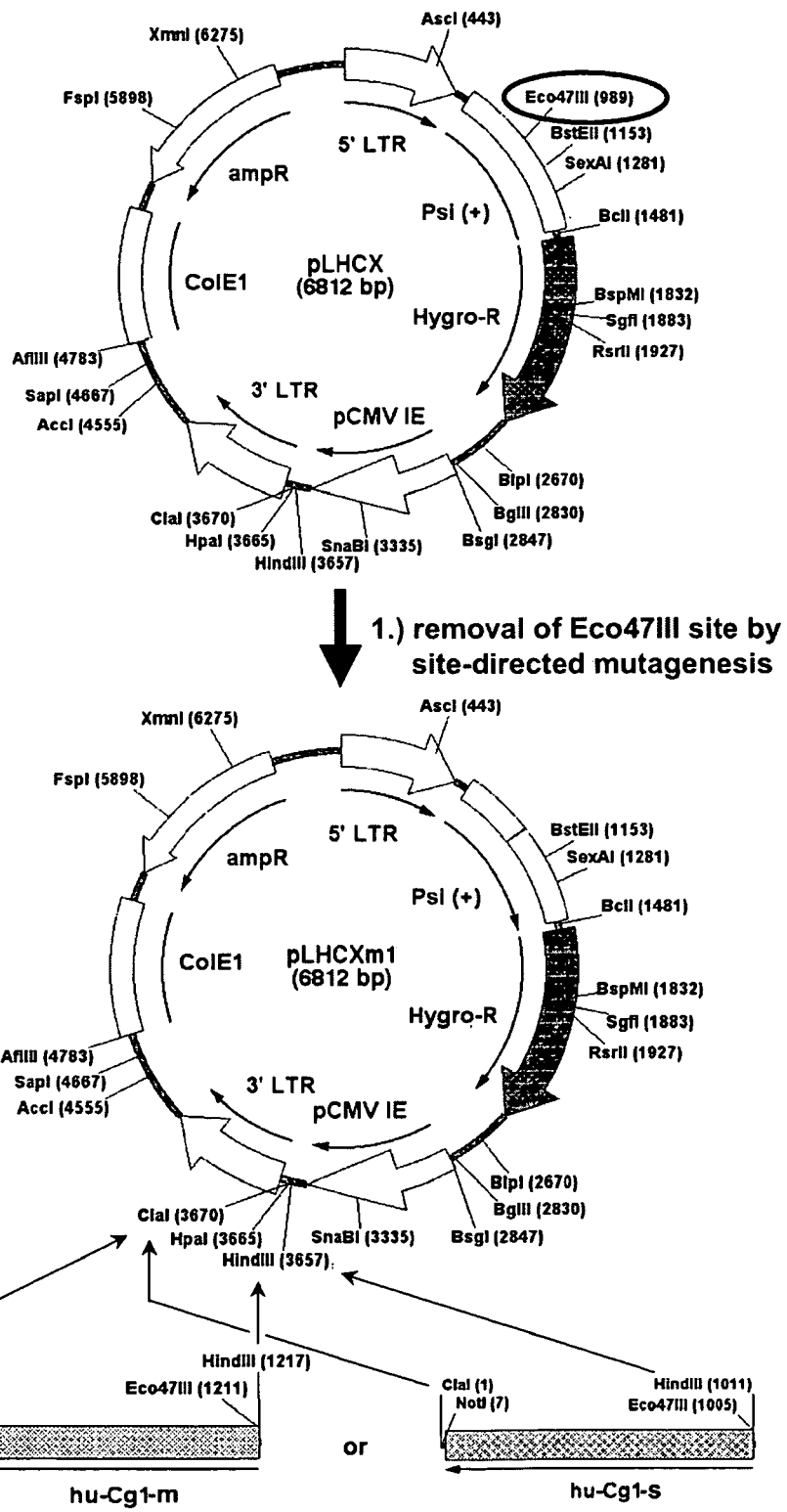
Figure 5B:
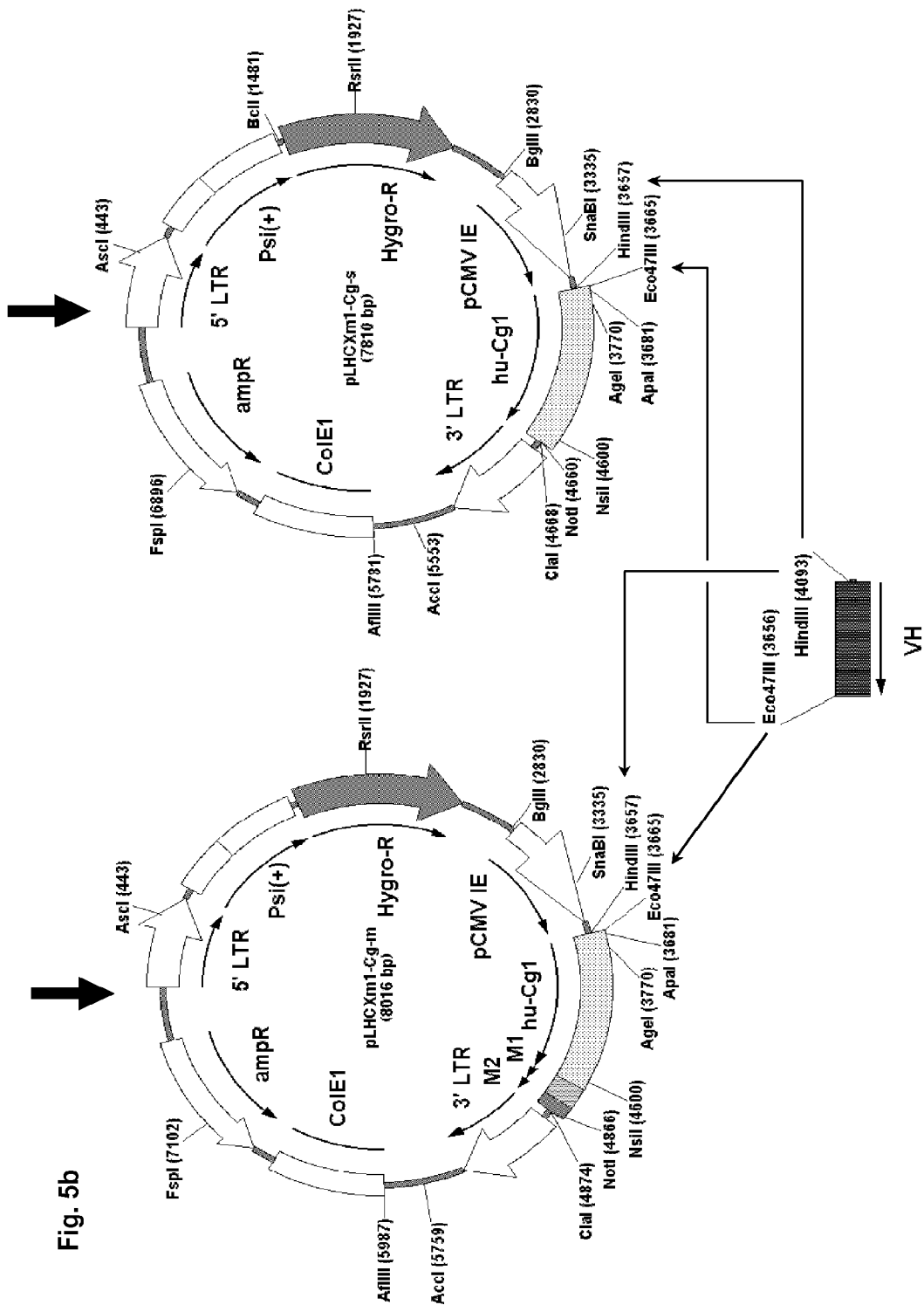
Figure 5C:
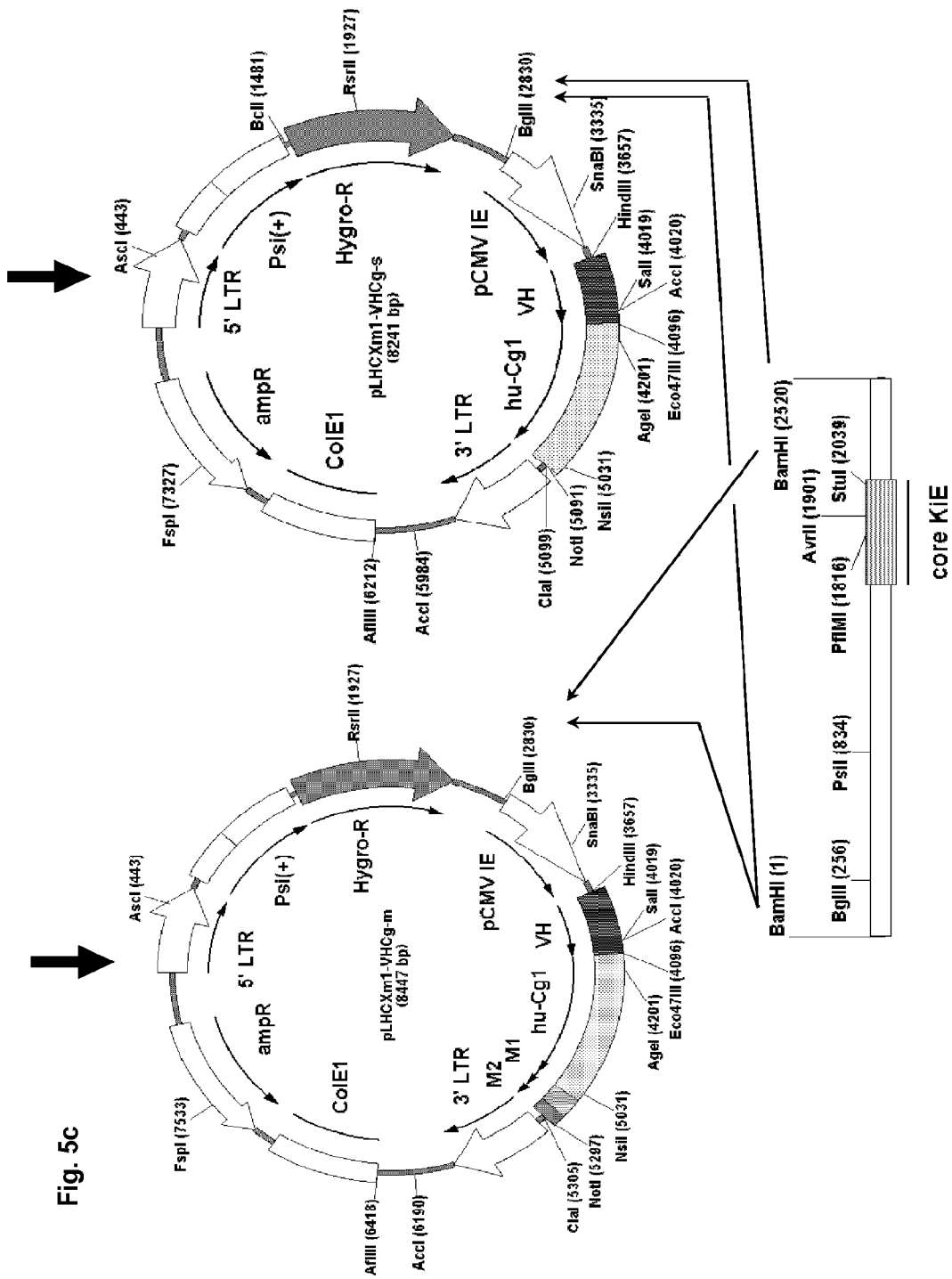

FIG. 5a-e illustrates the cloning strategy for the construction of a retroviral IgH (human Igγ$_1$ isotype) expression vector, disclosed in detail in Example 1, and in the basic design provided in FIG. 4(a). The cloning of expression constructs for both membrane bound IgG as well as secreted IgG is depicted, as detailed in Example 1—unique restriction enzyme sites in the plasmid maps are provided for general reference purposes. Based on the final retroviral chain expression construct, as disclosed in FIG. 5e herein, any other $V_H$ domain coding region, or a collection (library) of diverse $V_H$ domain coding regions can be introduced into the vectors using the unique HindIII and Eco47III restriction enzyme sites, by replacing the existing $V_H$ region with said any other $V_H$ domain coding regions. FIG. 5a depicts a first preparatory cloning step, in which an Eco47III restriction site (circled) is removed from the commercially available pLHCX vector backbone by site-directed mutagenesis, as described in Example 1. This generates the retroviral vector backbone pLHCXm1, in which the Eco47III restriction enzyme site can later be re-introduced for the cloning and replacement of $V_H$ domain coding regions. The advantages of using Eco47III for this purpose is based on the fact that Eco47III is the only restriction enzyme site that can be introduced directly at the border between human $V_H$ and Cγ$_1$ coding regions, without changing the amino acid composition of expressed human Igγ$_1$H chains. FIG. 5a further illustrates, how cloned fragments of the human γ₁ constant region genes, either with, or without membrane spanning exons M1/M2 are cloned into the pLHCXm1 backbone using unique HindIII and ClaI restriction enzyme sites present in the MCS of pLHCXm1. The fragments were designed to contain additional flanking Eco47III and NotI restriction enzyme sites for later cloning purposes, as detailed in Example 1. FIG. 5b) shows the plasmids maps of the cloning intermediates without $V_H$ domain coding regions, and it is shown, how a particular $V_H$ coding region flanked by HindIII and Eco47III sites is cloned into the constructs. These constructs, which are thus generated, are depicted in FIG. 5c, and would in principle be sufficient to confer the expression of human Igγ₁H chains in any recipient cell line. However, the possibility to additionally mutagenize $V_H$ coding regions in an AID-dependent manner, is an aspect of this invention and two additional cloning steps are disclosed, in which the core κiE element with additional flanking sequences is cloned into a unique BglII site, upstream of the CMV promoter of the expression cassette (FIG. 5c bottom and FIG. 5d) and in which the 3'κE element with some flanking DNA sequence is cloned into the unique ClaI site downstream of the expression cassette for human Igγ₁H chains. This results in the final expression vector for either membrane bound or secreted human Igγ₁H chains, for which the plasmid maps are provided in FIG. 5e. These constructs correspond to the schematic plasmid maps that have already been disclosed in FIG. 4a, but here with precise restriction enzyme maps and drawn to scale.

Figure 5D:
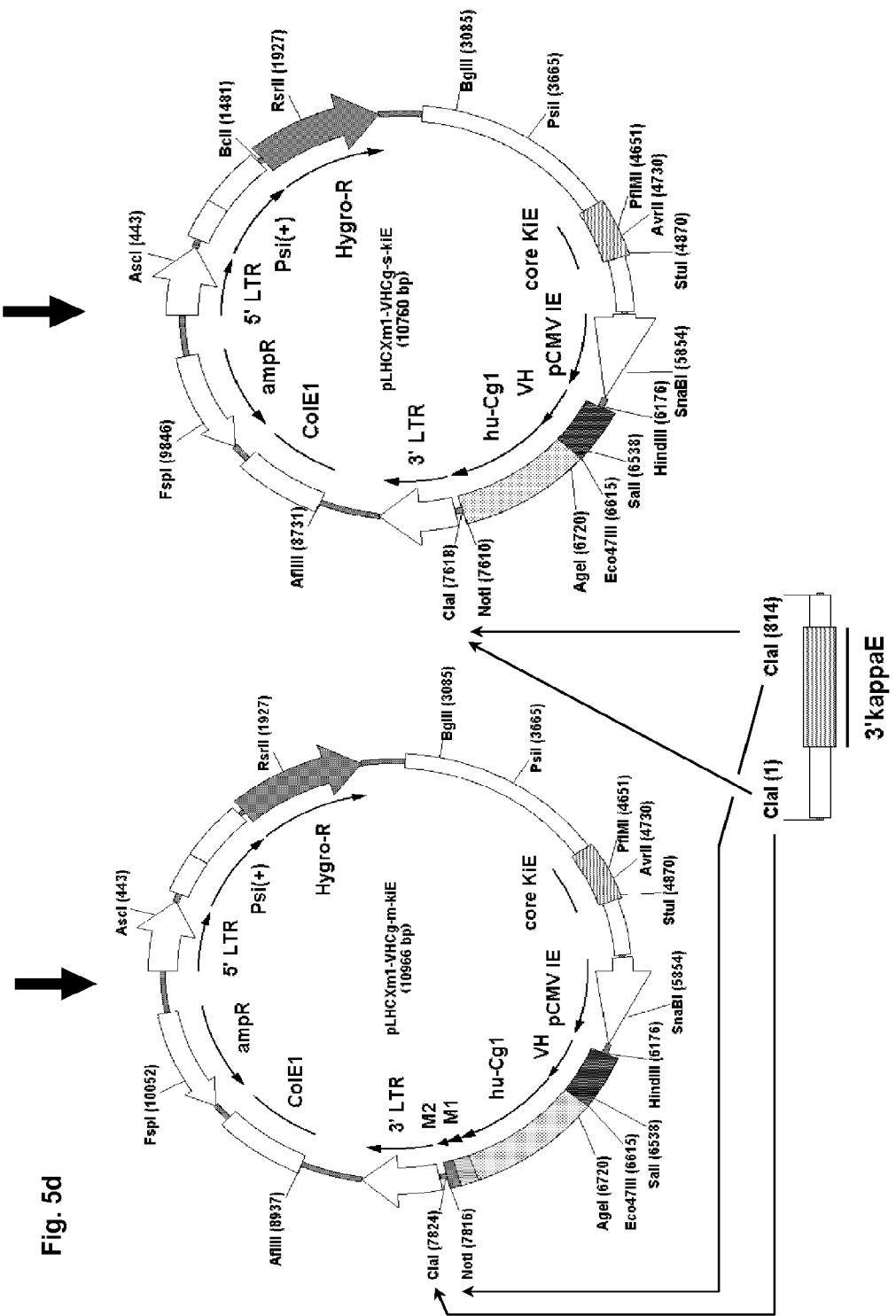
Figure 6B:
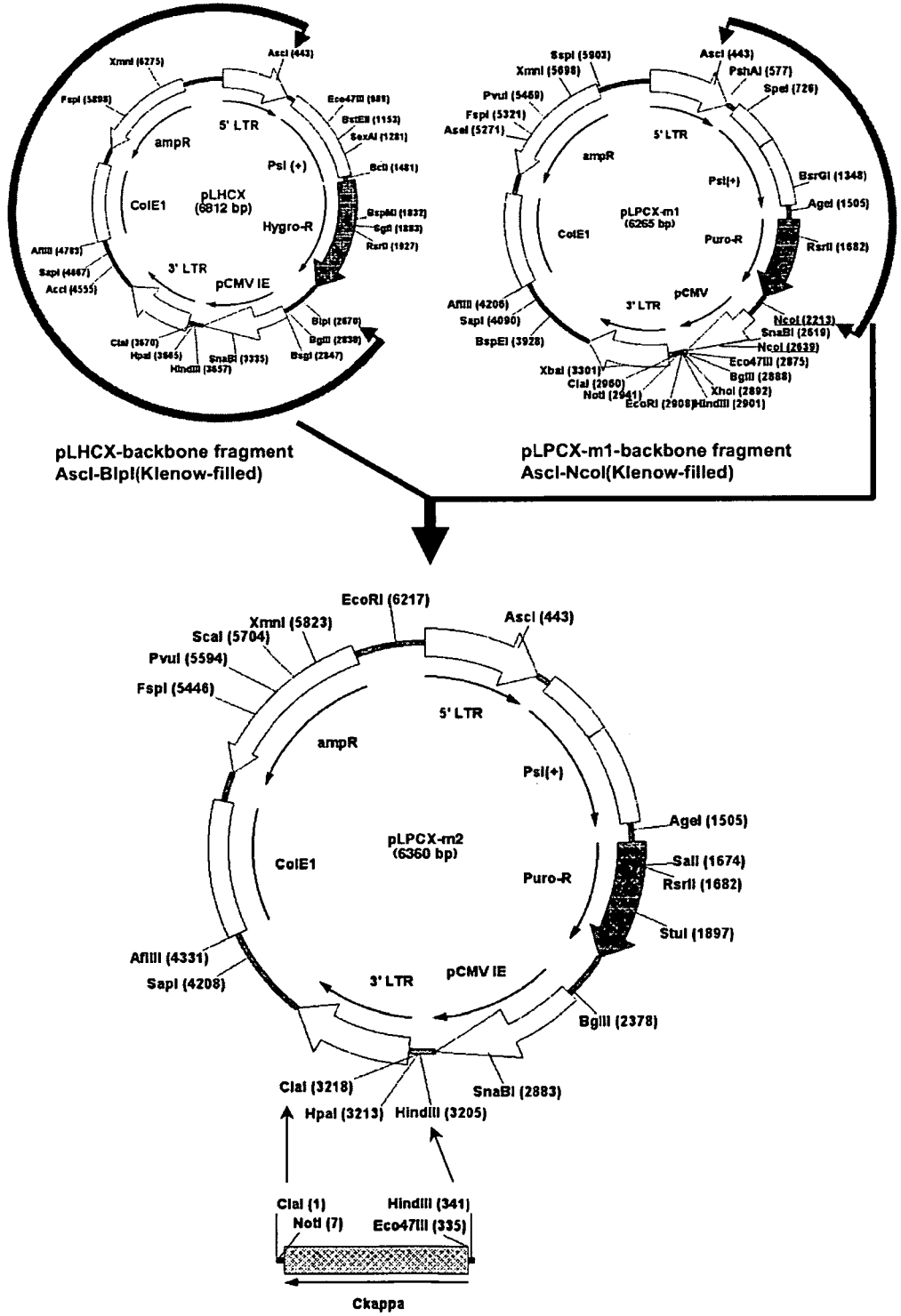
Figure 6C:
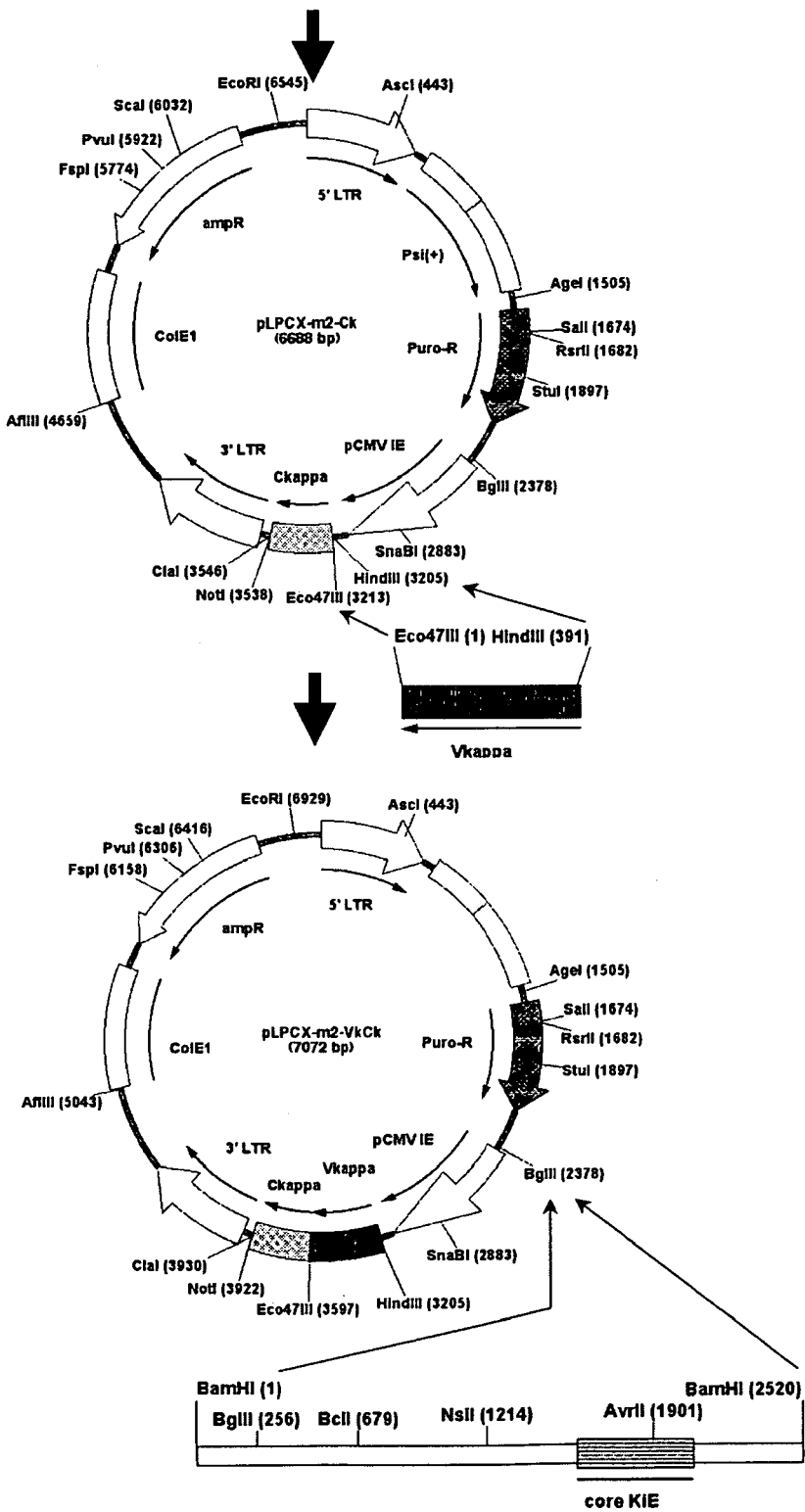
Figure 6D:
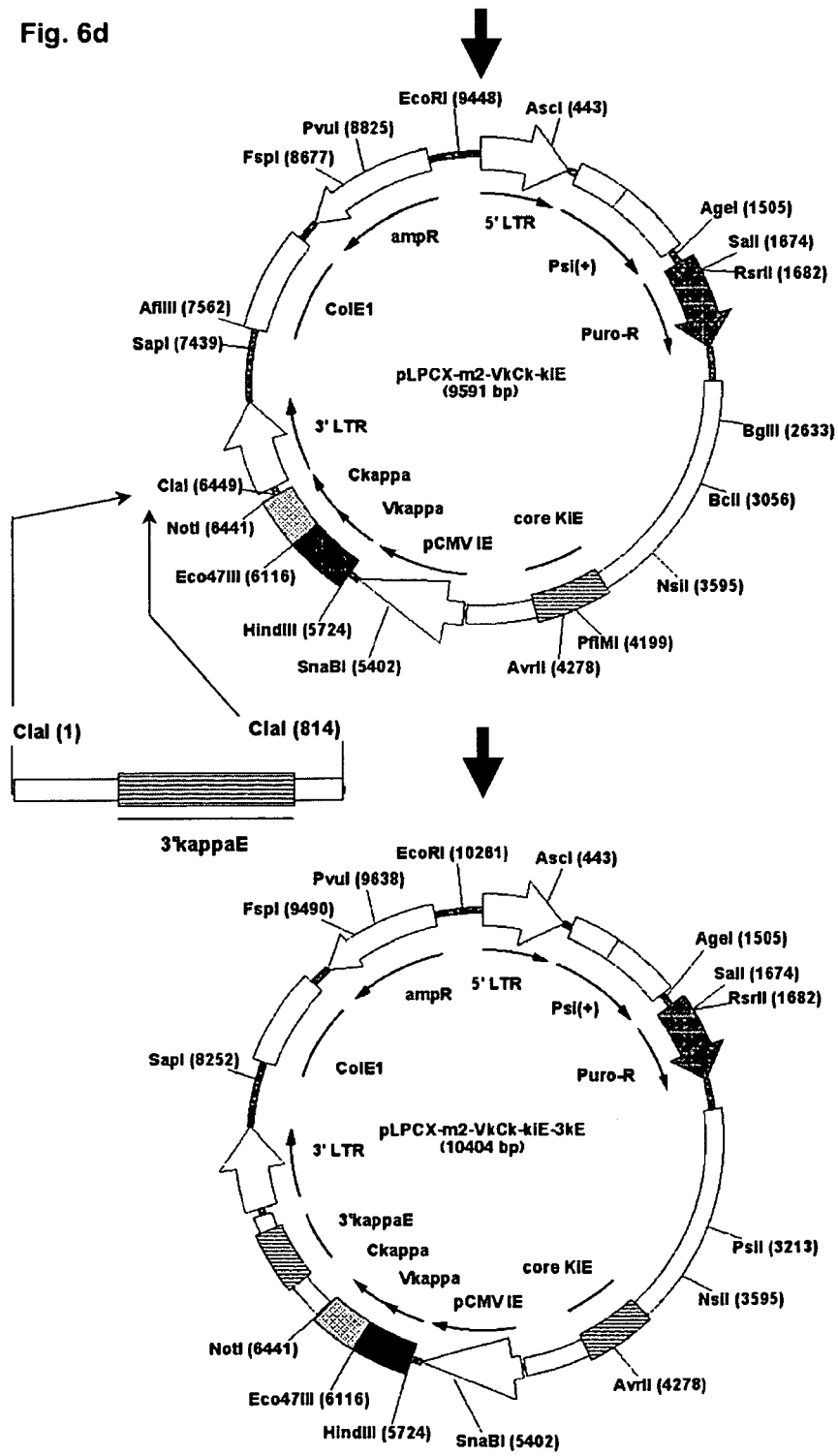

FIG. 6a-d illustrates the detailed cloning strategy provided in Example 1, for the construction of retroviral IgL (human IgκL isotype) expression construct, whose basic design was already provided in FIG. 4(b). Based on the final retroviral IgκL chain expression construct, as disclosed in FIG. 6d herein, any other $V_L$ domain coding region, or a collection (library) of diverse $V_L$ domain coding regions can be introduced into the vectors using the unique HindIII and Eco47111 restriction enzyme sites, by replacing the existing $V_L$ region with said any other $V_L$ domain coding region(s). The cloning strategy for the retroviral IgL chain expression vectors required preparatory cloning steps, in order to generate a modified retroviral vector backbone, into which the desired elements could be cloned using convenient restriction enzyme sites as depicted. In a first step, from commercial plasmid pLPCX an undesired Eco47III site was removed from the ψ (Psi) packaging signal by site-directed mutagenesis as described in Example 2, resulting in modified plasmid pLPCXm1 (FIG. 6a). In a second step a novel pLPCXm2 backbone was generated by ligating a large, AscI-BlpI digested fragment from commercial plasmid pLHCX with an AscI-NcoI fragment from pLPCXm1 (FIG. 6b). For both fragments the non-compatible BlpI and NcoI DNA ends needed to be filled up with nucleotides using Klenow fragment as described in Example 1. Into the resulting pLPCXm2 backbone the constant region for a human κL chain (Cκ) has been inserted via HindIII and ClaI as shown (FIG. 6b). Similar to the cloning strategy for human IgH chains, the human Cκ fragment was further flanked by Eco47III and NotI sites to facilitate additional cloning procedures. After insertion of the human Cκ fragment, one selected human Vκ element was cloned into the construct via unique HindIII and Eco47III sites (FIG. 6c). This construct would in principle be sufficient to confer the expression of human IgκL chains in any recipient cell line. However, like in the case for the IgH chain expression constructs (FIG. 5a-e), additional κiE and 3'κE elements were cloned into the construct into the unique BglII and ClaI sites upstream and downstream of the IgκL chain expression cassette, identical to the cloning strategy of the IgH chain constructs (FIGS. 6c and 6d). In the final constructs also the Vκ domain coding region can then be target for AID-mediated somatic hypermutation. The final construct corresponds to the schematic plasmid map that is detailed in FIG. 4(b), but here the precise restriction enzyme maps are included and drawn to scale.

Figure 7:
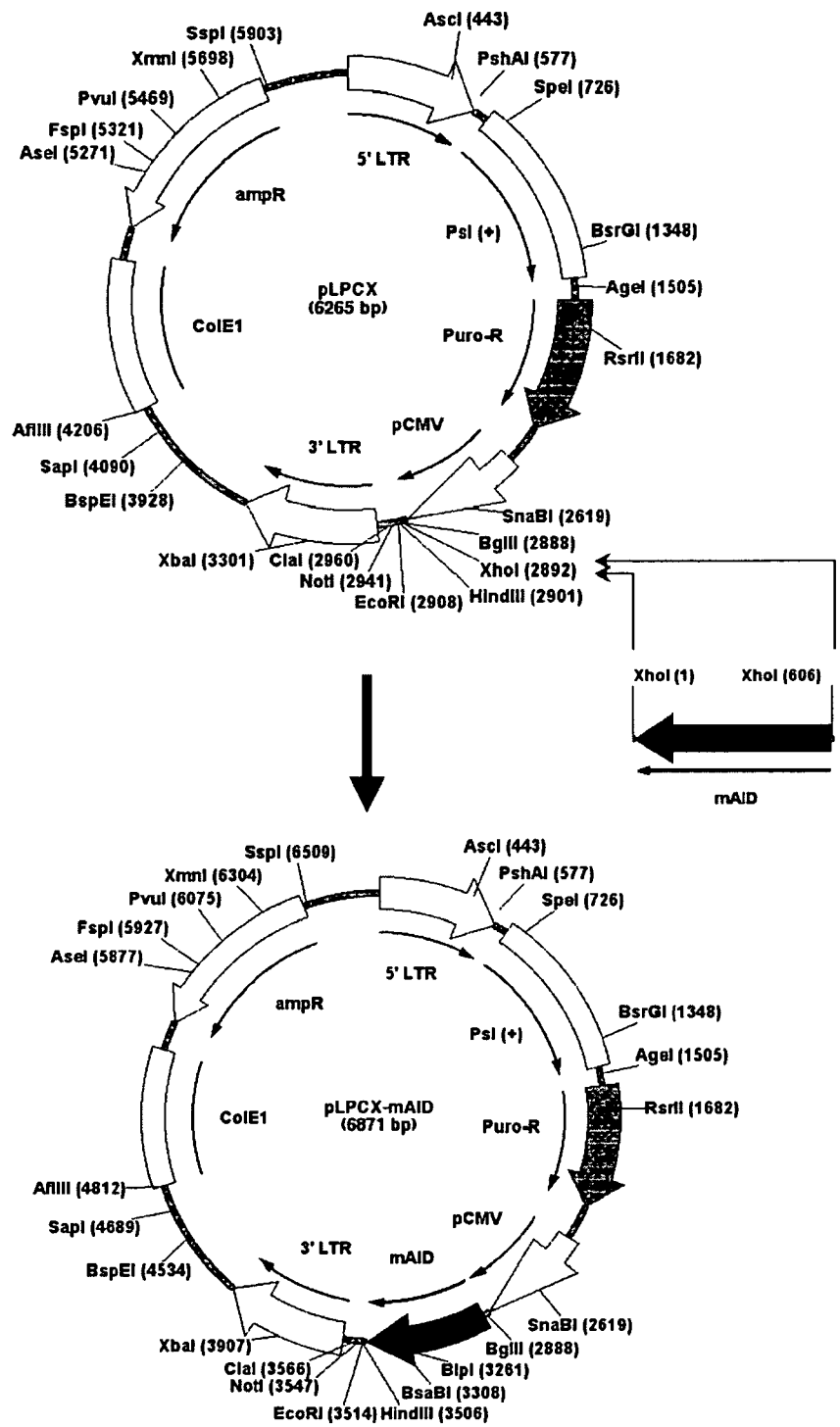

FIG. 7: This figure illustrates the cloning strategy for a retroviral expression construct for activation induced cytidine deaminase (AID). As depicted, the commercial pLPCX retroviral vector backbone was used and a specific RT-PCR-fragment from mouse splenic cDNA containing the AID coding region was cloned into the unique XhoI restriction site of the pLPCX vector using compatible XhoI restriction enzyme sites inserted into the PCR amplication primers, as described in Example 2.

Figure 8A:
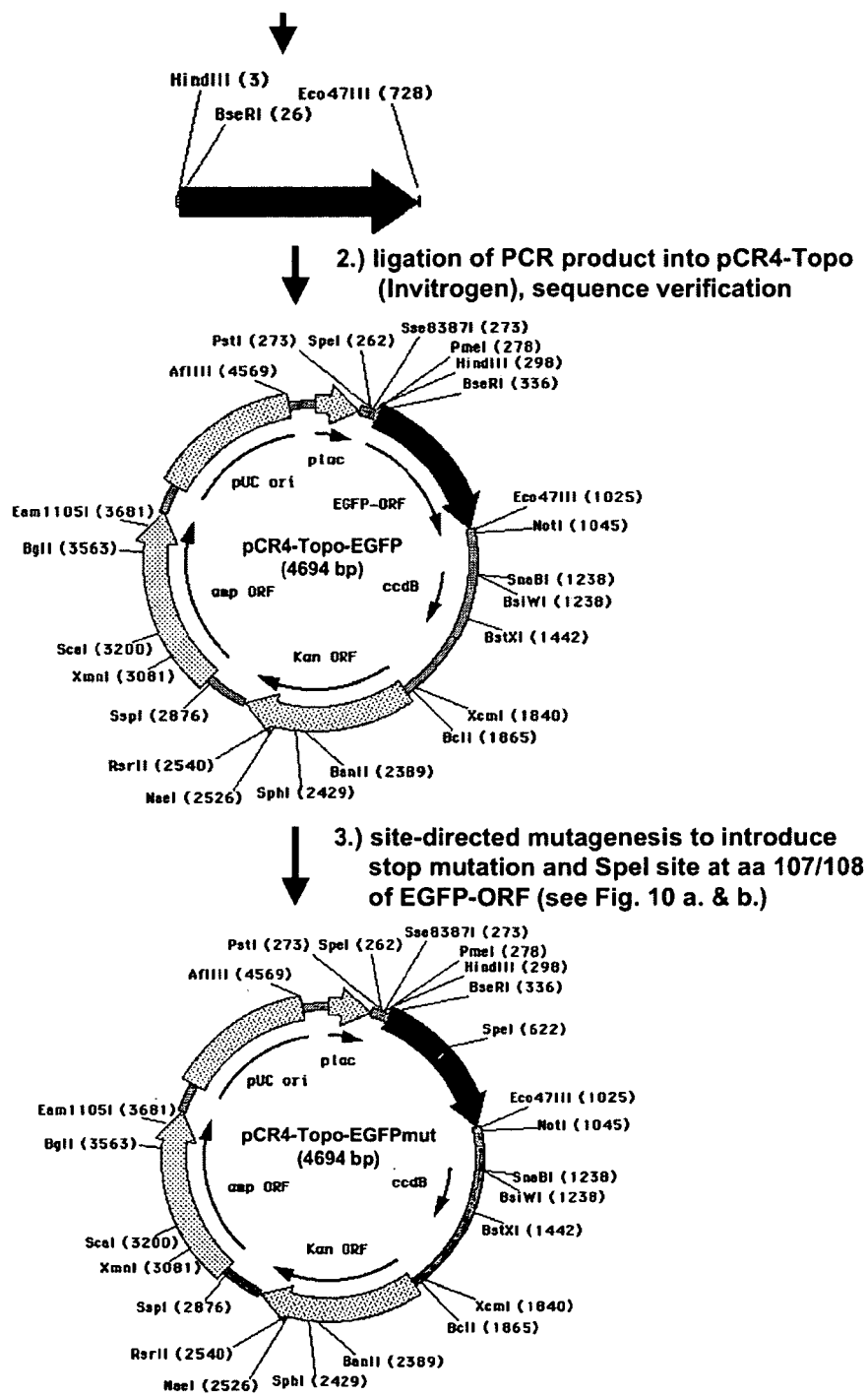
Figure 8B:
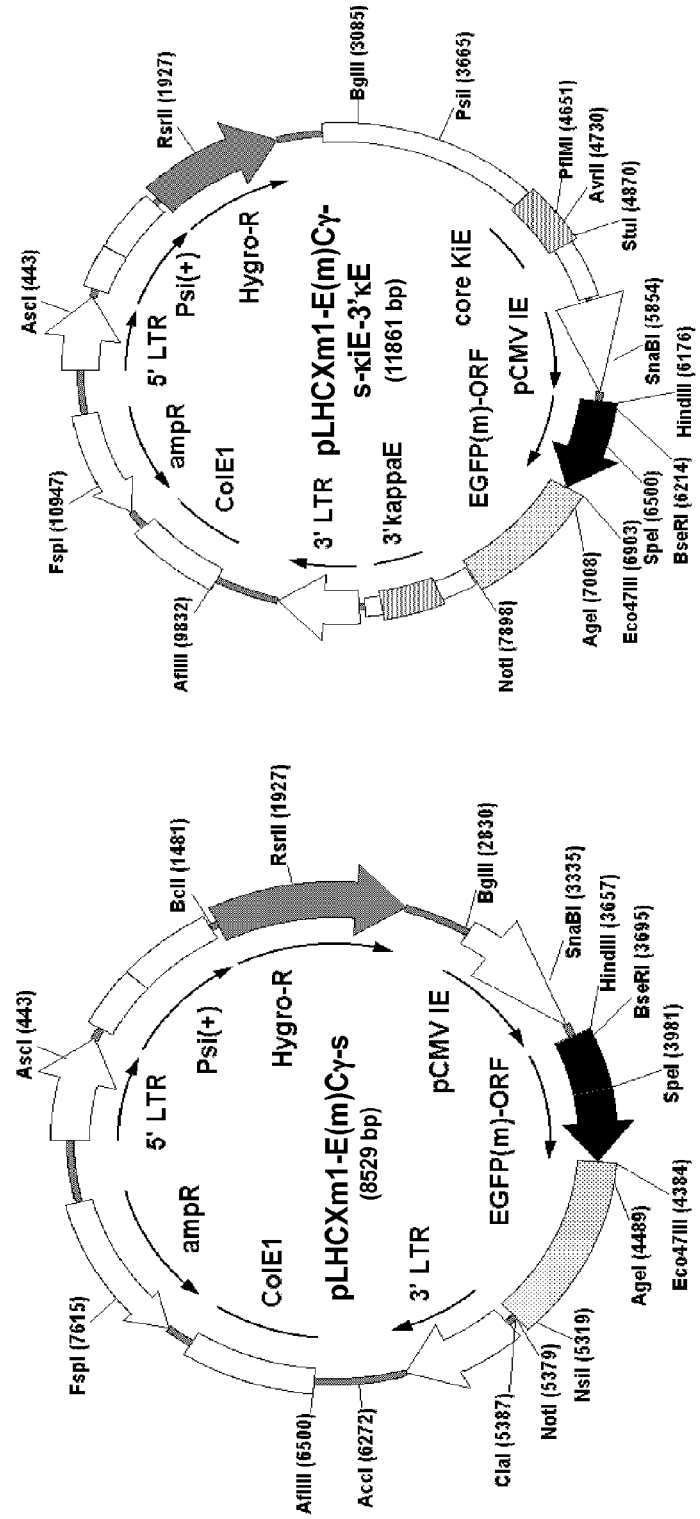

FIG. 8: This FIG. 8a and continued onto 8b) illustrates the detailed cloning strategy, also provided in Example 2, for a retroviral reporter constructs with and without IgκL chain enhancer elements, allowing the identification and quantitation of somatic mutations by reversion of a defined EGFP stop mutation.

Figure 9:
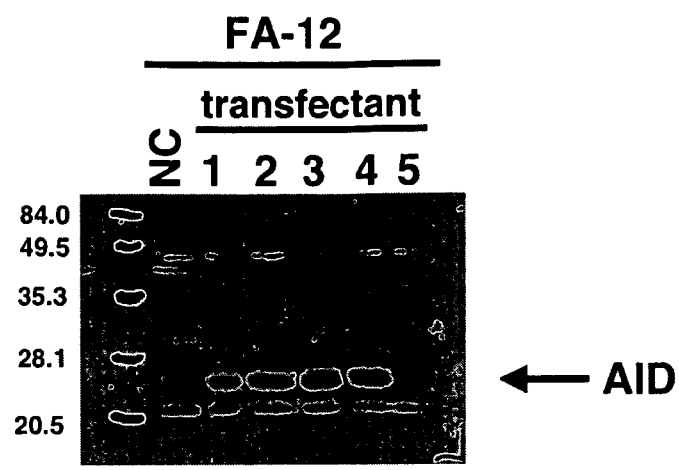
Figure 9:
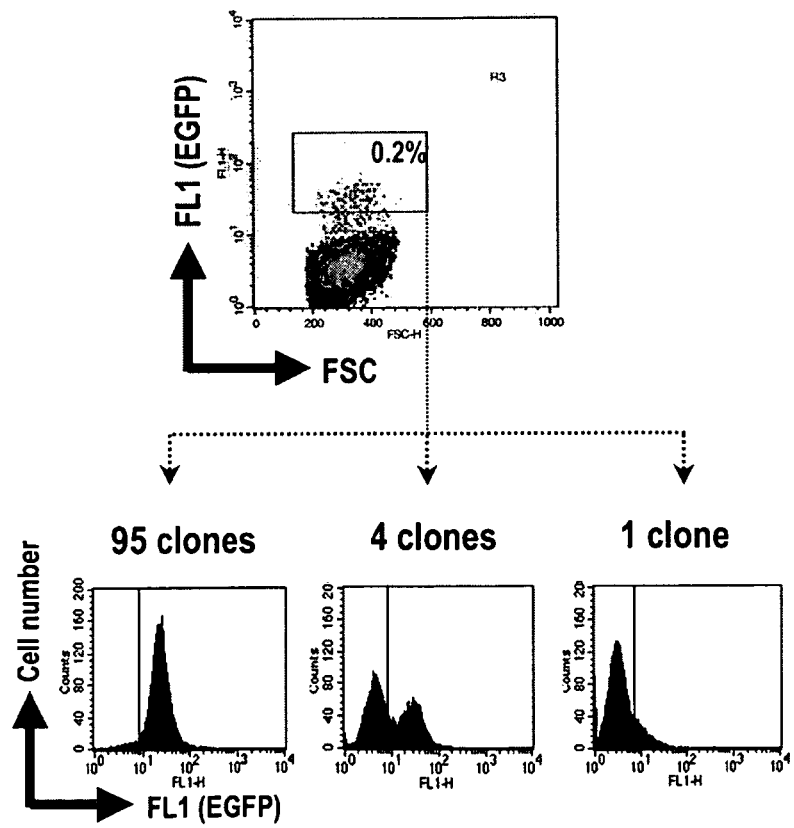

FIG. 9: This figure provides an experimental proof-of-concept that the disclosed retroviral vectors allow AID mediated somatic mutation of sequences, like preferably antibody V coding regions, cloned downstream of the V-promoter elements. Panel (a) shows an analysis of AID expression by Western-blotting of five selected FA-12 A-MuLV transformed cell clones that had been stably transfected with a retroviral AID expression construct, whose cloning was depicted in FIG. 7. The Western-blot analysis shows a distinct AID-specific signal of ca. 25 kD in FA-12 transfectant clones 1 through 4, but not in transfectant 5 and also not in the non-transfected negative control (NC). Transfectant 3 was used for further testing of retroviral reporter vectors for AID-mediated somatic hypermutation (SEM), which is depicted in panel (b): Here the retroviral reporter constructs of FIG. 8 (once with and once without Igκ enhancer elements) were retrovirally transduced into AID expressing and AID non-expressing FA-12 transfectants and 5, respectively. As expected, only when reporter constructs containing the enhancer elements were transduced into AID-expressing FA-12 transfectant clone 3, was it possible to detect green revertant transductants at a 0.2% frequency 10 days post transduction. From these 0.2% green cells, 100 individual cell clones were isolated by single cell sorting and these clones were re-analyzed for green fluorescence by FACS after expansion. The vast majority of the single cell sorted clones (95%) displayed homogeneous green fluorescence expression at the same fluorescence intensity as the medium green fluorescence signal of the 0.2% green cells originally sorted, and similar to the representative GFP expression pattern provided at the lower left panel of FIG. 9b, confirming that the original green population was due to reversions of the EGFP stop mutation. Four clones showed a bimodal green fluorescence pattern, as representatively depicted in the middle FACS histogram and only 1 of the 100 single cell sorted cloned displayed hardly any green fluorescence (right-hand FACS histogram).

FIG. 10: This figure illustrates the sequence of the EGFP coding region with an engineered stop mutation that was used to clone an EGFP reporter construct for quantitating somatic hypermutation. In panel (a) it is shown, which of the four nucleotides have been mutated in codon 107 and 108 of the wildtype EGFP open reading frame (see nucleic acid sequence ggcaactacaagacccgc (SEQ ID NO:34) which encodes amino acid sequence GNYKTR (SEQ ID NO:36)) thereby generating a stop-codon in codon 107 and generating a lysine to threonine amino acid change in codon 108 (see nucleic acid sequence ggcaactagtatacccgc (nucleotides 313-330 of SEQ ID NO:36). These four nucleotide changes additionally resulted in the introduction of unique SpeI restriction enzyme site, as indicated that could be used as a diagnostic marker for stop codon reversions upon somatic hypermutation. The G-nucleotide of the TAG stop codon is embedded in a so-called RGYW sequence motif, which is known to be a hotspot for somatic hypermutation. In 24 revertant clones analyzed by SpeI restriction enzyme digestion, it could be confirmed that the site was rendered resistant to SpeI digestion (and hence was mutated). In ten of these clones sequence analysis revealed that the G nucleotide in the original TAG stop-codon had been mutated to a C nucleotide, resulting in a TAC codon, thereby confirming the restriction enzyme analysis, and demonstrating that AID-mediated somatic mutation had been targeted to the G in the RGYW motif.

(b) This panel shows the entire ORF of the mutated EGFP that was cloned into the retroviral Igγ1H chain construct already disclosed in FIG. 5(e), instead of a $V_H$ domain coding region. The nucleic acid coding sequence, the N-terminal amino acid sequence, and the C-terminal amino acid sequence of the mutated EGFP are set forth in SEQ ID NO: 36, 37 and 38, respectively.

Figure 11A:
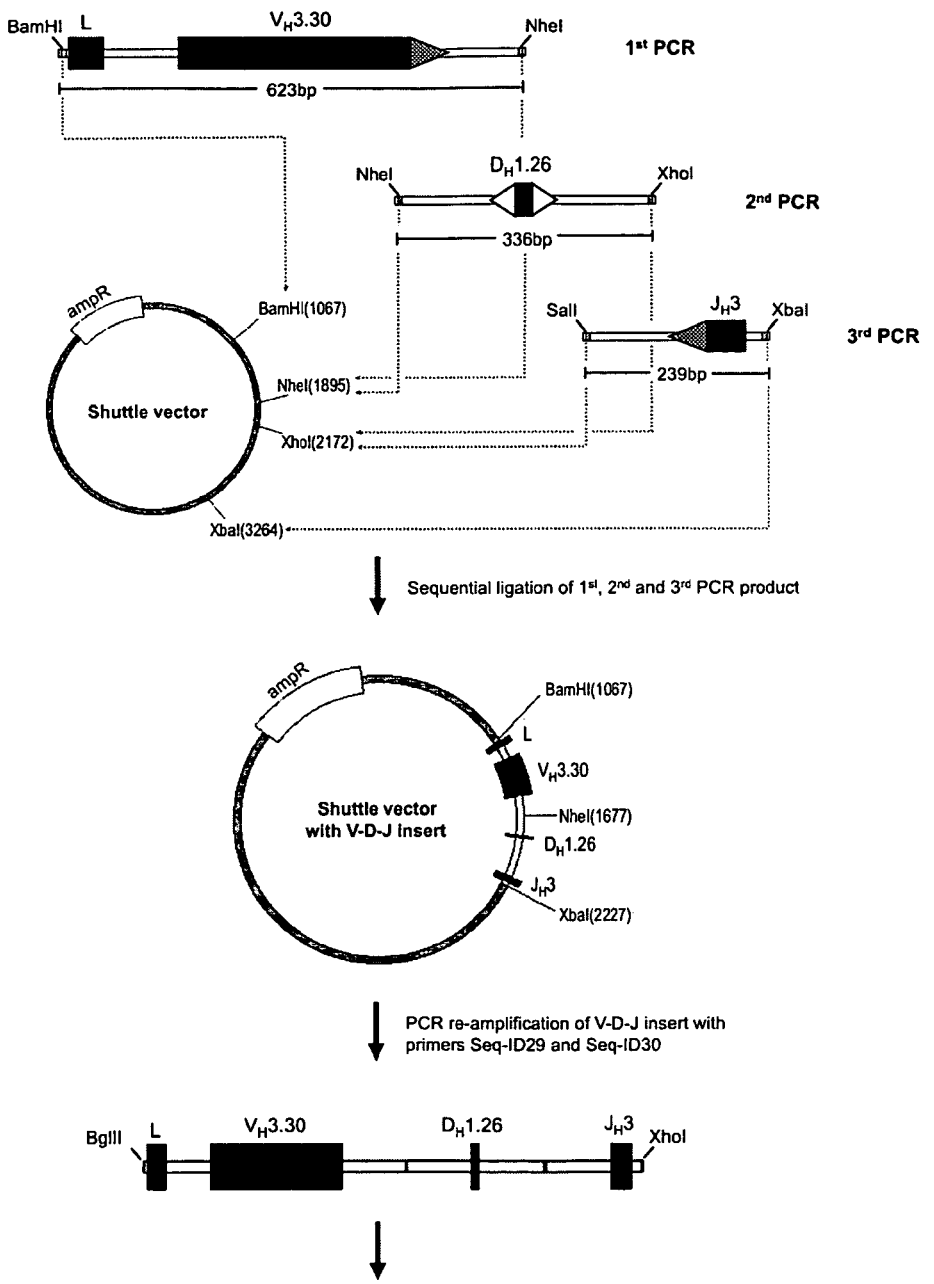

FIG. 11(a) and (b): Illustration of the detailed cloning strategy of a V(D)J recombination competent retroviral IgH chain expression vector, as disclosed in detail in Example 4.

Figure 11B:
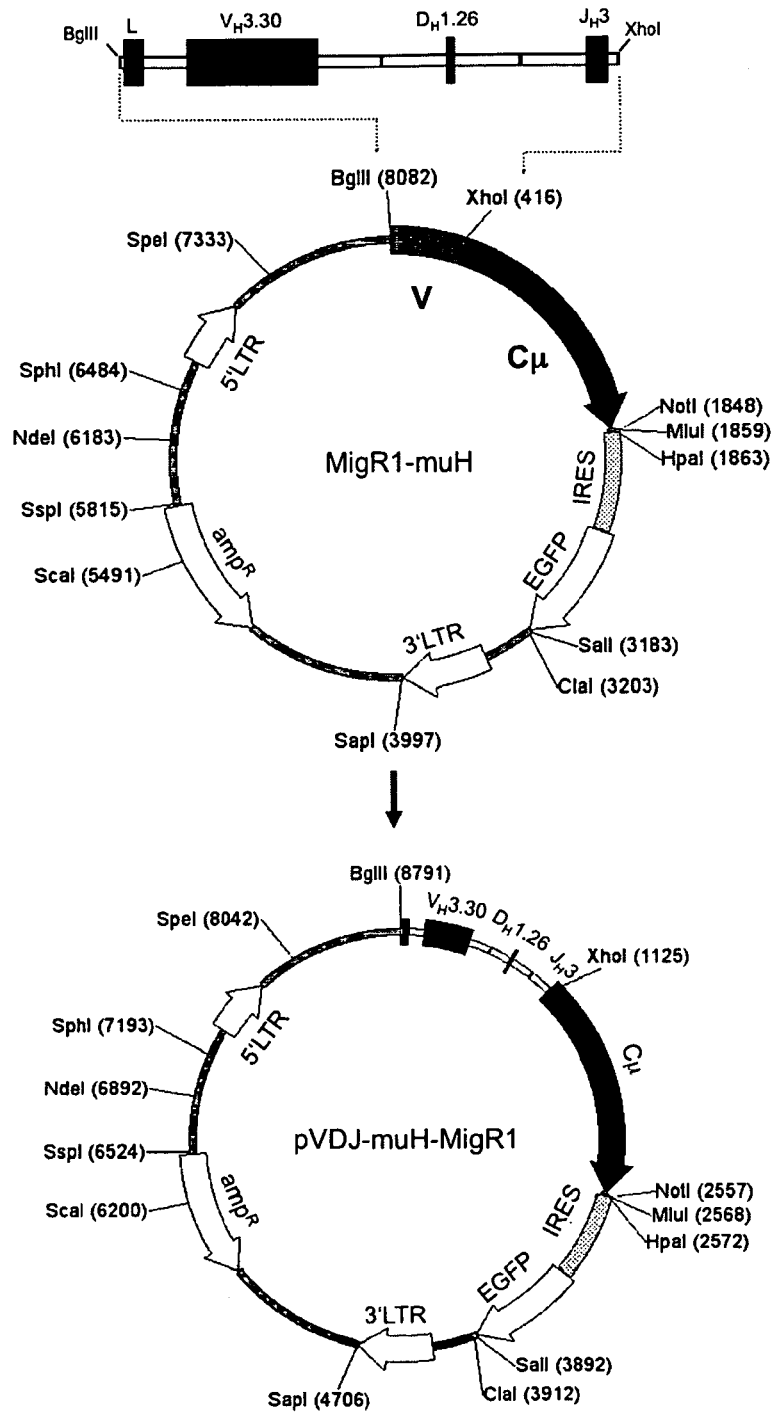
Figure 12:
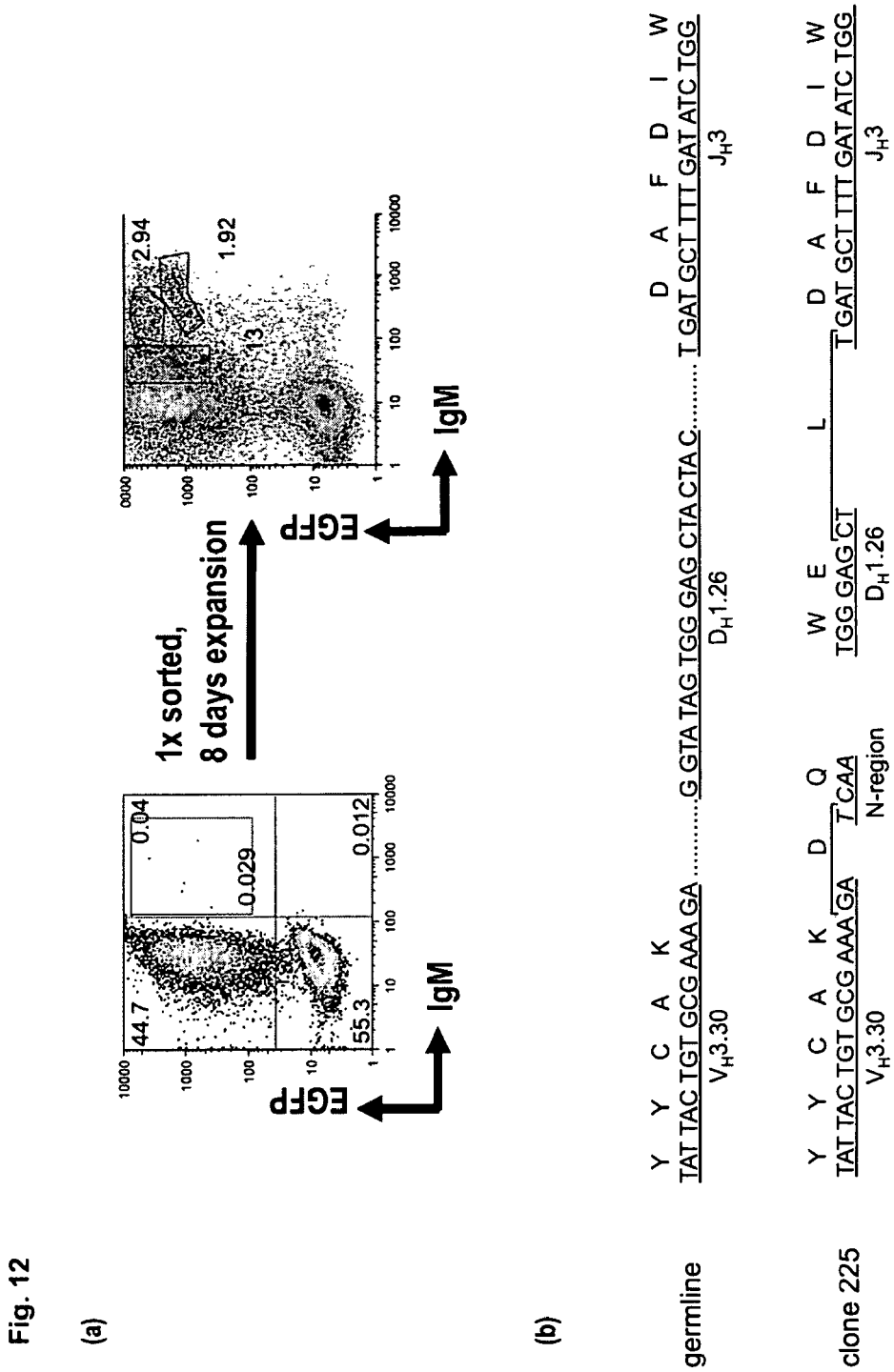

FIG. 12: Proof-of-concept that retroviral constructs requiring V(D)J recombination of V, D and J gene segments in "quasi-germline" configuration can give rise to productively rearranged heavy chain expression constructs and Ig+ cells upon transduction into RAG1/RAG2 positive precursor lymphocytes. Panel (a) contain data showing the generation of surface immunoglobulin positive cells (0.04%, upper right quadrant of left FACS plot) after transduction of a V(D)J recombination competent retroviral expression vector (detailed description of cloning, see FIG. 11) into A-MuLV transformed preB cell line 230-238. The immunoglobulin expression is coupled to EGFP expression using constructs as schematically illustrated in FIG. 4 c. Therefore, immunoglobulin expressing cells can only be generated in the population of green (i.e. stably transduced) cells. The right staining panel shows re-analysis of surface immunoglobulin expression after a single round of FACS enrichment and expansion of the rare (0.04%) surface immunoglobulin cells for 8 days in tissue culture. After this one round of enrichment, the combined frequency of immunoglobulin positive cells had increased to 17.8% (as expected detectable in the green, i.e. the stably transduced population) from which PCR amplicons have been obtained and sequenced. (b). As a representative example, this panel shows a DNA sequence (clone 225, with amino acid translation on top) obtained from a PCR amplicon derived from surface immunoglobulin cells after one round of enrichment that had been transduced with "quasi-germline" V(D)J recombination competent retroviral vectors. As a reference, the sequences of the coding regions of the V, D and J gene segments (SEQ ID NO: 39, 41, and 42 respectively) are provided in (b) at the top, also with amino acid translation on top of the V and J gene segments (SEQ ID NO: 40 and 43 respectively), as the D segment sequence can be read in three different reading frames, depending on the junctional diversity after V(D)J recombination. Intervening sequences between the V, D and J gene segments in "quasi-germline" configuration are depicted with dots. The sequence of recovered clone 225 clearly represents a bona fide V(D)J rearrangement event, with typical features of nucleotide loss and TdT catalyzed N-sequence additions clearly detectable at the coding joints between the assembled V, D and J gene segments (all intervening sequences had been lost from clone 225). The sequence of clone 225 exhibited an open reading frame and, apart from the aforementioned variations at the coding junctions, did not contain additional somatic mutations in the V, D and J sequences Amino acid sequences YYCAKDQ and WELDAFDIW are set forth in SEQ ID NO: 45 and 47 respectively. Nucleic acid sequences tattactgtgcgaaagatcaa and tgg-gagcttgatgattttgatatctgg are set forth in SEQ ID NO: 44 and 46 respectively.

Figure 13:
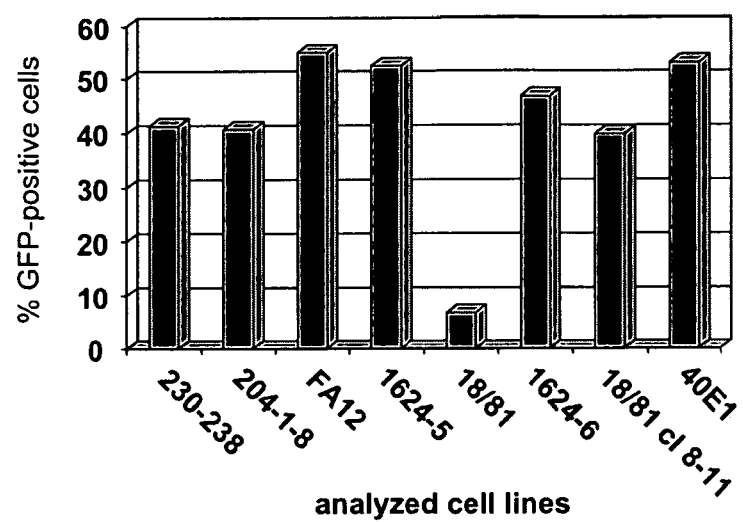

FIG. 13: Data showing the testing of a panel of different A-MuLV transformed murine preB cell lines for the susceptibility to ecotropic MLV-derived vector gene transfer. $1 \times 10^5$ cells were transduced with a MOI of 0.5 using a vector preparation having packaged the reporter gene EGFP encompassing transfer vector LEGFP-N1. Transduction was carried out as detailed in Example 5. Two days post transduction, gene transfer was detected by expression of EGFP using FACS. Except for preB cell line 18/81, all other tested A-MuLV transformed preB cell lines were susceptible for transduction at frequencies ranging between 40-60% under the applied conditions, and can, in principle, be used for the current invention. Untreated naïve target cells served as negative controls and showed no green fluorescence (not shown).

Figure 14:
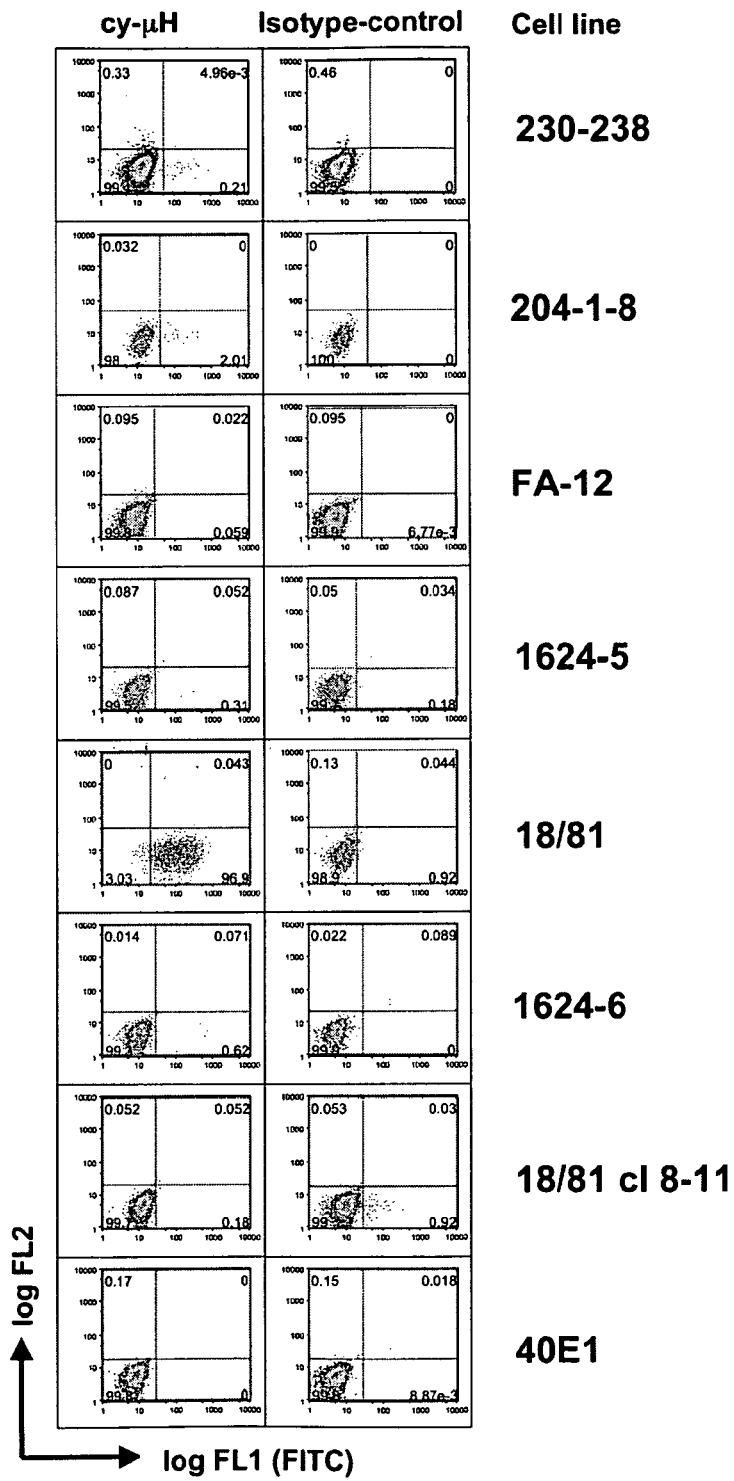

FIG. 14: Characterization of a panel of murine preB cell lines for intracellular expression of endogenous IgM heavy chains (cy-μH), in order to identify cells devoid of endogenous murine antibody expression that can be used as selector cells for retrocyte display. Cells were permeabilised and stained using anti-murine IgM heavy chain antibodies coupled to FITC (FL1). Untreated cells served as negative controls. The experiment shows that cell lines FA-12, 1624-5, 1624-6, 18/81-c18-11, and 40E1 had practically undetectable endogenous antibody expression, and can thus be used in a method of the present invention.

Figure 15:
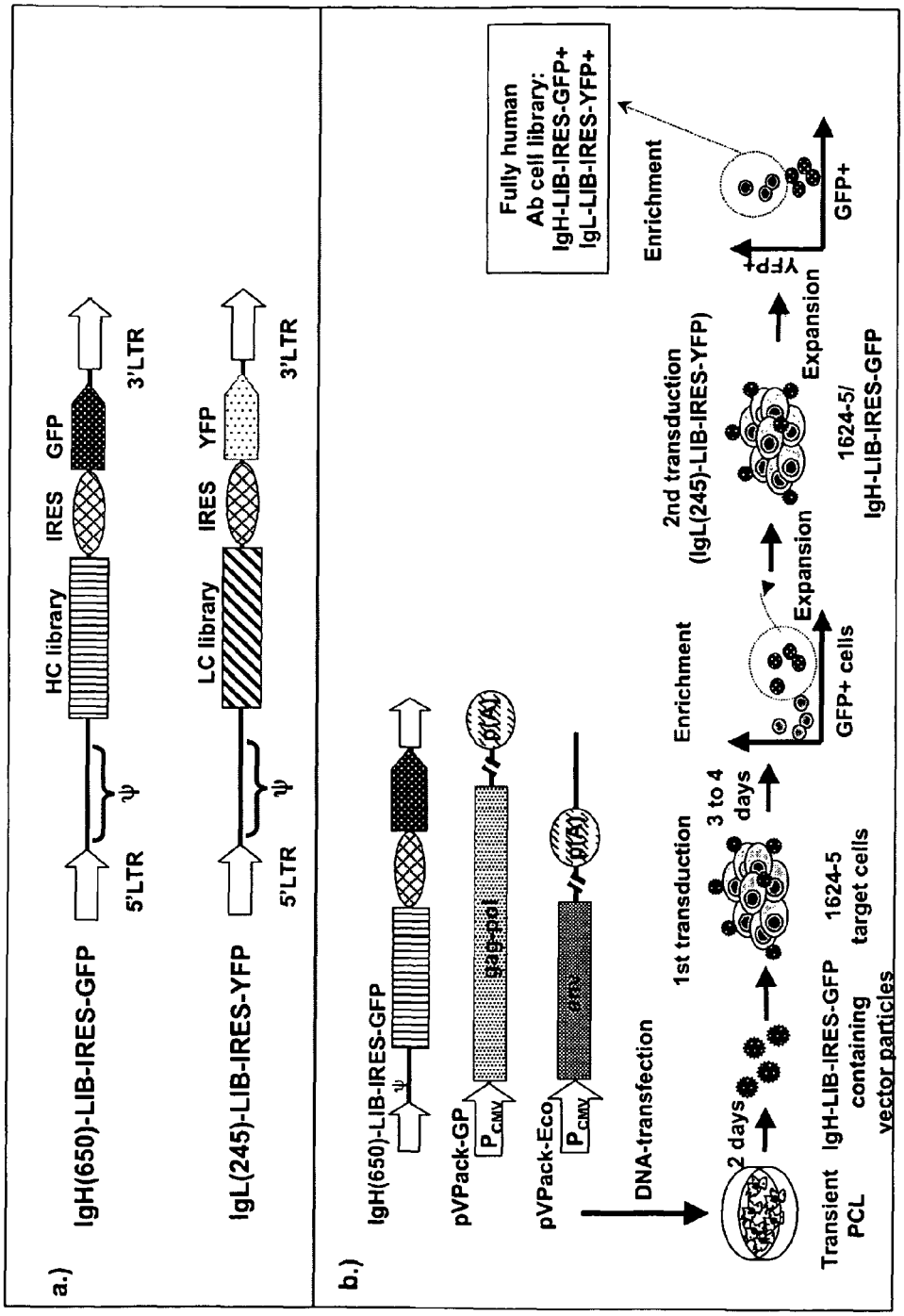

FIG. 15: Illustration of the complexity of retroviral expression vectors following the design disclosed in FIG. 4(c) and the experimental principle for the generation of a IgH and IgL chain shuffled antibody library. (a) The retroviral vector libraries IgH(650)-LIB-IRES-GFP and IgL(245)-LIB-IRES-YFP encompass defined collections of coding regions for heavy (HC) and light chains (LC) for fully human antibodies with a complexity of 650 and 245 different, fully sequenced clones, respectively. Both vectors harbour the packaging sequence Psi (ψ), flanking long terminal repeats (LTR) and an internal ribosome entry signal (IRES). Parallel to the expression of an antibody polypeptide chain mediated by the viral promoter in the 5'LTR, the IRES enables the coupled expression of the reporter gene gfp and yfp, respectively. Upon viral gene transfer into selector cells, this allows for the convenient detection and enrichment of successfully transduced and immunoglobulin chain expressing cells using FACS.

(b) Generation of a collection of fully human antibodies in transformed preB cells. In order to generate transient packaging cells, libraries of retroviral transfer vector libraries encoding heavy chains of human antibodies (IgH(650)-LIB-IRES-GFP) are co-transfected with a packaging construct (pVPack-GP) and an envelope construct (pVPack-Eco) into suitable recipient cells. Two days post transfection, the generated vector particles library having packaged the respective transfer vector library are harvested and employed to transduce selector pre B cells. Transduced cells expressing the transferred heavy chains and the reporter gene gfp are expanded enriched using FACS. Following expansion, cells are subjected to a second transduction. This time, the IgL (245)-LIB-IRES-YFP library is transferred followed by expansion and enrichment of cells expressing YFP and human light chains employing FACS. The resultant population constitutes a fully human antibody displaying a defined human antibody library expressed by 1624-5 cells, containing a complexity of maximally 159'250 clones.

Figure 16:
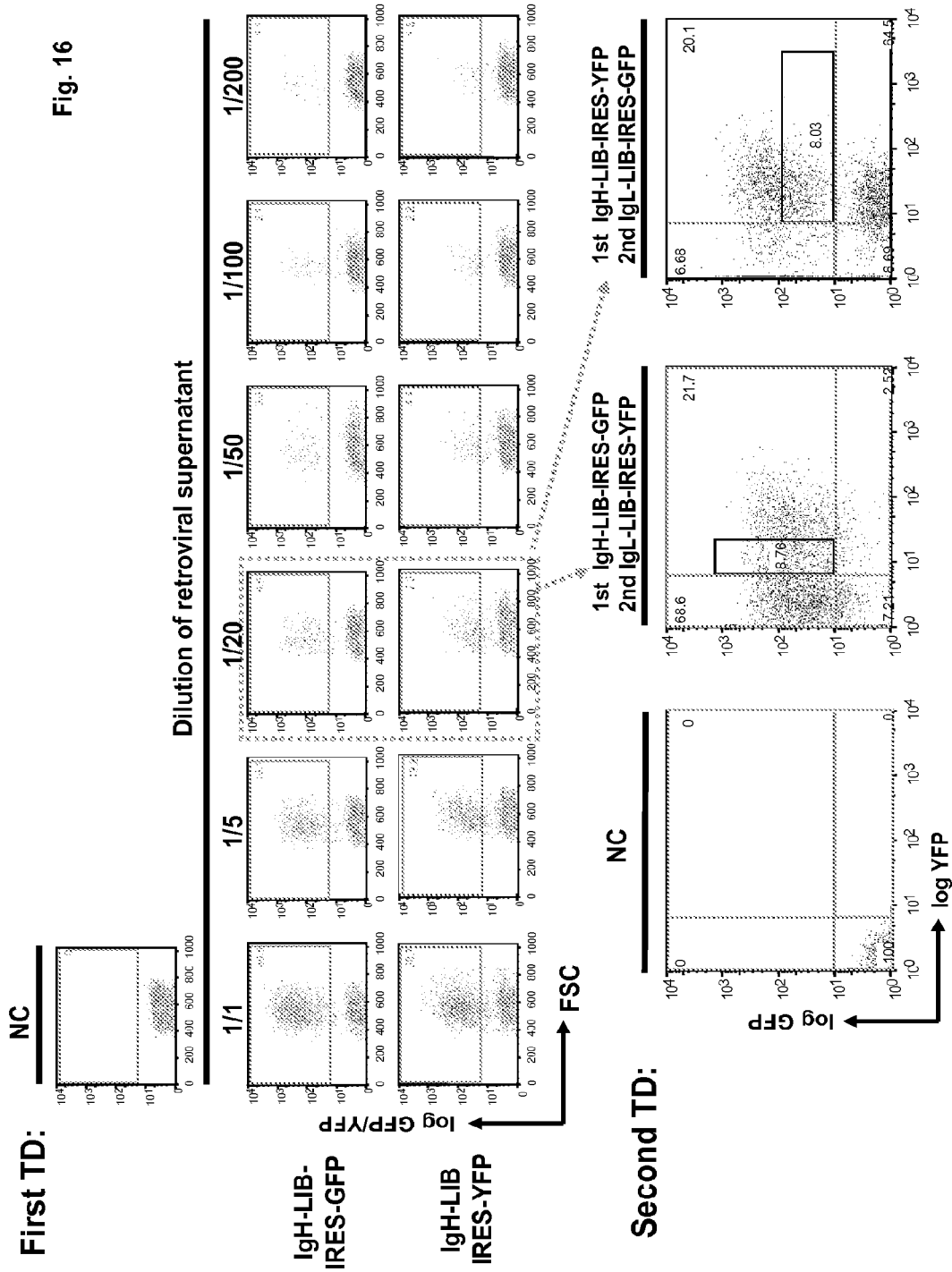

FIG. 16: This figure shows how a two-step transduction with IgH-IRES-GFP and IgL-IRES-YFP libraries has been performed at conditions ensuring a transduction, resulting in clonal expression of polypeptide chains in the vast majority of the transduced cells. $1.5 \times 10^6$ 1624-5 murine A-MulV transformed preB cells were suspended in 1 ml of tissue culture medium supplemented with different quantities of vector particle supernatant (diluted 1:1; 1:5; 1:20; 1:50; 1:100; 1:200) containing recombinant retroviral vectors encoding IgH and IgL chain libraries IgH-LIB-IRES-GFP or IgL-LIB-IRES-YFP, respectively, already described in FIG. 15. To ensure that the majority of the transduced cells received single copies of transfer vectors integrated into the host cell genome, cells displaying gene transfer efficiencies lower than 10% (MOI<0.1, as detected by expression of the coupled GFP or YFP reporters) were enriched using FACS sorting four days post infection. Cells were expanded for six days and subjected to a second transduction employing vector particles having packaged the light chain coding regions of antibodies at a dilution of 1:5 as described above. Here, GFP-positive cells selected for heavy chain expression were infected with vector particles transducing the IgL-LIB-IRES-YFP library and vice versa. Four days post infection, transduced cells expressing GFP and YFP were enriched using FACS. Approximately 20% of the cells showed GFP and YFP expression after the second transduction. To secure that only single vector integrations occurred per cell about one third of the populations were enriched that revealed only low or moderate expression of the reporter gene transduced in the second round (approximately 8%).

Figure 17:
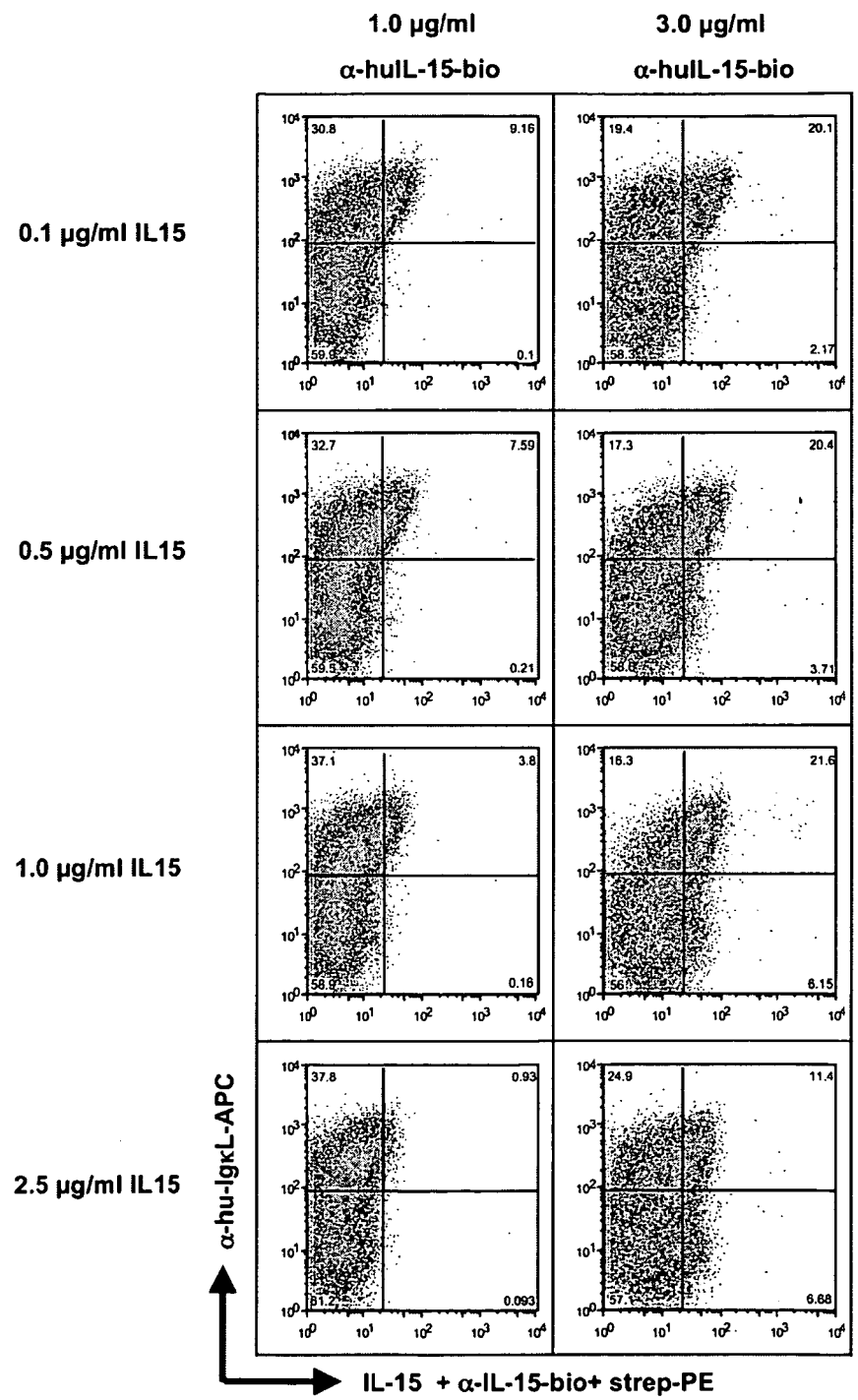

FIG. 17: Titration of IL-15 staining with a population of preB cells expressing an anti-IL-15 reference antibody by FACS, in order to define optimal conditions allowing optimal IL-15 antigen staining conditions for Retrocyte Display experiments. The staining procedure, as disclosed in detail in Example 7, included a titration of the IL-15 antigen in the range of 2.5 μg/ml-0.1 μg/ml, at two different concentrations of a polyclonal, biotinylated anti-IL-15 secondary antibody, as indicated, which was detected with streptavidin-PE conjugate by FACS. Surface Ig+ cells were counterstained with an anti-IgκL chain-APC antibody. As can be seen, optimal IL-15 staining is accomplished at a concentration of 0.1 or 0.5 μg/ml IL-15 antigen, and using 3 μg/ml of the secondary, polyclonal anti-IL-15 antibody.

Figure 18:
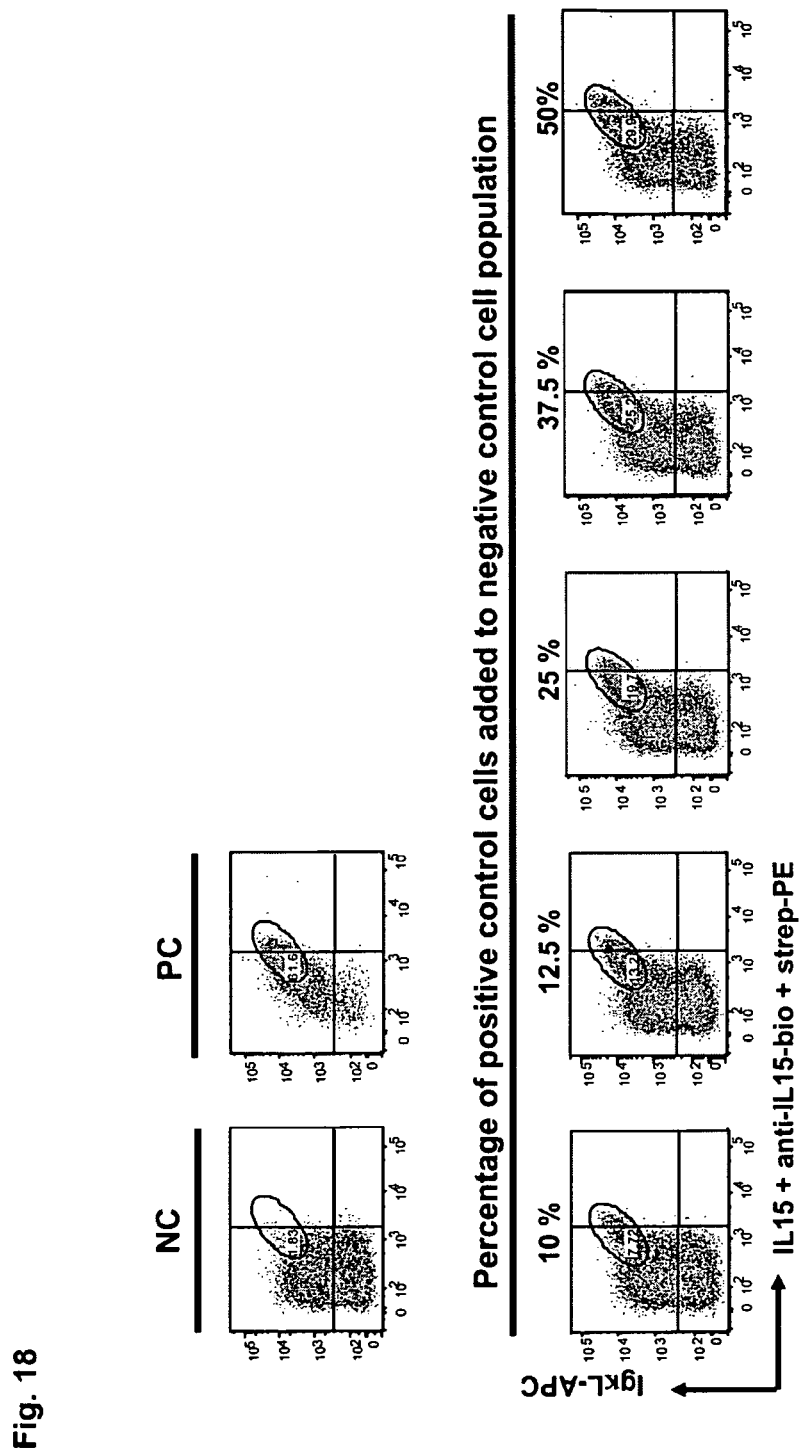

FIG. 18: Analysis of FACS-identification of an anti-IL-15 reference antibody expressing preB cell line (PC=positive control), which was spiked into a diverse library of antibody expressing preB cells at different dilutions, by using the optimized IL-15 staining conditions illustrated and determined in FIG. 17. The top-left panel shows the IgκL chain-APC/IL-15 double staining of control preB cells transduced with a combination of IgH and IgL chain libraries, whose generation was already shown in FIG. 16 (NC=negative control). The top right panel shows the IgκL chain-APC/IL-15 double staining of preB cells transduced with retroviral expression vectors encoding IgH and IgL chains of a reference IL-15 antibody (PC=positive control), as disclosed in detail in Example 7. The FACS profile of the NC cells shows that approximately 50% of the Ab-library transduced cells are surface-Ig+, as detected by the anti-IgκL chain-APC staining. However, none of the surface-Ig+ cells displays binding to IL-15. In contrast, the PC cells, in which more than 90% of the cells expressed surface Ig a specific IL-15-antigen binding is apparent by a specific signal on the x-axis. As expected, the higher the expression of surface-Ig on the PC cells, the more pronounced the shift for the specific IL-15 signal, resulting in a diagonal staining pattern of surface-Ig+/IL-15 binding cells, which is highlighted by a elipse-shaped gate, as indicated. The panel on the bottom, showing double-FACS stainings for surface-Ig and IL-15-binding in five different dilutions of PC cells spiked into the NC random antibody library expressing cell population shows that a specific anti-IL-15 reference antibody expressing PC cells can be detected at frequencies close to the percentage of PC cells spiked into the NC cell library.

Figure 19:
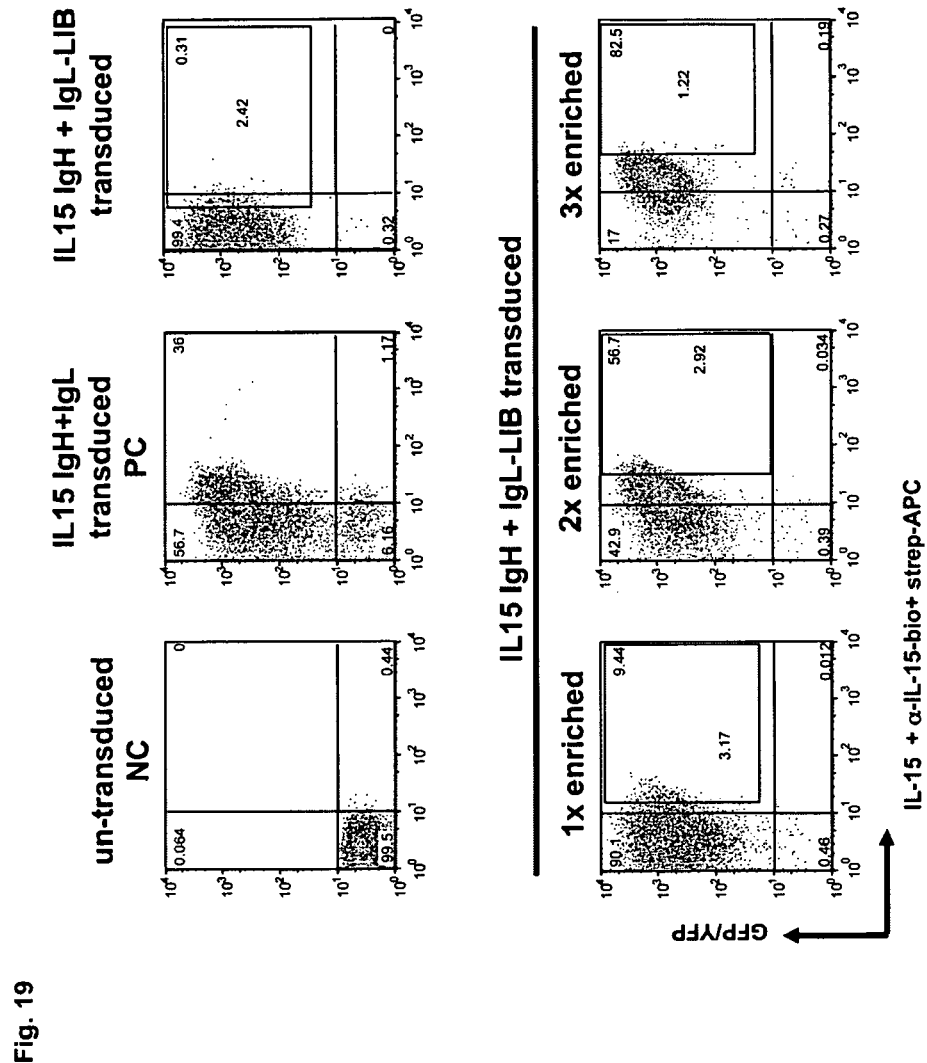

FIG. 19: Proof of concept for the enrichment of a IL-15-reactive cell population by Retrocyte Display from a diverse antibody library, as disclosed in detail in Example 7. The top panel shows FACS stainings for GFP/YFP expression (y-axis), indicative of the frequency of Ig-retrovector transduced cells, and IL-15/anti-IL-15-bio α-axis), indicative of specific IL-15 staining. The top-left panel shows the two-colour FACS analysis of untransduced control preB cells (NC=negative control), the top-middle panel shows the two-colour FACS analysis of preB cells transduced with an anti-IL-15 reference antibody as a positive control (PC). The top-right panel shows the same two-colour FACS staining of a population of cells that have been transduced with a single IgH chain encoding retroviral vector encoding the IgH chain of the reference anti-IL15 antibody in combination with a diverse, $>7 \times 10^4$ different IgκL chain library. This IgL chain shuffled library therefore contains potentially $>7 \times 10^4$ different antibodies, and expectedly, even by very narrow gating for antibody-expressing and IL-15 reactive cells, as indicated in the top-right FACS-profile, very few IL-15 reactive cells could be detected (here 2.42%, due to the gating close to the negative population, as indicated). The enriched population was expanded in tissue culture, and the identical staining procedure and FACS-sorting was repeated three times, as shown for the three FACS stainings under identical conditions in the lower three FACS panels. As can be seen, consecutive enrichment/cell expansion cycles resulted in a population of cells that was almost 100% positive for antibody expression and even more positive for IL-15-reactivity than the original PC cell line. This data shows clearly that by repeated FACS sorting and expansion a highly antigen-reactive cell population can be successfully enriched to an essentially 100% antigen-reactive cell population from almost undetectable antigen-reactive cell populations using three consecutive rounds of Retrocyte Display.

Figure 20:
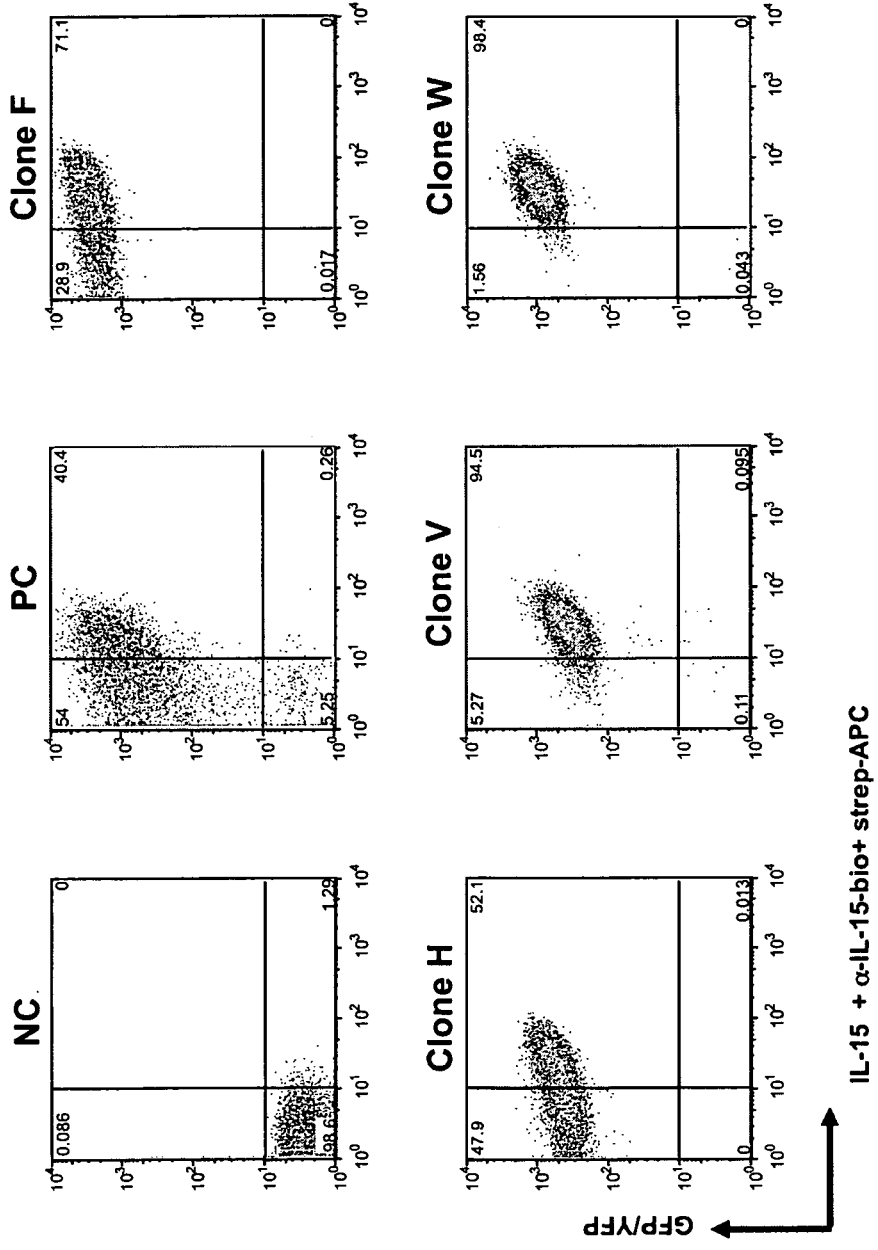

FIG. 20: This figure illustrates and confirms the specific IL-antigen reactivity of 4 representatives of 24 individual cell clones established after single cell sorting from a 3 times IL-15 antigen enriched cell population, as described in FIG. 19. The 4 selected cell clones are designated clone F, H, V and W, and all show specific IL-15 reactivity on GFP/YFP positive cells, indicative of the stably transduced, Ig encoding retroviral vectors. As expected, higher GFP/YFP expressing cells, expressing higher antibody levels showed higher IL-15 specificity, leading to characteristic diagonal staining signals in the Ig/IL-15 double stainings. All cell clones showed specific IL-15 reactivity, as demonstrated by omission of the IL-15 antigen in the stainings, which led to a loss of IL-15-specific reactivity (not shown). The data provide proof of concept that Retrocyte Display is an efficient method to obtain antigen-reactive cell clones at high frequencies from cell populations initially showing almost undetectable antigen-reactive cells.

Figure 21:
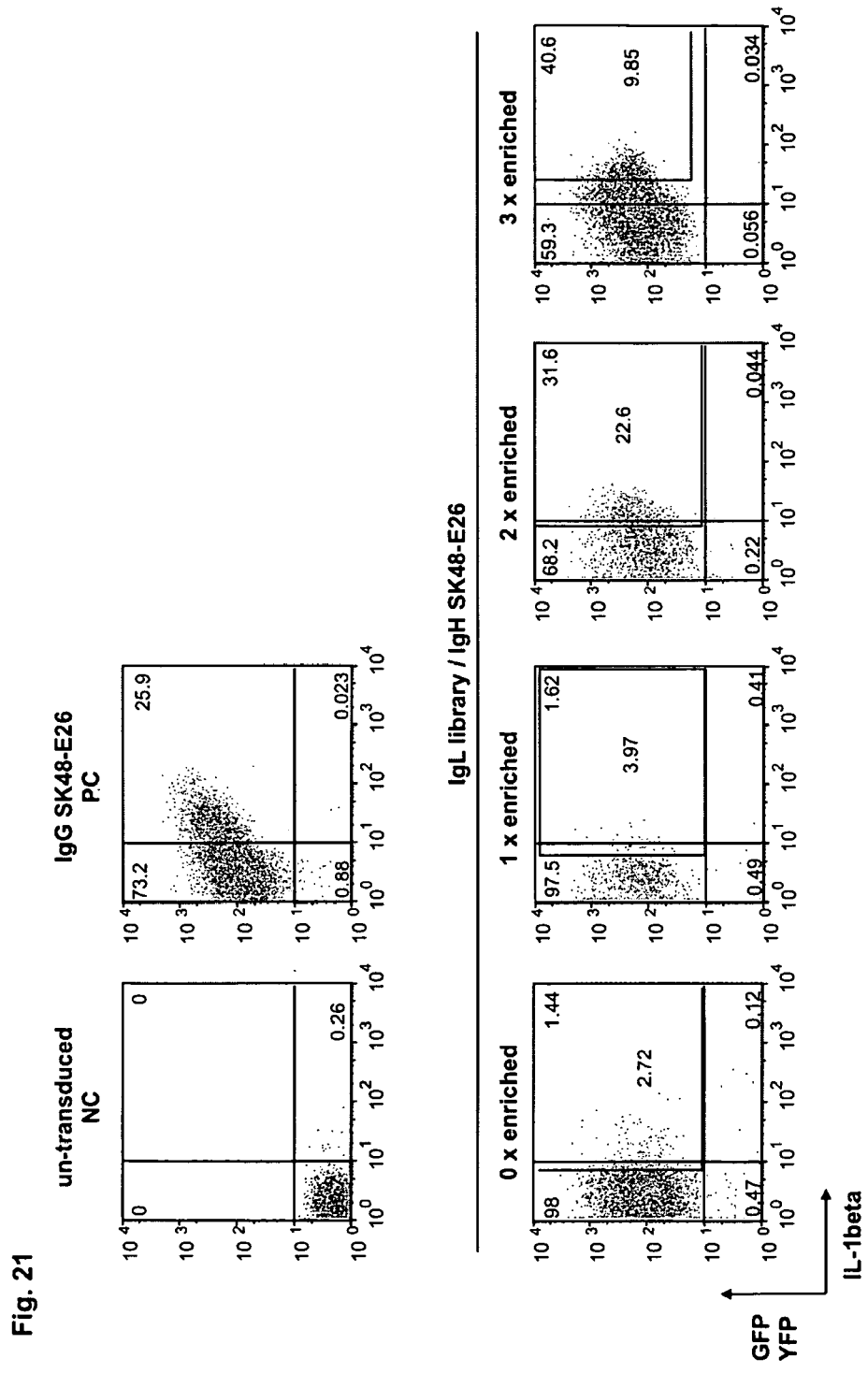

FIG. 21: This figure provides a second proof of concept for successful Retrocyte Display enrichments of antigen-reactive cells by illustrating the successful enrichment of IL-1β antigen-reactive cells to an essentially 40% antigen-reactive cell population using three consecutive rounds of retrocyte display cell enrichment/tissue culture expansion, starting from a minimally IL-1beta-reactive cell population in the initial cell population. Double stainings for GFP/YFP expression (indicative of antibody expression) and IL-1β reactivity are provided. FACS stainings on top are provided for non-transduced preB selector cells (as negative control =NC, top-left) and cells co-transduced with retroviral vectors encoding an anti human IL-1β specific reference antibody SK48-E26 (as positive control=PC, top right), as indicated. The bottom panels show the FACS stainings for antibody expression and IL-1β reactivity of an antibody library generated by shuffling of a diverse IgL chain library of >1.2×10$^5$ individual IgL chain clones against the IgH chain of the SK48-E26 reference antibody, before (0× enriched) and after 1, 2 and 3 Retrocyte Display enrichment rounds, as indicated and as disclosed in detail in Example 8. These data provide an independent proof of concept using a second antigen that Retrocyte Display expression and enrichment is a powerful means to enrich a population of antigen-specific cells from initially almost undetectable levels.

Figure 22:
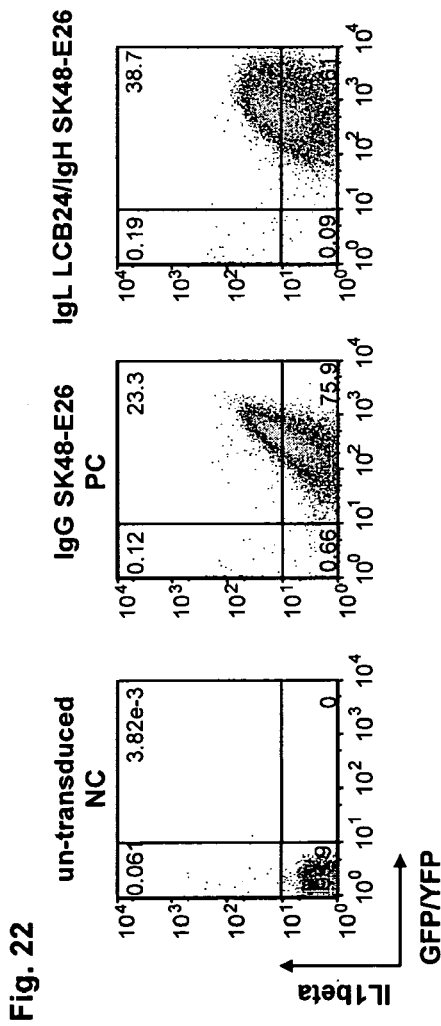

FIG. 22: This figure shows confirmation of IL-1β antigen reactivity of a novel antibody identified by Retrocyte Display, as disclosed in detail in Example 8. From the 3× enriched cell population, shown in FIG. 21, 24 individual cell clones have been established by single cell sorting. From these 24 cell clones, 12 clones harboured a novel IgL chain, termed LCB24, as disclosed in Example 8. The IL-1β specificity of the novel LCB24 IgκL chain co-expressed with the IgH chain of the IL-1β specific reference antibody SK48-E26 (see Example 8) was analyzed by FACS upon re-transduction of the cloned and sequence characterized IgL and IgH chain retroviral expression vectors into the original selector cell line. The FACS stainings show analysis of antibody expression (via GFP/YFP) and IL-1β reactivity by two colour FACS, as indicated. As expected no IL-1β reactivity is detected in non-transduced selector cells (NC=negative control, left), whereas a clear IL-1β specific staining is detected in positive control cells expressing IgH and IgL chains of reference antibody SK48-E26 (middle). A similar, IL-1β specific, signal is detectable in antibody expressing selector cells transduced with the SK48-E26 reference antibody IgH chain vector and the novel, fully human LCB24 IgκL chain, cloned from IL-1β specific Retrocyte Display cell clones (right).

Figure 23:
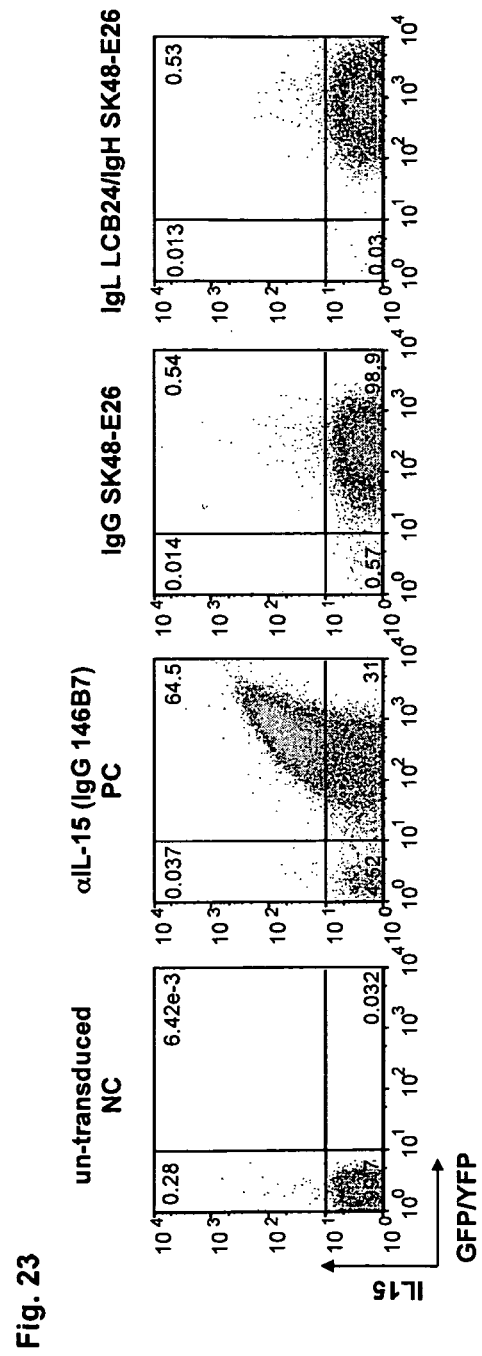

FIG. 23: Confirmation of lack of cross-reactivity to IL-15 of novel antibody encoded by LCB24 IgkL chain/SK48-E25 IgH chain. The two left FACS stainings show negative and positive controls for the IL-15 FACS staining assay, as indicated (NC=negative control, untransduced selector cells, PC=positive control, selector cells transduced with IgH and IgL chain vectors encoding an anti-IL-15 reference antibody). The two right FACS stainings show no IL-15 reactivity on antibody expressing cells either encoding the novel antibody composed of SK48-E26 IgH and LCB24 IgL chain, or on cells expressing the original SK48-E26 IgH/IgL combination. This demonstrates that the novel antibody composed of SK48-E26 IgH and LCB24 IgL chain is not only specific for IL-1β, but that it is not generally cross-reactive (or sticky) to other proteins, like IL-15.

Figure 24:
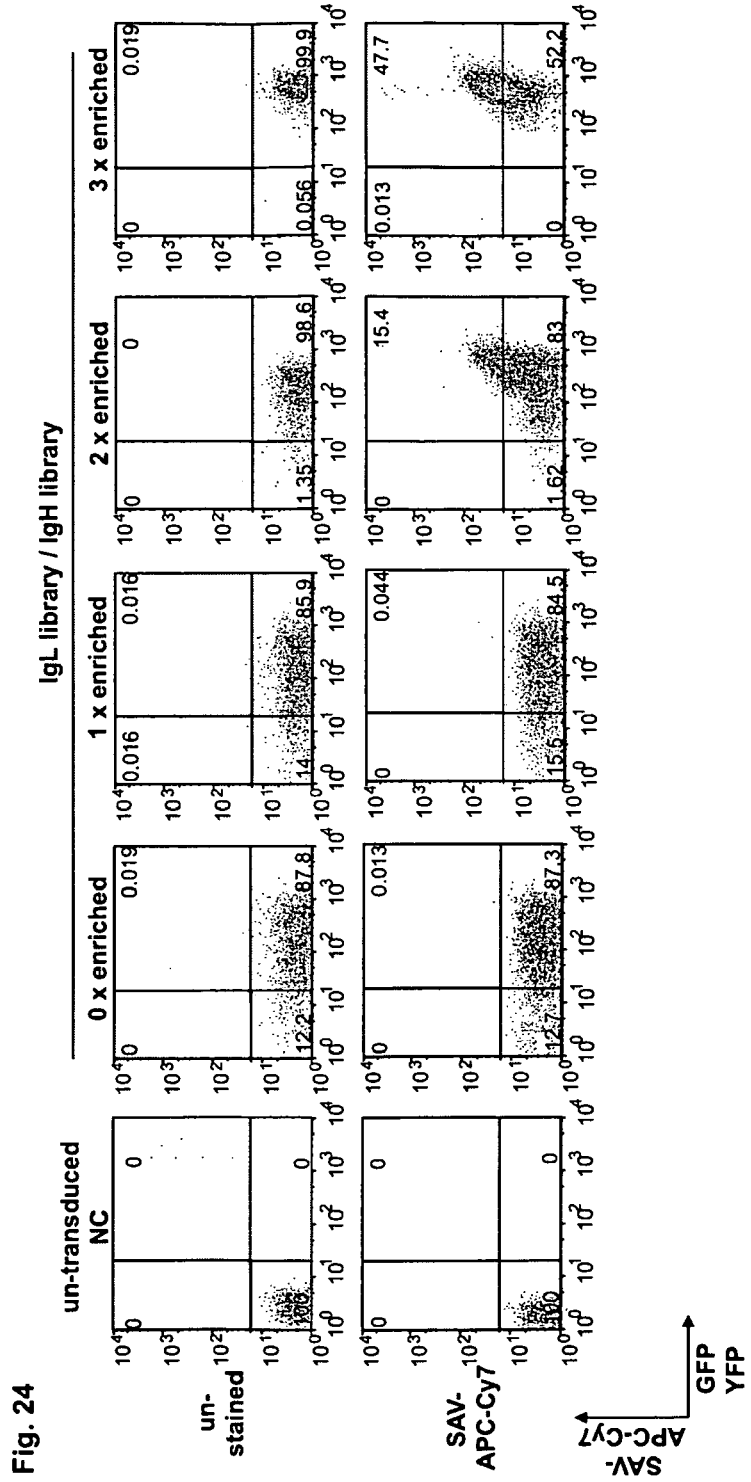

FIG. 24: This figure illustrates the successful enrichment of streptavidin-APC-Cy7 antigen-reactive cells by three consecutive rounds of Retrocyte Display cell enrichment/tissue culture expansion, from an antibody library generated by shuffling of a diverse IgL with a diverse IgH chain library as disclosed in Example 9. Streptavidin-APC-Cy7 reactive cells were enriched by three consecutive rounds of high-speed cell sorting, followed by cell culture expansion, as indicated. The binding-specificity of antibody expressing cells for the streptavidin-APC-Cy7 antigen is demonstrated by analyzing FACS profiles of the sequentially enriched cell populations in the presence (lower panel) and absence (top panel) of the antigen. This demonstrates a proof of concept for the efficient enrichment of antigen-specific by Retrocyte Display in the absence of any reference antibody that could be used for chain shuffling approaches.

Figure 25:
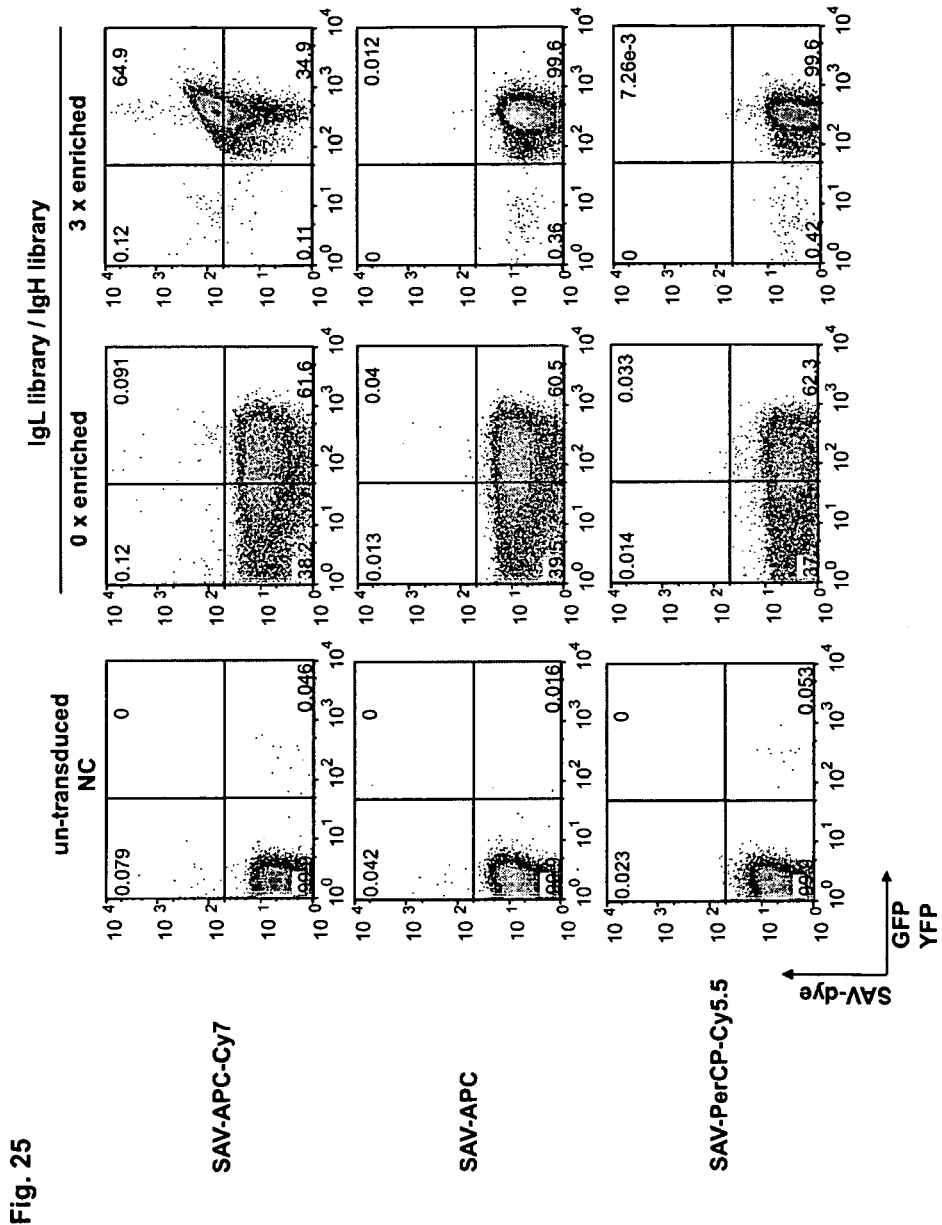

FIG. 25: The data presented in this figure provide evidence for the specificity of the 3 times Retrocyte Display enriched cell population disclosed in FIG. 24 for specific reactivity to the Cy7 fluorochrome of the strepatavidin-APC-Cy7 tandem dye. For this, non-transduced selector cells, unenriched cells expressing an IgH/IgL chain library combination and a 3 times strepatavidin-APC-Cy7 enriched cell population were analyzed by FACS for antibody expression (indicated by GFP/YFP fluorescence) and reactivity to different streptavidin-fluorochrome conjugates, as indicated. The 3 times streptavidin-APC-Cy7 enriched cell population only bound to streptavidin-APC-Cy7, but not to streptavidin-APC or streptavidin-APC-Cy5.5, and non-specific staining of strepatavidin-APC-Cy7 was also not detectable to either the selector cells or the selector cells expressing a diverse antibody library. This provides proof of concept for the efficient and highly specific Retrocyte Display enrichment of specific antibodies from cells expressing a diverse antibody library, without the need of antibody IgH or IgL chains from antigen-specific reference antibodies.

Figure 26:
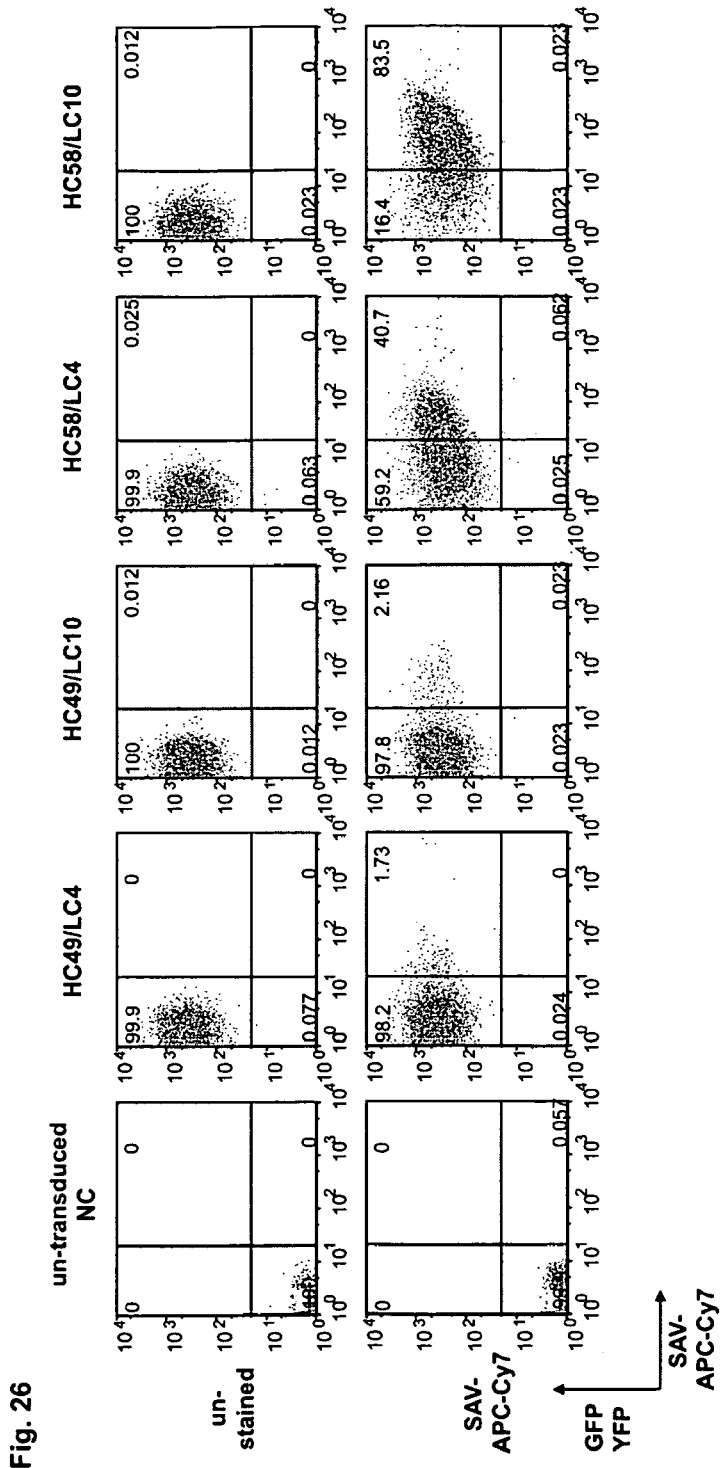

FIG. 26: Two novel human antibodies identified by Retrocyte Display, sharing the same IgH chain show specific binding to antigen streptavidin-APC-Cy7. As disclosed in Example 9, two different IgH chain sequences (HC49 and HC58) and two different IgL chain sequences (LC4 and LC10) could be identified from single-sorted cell clones after three rounds of Retrocyte Display enrichment. In this figure, all possible pairings of IgL chains LC4 and LC10 with HC49 and HC58 were examined for reactivity to the target antigen streptavidin-APC-Cy7. For this, combinations of retroviral expression vectors encoding the different IgH and IgL chains were transduced into selector cells as indicated and as disclosed in Example 9. As illustrated, novel antibodies HC58/LC4 and HC58/LC10, both sharing the same IgH chain, displayed specific binding to the streptavidin-APC-Cy7 antigen, whereas antibodies encoded by HC49/LC4 and HC49/LC10 did not show significant binding activity. The specific binding of the two novel antibody clones to the antigen streptavidin-APC-Cy7 upon re-transduction into selector cells provides conclusive evidence that it is possible to use Retrocyte Display as disclosed herein for the identification of rare antibody binders in complex antibody libraries.

TERMINOLOGY

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Affinity maturation: A highly regulated immunological process of antigen-driven improvement of the binding specificities of antibodies produced by antigen-stimulated B lymphocytes, mostly occurring in germinal centers. The process is caused by somatic hypermutation largely targeted to the coding regions for the variable domains of antibodies coupled with the selective expansion and survival of B lymphocytes generating higher affinity antibodies.

Antibody: This term describes an immunoglobulin whether natural or partly or wholly synthetically produced. The term also covers any polypeptide or protein comprising an antibody antigen-binding site, like heavy chain only antibodies from for example camels or lamas. A full-length antibody comprises two identical heavy (H) chains and two identical light (L) chains. In its monomeric form, two IgH and two IgL chains assemble into a symmetric Y shaped disulphide linked antibody molecule that has two binding domains formed by the combination of the variable regions of IgH and IgL chains.

Antibodies can be isolated or obtained by purification from natural sources, or else obtained by genetic engineering, recombinant expression or by chemical synthesis, and they can then contain amino acids not encoded by germline immunoglobulin genes. A fully human antibody comprises human heavy and light chains i.e. variable and constant domains from the human species. A chimeric antibody comprises variable region domains from one vertebrate species combined with constant region domains of another vertebrate species. The constant domains of a chimeric antibody are usually derived from a human antibody or antibodies. Humanised antibodies can be produced by grafting CDRs of non-human antibodies onto framework regions of IgH and IgL variable domains of human origin.

Antibody fragment: It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment, which consists of a VH or a VL domain; (v) isolated CDR regions; (vi) F(ab')2 fragments, a bivalent fragment comprising two linked Fab fragments; (vii) single chain Fv molecules (scFv), wherein a $V_H$ domain and a $V_L$ domain are linked by a peptide linker which allows the two domains to associate to form an antigen binding site; (viii) bispecific single chain Fv dimmers; and (ix) "diabodies", multivalent or multispecific fragments constructed by gene fusion. Fv, scFv or diabody molecules may be stabilized by the incorporation of disulphide bridges linking the $V_H$ and $V_L$ domains. Minibodies comprising an scFv joined to a CH3 domain may also be made. Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group. In some cases a heavy or a light chain may also be considered to be an antibody fragment. As a skilled person will readily appreciate, all the above antibody fragments display at least one function of the whole native antibody from which said fragments are derived and are thus termed 'functional' fragments.

Antigen: Any biomolecule or chemical entity that can be bound by the variable domains of immunoglobulins (or antibodies).

Binding protein: This term defines one protein of a pair of molecules that bind one another. The binding partner of a binding protein is usually referred to as a ligand. The proteins of a binding pair may be naturally derived or wholly or partially synthetically produced. One protein of the pair of molecules has an area on its surface, or a cavity, which binds to and is therefore complementary to a particular spatial and polar organization of the other protein of the pair of molecules. Examples of types of binding pairs are antigen-antibody, biotin-avidin, hormone-hormone receptor, receptor-ligand, enzyme-substrate. The present invention is preferably concerned with antigen-antibody type reactions.

Complementary determining region (CDR): This term refers to the hypervariable regions of the heavy and light chains of an immunoglobulin. CDRs are the regions in the three dimensional structure of an immunoglobulin that directly establish contact to antigen. An antibody typically contains 3 heavy chain CDRs and 3 light chain CDRs. The CDRs are usually the most diverse parts of antigen receptors.

Domain: A structural moiety of a biomolecule that is characterized by a particular three dimensional structure (e.g. variable or constant region domains of immunoglobulins that are structurally related, such as Ig-like domains that can be found in many molecules of the immune system, which belong to the so-called Ig-superfamily).

Germinal center: A distinct histological structure in peripheral lymphoid organs (e.g. lymph nodes or spleen) where cognate interactions between antigen presenting cells and between different lymphocyte populations occur, resulting in the proliferative expansion of antigen-reactive lymphocytes, as well as affinity maturation and class switch recombination of antibodies produced by antigen reactive B lymphocytes.

Germline configuration: The unrearranged configuration of genes and gene loci, as they are inherited from the parents, and as they will be passed on to further generations through the germline. DNA recombination events occurring in somatic cells, like e.g. V(D)J recombination in lymphocytes, lead to the reshuffling or loss of genetic information on certain gene loci and therefore to a change of the genes from the germline configuration.

PreB lymphocyte: A precursor B lymphocyte is characterized by the expression of particular precursor B cell specific genes, like e.g. the λ5 and $V_{preB1}$ and $V_{preB2}$ genes, and the expression of precursor lymphoid specific factors involved in V(D)J recombination (e.g. RAG-1, RAG-2). In addition, precursor B lymphocytes are characterized by the presence of $DJ_H$ on both heavy chain alleles or at least one $V_H DJ_H$ rearrangement on at least one immunoglobulin heavy chain allele, while the light chain gene loci are still in unrearranged, germline configuration, such that the preB cells cannot express complete antibodies.

Primary lymphoid organs: Organs, in which lymphocytes develop from hematopoietic stem cells, in mice and humans e.g. the bone marrow, the thymus, and during fetal life, the liver.

"Quasi-germline" configuration: The artificial arrangement of V, optionally D, and J gene segments with flanking recombination signal sequences cloned from germline immunoglobulin gene loci into artificial genetic constructs, such that the arrangement of the V, optionally D, and J gene segments in such artificial genetic constructs still allows site-specific recombination of the gene segments into a variable coding region by the process of V(D)J recombination.

Somatic mutation: A process in somatic cells resulting in the introduction of point mutations into specific regions of the genome. When this occurs at a high frequency ($>10^{-4}$ mutations per basepair per cell division) it is known as somatic hypermutation.

V(D)J recombination: This is the process for generating antibody and T-cell receptor diversity and is the method by which functional antibody genes are created. It involves the rearrangement of many gene segments that code for the heavy and light chain proteins of immunoglobulins, and it only occurs in lymphocytes.

Transfecting/Transfection: In the context of eukaryotic cells this is the process of introducing nucleic acid sequences into eukaryotic cells, usually associated with using chemical and/or physical methods.

Transforming/Transformation: In the context of eukaryotic cells this is the process of immortalizing a cell for the establishment of a continuously proliferating cell line.

Transducing: The process of delivering DNA into vertebrate cells via the production of recombinant viruses. For this, a packaging cell line, expressing structural proteins for viral particles is transfected with a recombinant viral DNA construct comprising the regulatory elements for packaging of the viral DNA construct into the viral structural proteins. By this, recombinant viruses are produced that can be used to infect (mammalian) target cells leading to the introduction of the genetic information cloned into the recombinant viral genome.

Vector/Construct: An artificially generated nucleic acid sequence which can be used to shuttle nucleic acid elements between different organisms and species, and which can further be used to propagate, amplify and maintain genomic information.

DETAILED DESCRIPTION

Antibodies, or immunoglobulins, are the most widespread class of binding proteins that have proven to be particular useful for therapeutic and for diagnostic applications. Therapeutic antibodies have developed into the commercially most successful class of biologic drugs and there is continued interest in novel and powerful methods to develop antibody-based therapeutics (Baker, 2005).

Antibodies consist of two identical heavy (H) chain and light (L) chain glycoproteins that are covalently linked via disulphide bonds (FIG. 2a). Each immunoglobulin heavy (IgH) and light chain (IgL) polypeptide comprises an N-terminal variable domain that varies between different antibodies and a C-terminal constant region, that is identical between different antibodies belonging to the same immunoglobulin subtype (isotype) (FIG. 2a). The combination of IgH and IgL chain variable domains creates the antigen binding pocket of an antibody and determines its specificity, whereas the constant regions determines the immune effector function of an antibody. The variability of immunoglobulins in their variable domains results from the fact that $V_H$ and $V_L$ domains are encoded by a multitude of gene segments, that are designated V (variable), D (diversity), and J (joining) gene segments. During the differentiation of B lymphocytes one V, one D (only present in the IgH chain locus) and one J gene segment is randomly selected in each cell and is site-specifically rearranged in order to generate the coding region for $V_H$ or $V_L$ domains. This site specific genetic recombination process only occurs in precursor lymphocytes and is known as V(D)J recombination (Grawunder et al., 1998) (also refer to FIGS. 2b and 2c). The rearrangement of gene segments is mediated by recombination-activating gene (RAG) 1 and 2 products. Due to the multitude of V, D, and J gene segments, and imprecision in gene segment joining, an enormous repertoire of different V region specificities can be generated by the millions of B lymphocytes produced by the immune system every day (Grawunder et al., 1998). Because the immunoglobulin heavy chain gene locus contain V, D and J gene segments, the coding region for a $V_H$ domain of an antibody requires two sequential V(D)J rearrangement events, whereas the immunoglobulin gene locus lacks D gene segments and the $V_L$ coding region is generated by one V to J-rearrangement event (FIG. 2c). Therefore, the junctional diversity that is generated by V(D)J recombination in the CDR3 region of IgH chains is greater than the CDR3 junctional diversity that is generated by only one rearrangement event for the IgL chains. In addition, at the early B cell differentiation stages, during which IgH chain gene rearrangements occur, the enzyme terminal deoxynucleo-tidyltransferase (TdT) is expressed, that is able to add non-templated nucleotides at the D to J and V to D junctions (so-called N-sequence diversity), additionally diversifying the IgH chain CDR3 repertoire. In contrast, the CDR3 repertoire of the IgL chain, which is formed upon V to J gene segment joining later during B cell differentiation, when TdT expression is largely downregulated (Li et al., 1993), is somewhat less complex. Apart from the generation of CDR3 diversity in $V_H$ and $V_L$ coding regions, both IgH and IgL chain repertoires can further be diversified by the process of somatic hypermutation that is triggered in mature B cells during the course of a T cell dependent immune reaction (Papavasiliou & Schatz, 2002). The somatic mutations are specifically targeted to the $V_H$ and $V_L$ coding regions, and are mediated by the B lineage specific enzyme activation-induced cytidine deaminase (abbreviated AID, see: Papavasiliou & Schatz, 2002). As a consequence of somatic hypermutation occurring during immunization, cells expressing higher affinity antibody mutants against the immunogen are positively selected in the course of an immunization mostly occurring in germinal centers, and resulting in an enrichment of cells producing higher affinity antibodies. These antibodies now also accumulate mutations in CDRs 1 and 2, a process, which is referred to as affinity maturation of the antibody repertoire. The AID-mediated diversification and specific targeting to the $V_H$ and $V_L$ coding regions is significantly increased by the presence of cis-regulatory genetic elements or motifs, in particular enhancer elements of the IgH and IgL chain gene locus, located in the proximity of the rearranged $V_H$ and $V_L$ coding regions (Bachl & Olsson, 1999).

Besides classical, full-length therapeutic antibodies, additional formats of binding proteins, comprising fragments of fully human antibodies, e.g. so-called $F_{ab}$ fragments (FIG. 2a), single-chain $F_v$ fragments (FIG. 2a), nanobodies, only consisting of single $V_H$ domains, etc., are also increasingly being explored as therapeutic and diagnostic agents. However, it is clear to a person skilled in the art, that such functional antibody fragments can easily be derived from full-length antibodies by either standard biochemistry methods on protein basis, or by conventional molecular biology methods, if the coding information of a desired full-length antibody is available.

Traditionally, monoclonal antibodies directed against a molecule or epitope of interest (antigen) are generated by immunization of small laboratory, or farm animals, e.g. mice, rats, rabbits, or goats and donkeys, respectively. After repeated immunizations, animals are either bled for the isolation of polyclonal antibodies from their blood serum or, for the generation of monoclonal antibodies, the animals are sacrificed in order to isolate lymphocytes from secondary lymphoid organs, like lymph nodes or the spleen. Isolated lymphocytes are fused to immortal myeloma cells for the generation of hybridomas, which are subsequently subcloned and screened for the secretion of monoclonal antibodies exhibiting desired functional properties, like e.g. binding to a particular antigen or target.

From the first breakthrough in antibody engineering, namely the development of hybridoma technology for the generation of so-called monoclonal antibodies by Köhler and Milstein (Köhler & Milstein, 1975), it took a long time until monoclonal antibodies could be used for the treatment of human disease.

The main reasons for the slow entry of antibodies into the clinic were initial setbacks associated with using rodent antibodies for treating human patients. If such antibodies are infused into the immune system of a patient, the immune system recognizes the rodent antibodies as a foreign protein and mounts an immune response against these antibodies, including the generation of neutralizing antibodies (known as HAMA=human-anti-mouse antibody response). A HAMA response can lead to a significant decrease in the half-life and, hence, the efficacy of the applied antibody, and can even lead to severe side-effects, if the immune system overreacts against the injected non-human protein.

Therefore, it was of great medical and commercial interest to develop therapeutic antibodies that were "more" similar to human antibodies. Initially, this was achieved by means of genetic engineering of existing rodent antibodies, resulting in the development of either chimeric or humanized antibodies (Clark, 2000). Chimeric antibodies are generated by fusing the variable binding domains of a rodent antibody to the constant regions of a human antibody, using standard genetic engineering and cloning techniques. Humanized antibodies, in contrast, are generated by only transferring the complementarity determining regions (CDRs) of a variable domain from a rodent antibody to the variable region framework of a human antibody, which is also done by standard molecular biology techniques. While the procedure for generating chimeric antibodies is straightforward, these antibodies still contain 33% xenogeneic sequences and harbour a significant potential for immunogenicity (Clark, 2000). In fact, immune responses to the mouse parts of a chimeric antibody are well documented and are referred to as HACA-responses (HACA=human anti-chimeric antibody).

In contrast to the aforementioned, the immunogenic potential of humanized antibodies is further decreased. However, the procedure of genetically engineering humanized antibodies and at the same time maintaining original binding affinities and specificities of the rodent antibodies after CDR grafting is not trivial, and often requires extensive additional optimization by repeated mutagenesis and screening cycles. For the above-mentioned reasons, chimerization and humanization approaches have become less appreciated in recent years as a method of choice for the development of therapeutic antibodies.

The development away from chimeric and humanized antibodies for the development of therapeutic antibodies, has also been driven by the development of innovative technology platforms allowing the development of "fully human" antibodies, which by amino acid sequence are identical to human serum antibodies. Fully human antibodies theoretically are thought to cause the least immunogenicity and side-effects in human patients.

The two most established "fully human antibody" development platforms are:

A) Human immunoglobulin transgenic mouse technology, in which large transgenes of germline human immunoglobulin heavy and light chain gene loci have been introduced into the mouse genome (Green & Jakobovits, 1998; Jakobovits et al., WO98/24893 A2). In order to use these transgenic mice for the development of human antibodies, these transgenic mouse strains have been crossed to gene knock out mouse strains harbouring functional deletions in their endogenous mouse immunoglobulin heavy and κ light chain gene loci. Thus, these human immunoglobulin transgenic mice mount a largely human humoral immune response upon immunization, with the exception that approximately half of the antibody producing cells still harbour endogenous mouse λ light chains, which are therefore useless for further therapeutic antibody development, and need to be discarded.

B) Phage display technology, which is based on the expression (display) of highly diverse libraries of antibody fragments (e.g. as single chain $F_v$ or $F_{ab}$ fragments) on the surface of bacteriophages of E. coli (Clackson et al., 1991; McCafferty et al., WO 92/01047 A1). For the identification of specific binders, phage libraries of appropriate complexity, quality and origin are bound to immobilized antigens ("panning"), in order to enrich for phage clones binding to the immobilized antigen. After several rounds of panning, sequences of selected binding clones are determined. A variation of the method is the completely cell-free ribosome display technology, in which antibody fragments are not displayed on phage, but rather expressed by in vitro transcription and translation, under conditions, where the translated binders still "stick" to ribosomes (Hanes & Plückthun, 1997). For either phage or ribosome display one crucial step is the re-engineering of binding fragments into full-length antibodies, which are then expressed in vertebrate cells. After re-engineering of phage selected clones into a full-length antibody format and vertebrate cell expression it needs to be analyzed, whether the antibodies can be expressed adequately and whether the original phage binding characteristics are still maintained, which may not necessarily be the case.

Although the human immunoglobulin transgenic mouse and the phage display technologies have had a major impact on therapeutic antibody development, both technology platforms have advantages and disadvantages associated with them.

One advantage of the transgenic mouse technology is that it can deliver high affinity antibodies, due to the natural affinity maturation occurring in these mice upon in vivo immunization, and it has been demonstrated that the affinity profile of human antibodies towards a given antigen derived from human transgenic mice can be comparable to that of wild-type mice. However, several disadvantages associated with the human immunoglobulin transgenic animals are:

1) If the transgenic animals are tolerant to the antigen, most often due to high structural similarity to endogenously expressed host proteins, the generation of high affinity antibodies against such "conserved" antigens can turn out to be very difficult, or even impossible. 2) Like in normal wild-type animals, antibodies from human immunoglobulin transgenic animals are preferentially generated against strong antigenic epitopes, which can make it a challenging task to develop an antibody against functional, but weak epitopes of therapeutic value. 3) Lastly, human immunoglobulin transgenic animals cannot be used for affinity optimization of existing antibodies. The reason for this is that the time frames required for the generation of transgenic animals, just for the optimization of one given antibody clone, are too long. Such an approach would involve the generation of two IgH chain and IgL chain transgenic mouse strains for one particular antibody and would then additionally require the genetic backcrossing of these two transgenic strains to at least two knock-out animal strains deficient for both endogenous immunoglobulin heavy and for κ light chain expression, a process that would require several breeding generations and extended time frames.

Similar limitations as described above, apply to a recently described technology-platform based on the development of mice, in which the germline variable (V), diversity (D) and joining (J) gene segments of the mouse immunoglobulin heavy and light chain gene loci have been replaced by (parts of) human germline V, D and J gene regions by site-specific gene targeting (Murphy & Yancopoulos, WO 02/066630 A1). In these "immunoglobulin gene-knock-in" mice, the murine V, D and J gene segments have been site specifically replaced by those of the human immunoglobulin gene heavy and light chain gene loci via homologous recombination in the mouse germline. In contrast to human immunoglobulin transgenic mice, which produce fully human antibodies, this mouse strain therefore produces "reverse-chimeric" antibodies, carrying human antigen binding regions on a mouse constant region backbone.

Phage and/or ribosome display approaches have the perceived advantage of being very fast technology platforms, because the identification of first binders from complex libraries of binding proteins can be accomplished within a few weeks. However, phage display is also associated with significant disadvantages. 1) Due to the absence of any affinity maturation in the system, it is not trivial to identify high affinity binders from a phage or ribosome display screen. In order to address this problem, extremely complex phage libraries representing more than $10^{12}$ clones have been developed. But even using such complex libraries, initial binding clones often have suboptimal affinity to the antigen and such binders usually still need to be optimized using additional tedious and time consuming optimization procedures. 2) In phage display, only antibody fragments, such as scF, or $F_{ab}$ fragments are expressed, because the phage genome can only accommodate coding regions for relatively small-sized molecules. 3) Binding proteins have to be fused to carrier proteins such as the phage gIII protein. The resultant fusion proteins frequently reveal lower antigen-reactivity compared to their parental antibodies or binding-active proteins (Hoogenboom & Chames, 2000). 4) Phage display does not easily allow for a controlled assembly of proteins that attain a binding phenotype through the formation of homo- and hetero-multimer formation, because e.g. dimeric proteins are forced to assemble by covalent linker molecules. However, in the case of antibody engineering a properly regulated assembly of immunoglobulin heavy and light chains is essential, as not every antibody heavy chain is able to pair with any light chain. 5) Bacteria- or bacterial phage-based systems do not provide appropriate posttranslational modifications (glycosylation, myristoylation and the like) of the displayed protein of interest, which often negatively influences the binding characteristics of the expressed proteins. 6) Prokaryotic expression results in different protein folding of proteins in comparison to vertebrate cells, as the cytoplasmatic environment dramatically differs from eukaryotic or vertebrate host cells, e.g. In redox potential and the lack of chaperones. 7) Phage display systems are subsequently subjected to antigen binding- or capture-assays to enrich reactive cells under quite non-physiological "panning" conditions, which may lead to the identification of a large percentage of false-positive binders that eventually need to be discarded.

As a result of the abovementioned drawbacks, many phage-display selected antibody fragments have mediocre affinity and/or may carry structural artefacts. In addition, once phage display selected binders are re-engineered and expressed as full-length antibodies in vertebrate cells, it may happen that phage selected antibodies are either poorly or not at all expressible, or that they exhibit altered binding characteristics.

In order to address some of the limitations of human immunoglobulin transgenic/knock-in mouse technology and phage display, an alternative technology has recently been developed, which involves the genetic modification of primary murine preB cells in vitro, resulting in cells expressing human antibodies, followed by their engraftment into immunodeficient recipient mice lacking a functional B cell compartment (Grawunder & Melchers, WO 03/068819 A1). This leads to a partial reconstitution of B cell subsets expressing human antibodies in the engrafted mice, which may subsequently be immunized with any desired antigen or ligand. This technology can be used to either develop novel antibodies or binding proteins, or to optimize existing antibodies with regard to their affinity against a defined target (Grawunder & Melchers, WO 03/068819 A1).

The use of retroviral expression systems in this method is preferred, because gene transfer of single copies of expression constructs can be transferred into individual preB cells (Kitamura et al., 1995; Stitz J et al., 2005), and also, because there is complete freedom of choice, as to which antibody expression constructs are being used for engraftment for the mice (e.g. antigen pre-selected antibody libraries, antibody libraries from diseased patients, or individual antibody clones). Therefore, a particular advantage of this technology is its flexibility that it can be applied to de novo development of antibodies, as well as to the optimization of existing therapeutic antibody candidates.

Other rodent-based systems for the development of fully human antibodies have been described, which involve the transplantation of human hematopoietic progenitor cells isolated from human donors into immunodeficient mice (Mosier & Wilson, WO 89/12823 A1). In such human cell engrafted mice, human B cells may develop to some extent, however, despite recent improvements of this method (Traggiai et al., 2004), a satisfactory humoral immune response involving affinity maturation of human antibodies is not achieved in such "humanized mice". In addition, like in the case of human immunoglobulin transgenic or "knock-in" mice, existing antibodies cannot be optimized.

Any kind of mouse based antibody technology platform usually requires in vivo immunization which remains a time-consuming process when compared to in vitro approaches.

Therefore, in addition to the aforementioned mouse-related approaches, a variety of alternative in vitro technologies have recently been developed. However, it still needs to be proven how efficient these systems will be in developing high quality, high affinity antibody products. One in vitro system is based on the isolation of antigen-enriched memory B cells from human patients with a particular disease that can be isolated and then be immortalized by Epstein-Barr Virus (EBV) transformation in vitro, followed by the screening for antigen-reactive EBV lines (Lanzavecchia, WO 04/76677 A2). Similar in concept, but different in methodology are approaches in which antibody producing plasma cells from patients with an acute disease status are first isolated from peripheral blood and then immortalized by fusion to non-producing heteromyelomas, followed by their screening for desired antibody producers (Lang et al, WO 90/13660 A2). Alternatively, methods have been described aiming at the isolation of B cells from vaccinated or immunized individuals followed by isolation and cloning of specific antibody genes either from cell populations (Lawson & Lightwood, WO 04/106377 A1; Schrader, WO 92/02551 A1) or by single-cell PCR (Muraguchi et al., WO 04/051266 A1). However all these technologies rely on the availability of relevant B cell populations in human patients and are quite limited in their general application and are therefore mainly used for the identification of anti-infective therapeutic antibody candidates. Furthermore, neither affinity maturation, nor antigen-directed development of antibodies, nor optimization of existing antibodies is possible with any of the human B cell-based screening approaches.

Therefore, additional alternative in vitro methods have recently been described involving the expression and screening of recombinant antibodies in eukaryotic cells using transient expression systems (Zauderer & Smith, WO 02/102855 A2 and Beerli et al, WO 08/055,795 A1). While these systems circumvent some of the bottlenecks of transgenic mice, phage display and human B cell derived technologies, these systems still are characterized by a number of limitations. First, the known eukaryotic cell-based antibody expression/screening technologies do not confer a stable expression pattern for recombinant antibodies, precluding repetitive enrichment cycles of antibody-expressing cells with desired binding specificity. Second, none of the known approaches involving eukaryotic cell based antibody expression allows control for clonal expression of binder clones, which in the case of therapeutic antibody development makes it a challenging task to identify a matching IgH chain and IgL chain pair with desired antigen or ligand binding activity. Third, the technology described in Zauderer and Smith (WO 02/102855 A2) does not allow any in vitro mutagenesis, or genetic recombination of the expressed antibodies, the method is a mere screening procedure. Therefore, aspects of affinity maturation of binding proteins are not addressed by this technique. Lastly, none of the eukaryotic expression/screening systems are compatible with the in situ generation of diverse antibody repertoires from individual antibody expression constructs exploiting the mechanism of V(D)J recombination of immunoglobulin heavy and light chain V, D and J gene segments.

An alternative method for the identification of biologically active peptides and nucleic acids has been proposed by Jensen et al (EP 1 041 143 A). The preferred method described in EP 1 041 143 A comprises an initial screening procedure in which a large number of retroviral vectors can be introduced into cells such that the individual cell can express a number of different RNAs or peptides. The cells that show a phenotypic change are subsequently isolated and the retroviral DNA in that clone can be isolated by PCR. This PCR product can then be used to re-transfect viral packaging cells to create further retroviral vectors. These retroviral vectors can then be used for the transduction of different cells and finally after a second cloning procedure the active substance can be identified. Essentially this method results in an indirect change in the phenotype of a cell by the importation of biologically active peptides or nucleic acids. This is in contrast to the method of the present invention whereby the retrovirally transduced constructs directly encode the binding proteins, preferably antibodies, to which the screening is directed. It should also be noted that the peptides and nucleic acids described in EP 1 041 143 A differ greatly in size to the antibodies or antibody fragments identified by methods of the present invention.

A further method for retrovirus-based genomic screening is set out in WO 03/083075 A2 (Bremel et al). This method relates to the expression and screening of genomic DNA sequences encoding uncharacterised genes and proteins. A process is described in which a cell line is transduced with a retroviral expression construct such that a genomic DNA virus is inserted into the genome of the cell line as a provirus, and then the expression of polypeptides from the provirus is analysed directly. Such a method does not provide the opportunity for enrichment of the cell line, nor for the isolation and identification of the expressed polypeptides before analysis is performed, which would detract from the high-throughput screening technology developed by Bremel and co-workers.

A recently published patent application (WO 08/055,795 A1) from Beerli and co-workers describes a screening platform for the isolation of human antibodies, which utilises a Sindbis virus expression system. An essential feature of this platform is the generation of starting library where B cells specific for an antigen of interest are directly isolated from peripheral blood mononuclear cells (PBMCs) of human donors. Recombinant, antigen-reactive scFv libraries are generated from this pool of B cells and screened by mammalian cell surface display by using a Sindbis virus expression system. Similar to phage display, one of the drawbacks to this system is that the scFvs of interest need to be re-engineered and expressed as full-length IgGs in vertebrate cells. Such a process can be associated with a loss in affinity of the antibody of interest on conversion since these antibodies may not express well in vertebrate cells and/or may exhibit altered binding characteristics.

In contrast, the invention disclosed herein comprises a unique extremely powerful combination of methods for the development and optimization of binding proteins, preferably antibodies, or fragments thereof. In comparison to mouse-based technologies, the main advantages of the invention disclosed herein are complete flexibility in terms of optimization and de novo development of antibodies, and the speed to identify specific binders in short periods of time. As all aspects of the invention are realized in vitro, there is no limitation with regard to the development of antibodies against antigens, which are highly conserved across species, or that may be toxic in experimental animals.

In comparison to phage display based technologies, the key advantages of the invention disclosed herein is that the binding proteins, in particular antibodies, can be expressed as full-length antibodies, in a vertebrate cell, and preferably in a B lymphocyte environment, i.e. the natural host cell of antibodies, ensuring most natural and proper protein folding, correct posttranslational modification, and a quality control for heavy and light chain pairing.

In comparison to human B cell approaches the key advantages of the disclosed invention are the complete flexibility with regard to development of antibodies against any desired target, the possibility to affinity optimize existing antibodies, a complete freedom of choice as to which type of antibody is expressed in the system (antigen-enriched, synthetic, from patients, under conditions of IgH and IgL chain shuffling, etc.).

In comparison to other eukaryotic cell-based expression systems involving either plasmid based expression constructs or non-integrating viral vectors, key advantages of the disclosed invention of 'Retrocyte Display' are that stable, sustained and clonal expression can be achieved by use of retroviral gene transfer technology. The stable, sustained and clonal expression of recombinant antibodies in the target cells allows repetitive enrichment cycles of antigen- or ligand specific cells, including the possibility to isolate and to expand monoclonal cells for identification of the antibody genes. Moreover, the invention disclosed herein additionally allows the additional generation of genetic diversity upon retroviral transduction into vertebrate host cells in situ using single retroviral constructs by either exploiting the lymphocyte specific mechanism of V(D)J recombination, or exploiting the process of somatic hypermutation for further mutagenesis of binding proteins.

Therefore, in comparison to any of the known technologies for the development of therapeutic antibodies known in the art, the method of retrocyte display disclosed herein provides unique, novel and powerful solutions for many evident limitations that pre-existing technologies suffer from.

The invention disclosed herein is broadly applicable to the expression, screening and identification of binding proteins specifically binding to a ligand or antigen of interest. While the invention can be performed with any binding protein, including but not limited to monomeric, homo- or heteromultimeric membrane bound receptors, like T cell receptors, cytokine, or chemokine receptors, but also with other scaffold proteins, the preferred binding proteins according to the invention are full-length antibodies, with fully human antibodies being particularly preferred. However, it is to be understood, that any (functional) fragment of an antibody, including, but not limited to single chain Fv fragments ($scF_v$), Fab fragments, F(ab')2, single $V_H$ or $V_L$ domains, single heavy or light chains or any combination thereof, with any naturally occurring or artificially engineered modification may be used to realize the invention. With regard to fulllength antibodies, the invention is particularly applicable to any kind of artificially engineered or designed modifications of antibody binding regions, e.g. those generated by site-, or region-directed mutagenesis, fusion of naturally occurring sequences from different antibodies, randomization of CDR sequences, DNA shuffling, error-prone PCR, just to name a few methods by way of illustration.

A preferred method for the expression of binding proteins according to the invention is to use retroviral vector-mediated transduction of vertebrate host cells.

The use of retrovirus vectors has been investigated for many years in the field of gene therapy. For example, to engineer adeno-associated virus (AAV) vectors that can be targeted to specific cell types, Perabo et al., (WO 03/054197 A2) have inserted randomised sequences encoding targeting peptides into the viral capsid gene, at a site critical for binding to the primary cellular receptor, and produced AAV libraries that displayed the peptides in the context of the viral capsid. The selective pressure provided by the culture environment drove the selection by means of the ability of the viral clones to accomplish every step in the infection process, namely binding, uptake, uncoating, nuclear translocation, replication, and gene expression. By using this technique, vectors were generated that efficiently transduced leukemia cells. Whilst such a technique may be useful to generate viral mutants that infect target cells previously resistant to infection by wild-type AAV, it does not provide for the generation of diverse collections of binding proteins in vitro.

As such, the methods described in the present application for the expression of binding proteins have several key advantages over any other methods known in the art for the expression of recombinant proteins in eukaryotic and/or vertebrate host cells.

1) Recombinant retroviral constructs stably integrate into the host cell genome and thereby confer a stable and sustained expression phenotype of the binding protein. 2) By utilization of appropriate ratios of retroviral particles to target cells, termed "multiplicity of infection" (MOI), preferably performed at a MOI of equal or less than 0.1, the retroviral transduction can be controlled, such that the majority of retrovirally transduced cells are genetically modified by only one recombinant retroviral construct integrating into the host cell genome resulting in clonal expression of an at least one desired binding protein. Because clonal expression of binding proteins greatly facilitates the identification and cloning of individual binding proteins, this aspect therefore represents a preferred embodiment of the invention. However, in an alternative embodiment, the invention may also be realized using retroviral transduction at MOTs of greater than 0.1.

Despite the aforementioned advantages of retroviral transduction as a basis for retrocyte display, expression of recombinant binding proteins in vertebrate host cells may also be achieved by alternative methods, like, for instance, but not limited to, transient or stable DNA transfection, RNA transfection, or by transfer of DNA-based viral vectors, like adenoviral or poxvirus-based vectors—albeit none of the aforementioned alternative methods allows for an easily controllable stable and clonal expression of binding proteins in vertebrate host cells.

Preferred vertebrate host cells for the realization of the invention are cells of the B lymphocyte lineage, in particular precursor B lymphocytes, which often lack endogenous antibody expression, but which express favourable accessory proteins, like e.g. chaperones for proper protein folding and antibody assembly, or accessory membrane proteins facilitating membrane deposition of antibody molecules, like e.g. the B cell specific Igα or Igβ proteins.

The principle of expression of recombinant proteins by retroviral transduction in vertebrate host cells is an established procedure and involves the construction of recombinant retroviral vectors, that are relatively small (maximal size of recombinant DNA to be incorporated: 8-10 kB) and that can be cloned and manipulated by standard molecular biology methods as plasmid vectors, from which the retroviral RNA genome can be transcribed. A wild-type retroviral genome only contains three genes, gag, pol and env, which encode the nuclear core proteins, a retroviral integrase, protease, RNAse, and a reverse transcriptase, and envelope proteins, respectively (FIG. 3a). In addition, the retroviral genome contains cis-regulatory sequences, like the Psi (ψ) sequence required for packaging of the retroviral RNA genome into virus particles, a polyA signal for retroviral transcript termination, and lastly, so-called 5'- and 3'-longterminal repeats (LTRs) containing promoter elements and signals for retroviral integration into the host cell genome (FIG. 3a). For the construction of recombinant retroviruses, the gag, pol and env coding regions of a wild-type retrovirus are replaced by any expression cassette for a gene of interest (FIG. 3a), including relevant cis-regulatory elements, like promoters or enhancers. In order to stably integrate such recombinant retroviral genomes into a host genome, a plasmid vector containing a retroviral genome needs to be transiently or stably transfected into a so-called retroviral packaging cell line (PCL), expressing the viral structural proteins encoded by gag, pol and env in trans in a transient or stable fashion, and therefore allowing the packaging of the recombinant viral genome (the transfer vector) into replication incompetent retroviral particles (FIG. 3b). These retroviral particles allow for a single-round infection (transduction) of target cells (FIG. 3b). The entry of the retroviral particle into target cells is mediated by a specific interaction of the Env protein with a specific receptor on the target cell. Thus, the nature of the Env protein determines the tropism of the retroviral particles to specific host cells expressing the cognate receptor. Ecotropic retroviruses are restricted to rodent cells, amphotropic retroviruses may infect various species including rodent and human cells and pantropic retroviruses may infect any replicating cell with a cell membrane, as the cell entry occurs via structures present on all eukaryotic cell membranes. Retroviral vector particles with a variety of different tropisms can also be generated using heterologous envelope proteins of other viruses such as gibbon ape leukemia virus (GaLV), vesicular stomatitis virus (VSV) or HIV and SIV or even cellular membrane proteins, just to name a few by way of illustration—a technique known as "pseudotyping". Following cell entry, a retrovirus can deliver the viral genome into the host cell, where the viral proteins mediate reverse transcription of the genome into cDNA and eventually its stable integration into the host cell genome, allowing stable expression of the delivered genes (FIG. 3b). In a preferred embodiment of the invention ecotropic MLV particles are used to mediate gene transfer into murine B cells. However, it will be appreciated by any person skilled in the art that any infectious retroviral vector pseudotyped with any other envelope or transmembrane protein can be employed to realize the invention, provided that it mediates transduction in any appropriate target selector cell independent from their parental donor species, cell type or their expression of a cognate receptor mediating vector cell entry.

To achieve retroviral vector-mediated gene transfer, vector-containing retroviral particles (containing transcripts of recombinant retroviral genomes, or transfer vectors) can be harvested from the cell culture supernatant of packaging cells either stably or transiently expressing transfer vectors (FIG. 3b). This can be carried out in a broad range of protocols and variations thereof, known to a person skilled in the art. Preferred embodiments of this invention include: 1) preparation of cell-free retroviral particle containing supernatants using either passage through an appropriate filter or a centrifugation step that separates packaging cells from vector particles. These retroviral particle preparations are subsequently used to transduce vertebrate host cells by co-incubation for a variable time frame or by performing a so-called "spin infection". Here, a target cell suspension is mixed with retroviral particle containing medium and is subjected to low-speed centrifugation (FIG. 3b). 2) Alternatively, co-cultivation of target cells with packaging cells enabling cell-to-cell contact or separation of both cell populations by a membrane which allows the passage of retroviral particles but not of the packaging cells, can be performed to enable transduction of target cells.

As host target cells for retroviral transduction a preferred embodiment of the method is to use B-lymphocyte lineage cells from rodents that do not express endogenous murine immunoglobulin proteins, and that can be transduced with retroviruses of ecotropic host range. Cells of the B lymphocyte lineage have the advantage that they already express B cell specific Igα and Igβ proteins that are favourable for cell surface expression and anchoring of membrane bound, full-length immunoglobulins. In that regard, immunoglobulin negative plasma cell-derived cells, like e.g. myeloma cells, as for instance, but not limited to Sp2/0, NSO, X63 and Ag8653 generally lack the accessory Igα and Igβ proteins for membrane immunoglobulin deposition. In such cases and in any other vertebrate host cell, in which Igα and Igβ proteins are not expressed, the method may still be applied, if expression of the Igα and Igβ proteins is conferred upon transfection or transduction of expression vectors for Igα and Igβ, a standard procedure for any person skilled in the art. Thus, upon ectopic expression of both Igo and Igβ proteins, the method may be realized with any vertebrate host cell line, provided that retroviral particles with appropriate tropism are produced, that are able to transduce said vertebrate host cell line. In order to clarify, the innovation disclosed herein could be realized with any vertebrate host cell, if pantropic retroviral particles (for instance, but not limited to particles pseudotyped with the G protein of VSV) are used in connection with a host cell that has been modified to ectopically express the immunoglobulin anchor molecules Igα and Igβ.

Preferred cells of the B-lymphocyte lineage are for instance, but not limited to precursor B-, B-leukemia or B-lymphoma cells, from any vertebrate species, but also primary precursor B cells that can be grown in tissue culture for long periods of time. Precursor B lymphocytes would represent ideal host cells for retroviral expression of immunoglobulins, as the majority of such cell lines, do not express endogenous immunoglobulin proteins. In particular, as murine preB cell lines can easily be obtained from any mouse strain by transformation with Abelson-murine leukemia virus (A-MuLV). However, either primary, long-term proliferating preB cells, as well as A-MuLV transformed preB cells express the preB cell specific proteins VpreB and λ5, which together form the so-called surrogate light chain, which, in the absence of conventional light chains, can form preB cell receptor complexes of immunoglobulin heavy and surrogate light chain. Because it is desired to express immunoglobulins composed of recombinant heavy and light chains, preB cells are preferred that lack expression of surrogate light chain components, comprising the gene products of the λ5, or VpreB1, or VpreB2 genes either as single, double or triple-gene knockouts. As it is known that surrogate light chain can bind to heterologous heavy chains it is expected that surrogate light chain expression may interfere at a varying degree with the screening of IgH/IgL pairs, but due to generally low expression levels of surrogate light chain proteins in preB cells, the method may yet be realized using wild-type preB cells, expressing surrogate light chain components. In summary, any vertebrate cell line expressing Igα and Igβ, and not expressing endogenous immunoglobulin proteins may be used as target host cells for the method, with surrogate light chain deficient preB cells being the preferred host cells for realizing the invention.

The preferred binding proteins to be expressed, screened and identified are full-length antibodies, and by amino acid sequence, fully human immunoglobulins. However, it shall be understood, that any binding protein capable of cell expression in vertebrate cells may be subjected to screening and selection for specific ligand or antigen binding according to the disclosed method. For instance, such binding proteins may include fragments of antibodies from any vertebrate species, like e.g. single chain Fv, Fab fragments (FIG. 2a) or single $V_H$ or $V_L$ domains, or a heavy or light chain, preferably expressed in a way that deposition on the cell surface membrane is enabled. This could be achieved e.g. by fusion to membrane anchors of other type-I transmembrane proteins, utilization of GPI-anchor domains or other methods know in the art. Furthermore, the method would also be applicable to other membrane bound proteins, e.g., but not limited to, monomeric or multimeric cytokine receptors, or dimeric T cell receptors and like. Retroviral expression of immunoglobulin heavy and light chains is preferably achieved by sequential transduction of separate retroviral expression constructs for heavy and light chains. However, the invention can also be realized by performing a co-transduction of the target cells, in which separate retroviral constructs for IgH and IgL chains are being used. The separate expression of IgH and IgL chains from different retroviral vectors offers the advantage, that collections of retroviral vectors encoding a diverse collection of immunoglobulin heavy chains can randomly be combined with collections of retroviral expression vectors encoding a diverse collection of immunoglobulin light chains. This so-called heavy and light chain shuffling can create a large degree of diversity of different immunoglobulin binding specificities, even when the total number of heavy and light chain collections are limited (e.g. $10^4$ different heavy chains, randomly combined with $10^4$ different light chains theoretically results in $10^8$ different antibody specificities). Shuffling of collections of IgH and IgL chain vectors is preferably performed with a one sided shuffling, meaning that one polypeptide chain of an antibody is a single construct encoding a single antibody chain.

However, it is to be understood, that retroviral IgH and IgL chain expression can also be achieved, if both proteins are encoded on the same retroviral backbone (see below). In its easiest configuration the heavy and light chain expression is conferred by cloning of heavy and light chain cDNAs into an empty retroviral vector, where expression is driven by the promoter activity of the 5'LTR and proper RNA processing is mediated by the 3'LTR sequences (FIG. 3a). The heavy chain constructs should preferably contain their endogenous membrane-spanning coding region, in order to allow optimal membrane deposition of the recombinant immunoglobulins. However, for those skilled in the art, it is obvious that also membrane spanning domains of other transmembrane proteins may be fused to the constant regions of antibodies, in order to assure surface deposition of the expressed modified immunoglobulins. In particular in the context of expression of antibody fragments, or the expression of non-immunoglobulin binding proteins, different transmembrane regions of membrane bound proteins may be advantageous for cell surface expression of the binders.

Whereas cell surface expression of antibodies or fragments thereof is a preferred embodiment of the current invention, these biomolecules may alternatively also be expressed as soluble, secreted proteins, such that detection of the antibody is performed in fluid phase. Such a form of expression could be advantageous, if the screening of single producer clones and binders involves an assay requiring soluble antibodies, or if the assay is performed in semi-solid media with an assay allowing the quantitation of expression levels and binding specificities on single cell clones. Expression vectors for recombinant immunoglobulins may be employed coding for all known immunoglobulin heavy and light chain isotypes, which in the case of fully human antibodies, allows the expression of IgM, IgD, $IgG_1$, $IgG_2$, $IgG_3$, $IgG_4$, $IgA_2$ and IgE antibodies, either containing Igκ or Igλ light chains. In all retroviral expression vectors for human heavy and light chains, it is preferred that only the variable coding region of a human heavy and light chain shall be replaced using unique restriction enzymes, like e.g., but not limited to HindIII and Eco47III, as depicted in the schematic drawing of retroviral antibody expression vectors (4a and 4b). This will allow easy cloning and replacement of variable coding regions in retroviral expression vectors, either with V-region libraries or individual V-region coding regions, in-frame to the constant coding regions for immunoglobulin heavy and light chains. Such a scheme of only exchanging variable region domains, either aiming at generating expression vectors encoding a single specificity, or aiming at generating a collection of binding proteins will be favourable. In this regard full-length antibodies may be expressed that contain variable region domains and constant region domains derived from different species (chimeric antibodies).

The simplest retroviral expression vector for binding proteins could be constructed by insertion of a cDNA coding region for the binding protein or gene of interest into an "empty" retroviral expression vector backbone (FIG. 3a). Even in the absence of any selection marker and/or screening marker (e.g. enhanced green fluorescent protein, EGFP) allowing the direct detection of transduced cells, the invention could be realized, because cells stably expressing binding proteins from the retroviral vectors can be identified and isolated based on the stable expression of the binding proteins, either in secreted or in membrane-bound form. However, various features included in the retroviral expression vectors are preferred. The first one is a strong constitutive or an inducible promoter element driving the expression of the recombinant binding proteins, which are placed directly upstream of the coding cDNA regions (FIG. 4a, b). Such promoters may be, for instance, but not limited to, constitutive promoters, as the immediate early CMV promoter, β-actin promoter, EF-1α promoter, or inducible promoters, like tetracycline- or any other antibiotic-inducible promoter, that may either upregulate or downregulate expression by addition or removal of tetracycline or other antibiotics and derivatives thereof, like doxycycline. The inclusion of inducible promoter elements in the retroviral expression constructs is another preferred embodiment, because it is known that in some retroviral vector backbones either 5'LTR promoters or even strong constitutive promoters can be silenced.

In addition to promoter elements, it is a preferred embodiment to include marker genes in the retroviral expression constructs, which subsequently allow the selection and/or monitoring of stable retroviral transduction of host cells without detection of the recombinant binding proteins (FIGS. 4a, b). Selection and/or screening markers are particularly useful for the preferred two-step retroviral transduction protocol, involving the sequential transduction of immunoglobulin heavy and light chain retroviral expression vectors. In a two-step transduction protocol a vertebrate host cell is first transduced with at least one retroviral expression construct encoding a first immunoglobulin polypeptide chain or chains, and after the first at least one polypeptide chain is stably expressed, a second transduction with at least one retroviral expression construct encoding the corresponding other immunoglobulin polypeptide chain or chains, then allowing generation of a complete antibody or collection of antibodies. If a selection or screening marker is used for the selection or screening for a successful first transduction event, it is very useful to optimize the co-transduction frequencies of at least two retroviral expression constructs encoding separate chains of a multimeric binding protein, like antibodies. The use of selection and/or screening markers is therefore strongly preferred.

Selection markers, conferring resistance to antibiotics useful for the selection of mammalian cells, include, but are not limited to, e.g. genes for puromycin, neomycin, hygromcin B, mycophenolic acid, histidinol, bleomycin, and phleomycin resistance. For the expression of multimeric proteins, like antibodies, encoded by separate retroviral constructs, it is preferable that expression of different polypeptide chains are linked to different selection markers, thereby allowing separate selection for the stable transduction of corresponding expression constructs.

Marker genes, allowing monitoring of retroviral transduction into host cells include, but are not limited to genes, conferring auto-fluorescence to transduced cells, like e.g., but not limited to green fluorescent protein (GFP), enhanced green fluorescent protein (EGFP), yellow fluorescent protein (YFP), blue fluorescent protein (BFP) and red fluorescent protein (RFP). Alternatively, cell surface markers could be used such as CD7 or truncated variants thereof, CD34 or truncated variants thereof, or low affinity nerve growth factor receptor. In a preferred embodiment the expression of these antibiotic selection markers, fluorescence markers or cell surface markers is coupled to the expression of the recombinant binding protein via so-called internal ribosomal entry sequences (IRES), which in vertebrate cells allow the coupled co-expression of two genes from a single promoter element (FIG. 4b). However, a person skilled in the art may also realize the invention by expressing a selection and/or marker gene from a separate expression cassette contained in the retroviral construct, driven by an additional promoter element. For the expression of multimeric proteins, like immunoglobulins, from separate retroviral vectors, it is preferred that different binding protein chains are linked to different selection and/or screening markers, thereby allowing separate monitoring for the stable transduction of the different expression constructs.

In case the expression of the recombinant binding protein is driven by a separate promoter, as outlined above, any selection or screening marker gene can also be cloned downstream of the 5'LTR and downstream of the 5'LTR and ψ packaging signal, such that its expression is driven by the 5'LTR promoter (see FIGS. 3 and 4).

As mentioned above, a preferred embodiment of the invention is to express recombinant antibodies or fragments thereof in cells of the B-lymphocyte lineage, preferably in preB lymphocytes. It is therefore further preferred to drive the expression of recombinant antibodies by promoter and enhancer combinations that are known to confer high-level expression selectively in B-lineage cells. Such promoter/enhancer combinations can be e.g., but not limited to, immunoglobulin κ light chain promoter, κ-intron and 3'κ enhancer combinations, immunoglobulin heavy chain, heavy chain intron and 3'α enhancer combinations. The combination of immunoglobulin κ light chain promoter, κ-intron and 3'κ enhancer combinations is preferred (FIGS. 4a,b), because it is known that this combination allows high level expression of immunoglobulin chains in B lineage cells and because this combination of cis-regulatory genetic elements is able to promote somatic hypermutation to coding regions of antibodies in a regulated fashion, mediated by the activated B cell specific enzyme AID (activation induced cytidine deaminase), which is an embodiment of the invention as detailed further below.

However, any person skilled in the art may appreciate that expression of a particular recombinant antibody in retroviral vectors for realizing the invention may be effected by any combination of cis-regulatory promoter/enhancer elements and coding regions that allows expression the antibody in the desired vertebrate host cell either on the cell surface membrane, or in secreted form.

Although it is a preferred embodiment of this invention to express multimeric binding proteins, such as antibodies, from separate retroviral expression constructs (FIGS. 4a and b), the invention may also be realized, if the expression of different protein chains of multimeric binding proteins is linked on the same retroviral expression construct. In the case of immunoglobulins, this may be accomplished by, but not limited to, expression of the heavy and light chain from one promoter and separating the coding regions for heavy and light chains by IRES sequences. In this alternative, it is preferred to clone the heavy chain directly downstream of the promoter and the light chain downstream of the IRES, because it is known that a gene following the IRES is often expressed at somewhat lower levels than the gene upstream of the IRES. As light chains are the smaller molecules, it is anticipated that a better stoichiometric expression of heavy and light chains expressed via IRES linkage is achieved, if light chain expression is controlled via IRES.

Alternatively, co-expression of two chains of a dimeric binding protein such as an antibody may be achieved by cloning two separate expression cassettes into a single retroviral backbone, such that the expression of each individual binding protein chain is separately controlled. Substitute to this approach, it is also possible to link the expression of two different binding protein chains in the same vector by the use of bi-directional promoters that confer transcriptional activities into opposite directions. The latter option has the potential advantage that promoter interference does not occur, which may negatively affect expression levels of promoters in close proximity.

It should be emphasized that independent from the detailed genetic organization of retroviral vectors harbouring two binding protein coding regions, e.g., heavy and light chain of immunoglobulins, this method allows for a single retroviral gene transfer of binding protein pairs into target cells, which allows for facilitated control of clonal expression of dimeric binding proteins and reduces the time-frame for the generation of a binder expressing cell population, in comparison to a two-step retroviral transduction protocol.

In addition to cis-regulatory genetic elements, like promoters and enhancer, and selectable or screenable marker genes, like antibiotic resistance markers and genes encoding autofluorescent proteins, the coding regions for immunoglobulin heavy and light chains can be cloned into the retroviral expression vectors in different contexts.

In a preferred embodiment of the invention the immunoglobulin heavy and light chain coding regions are cloned into retroviral expression constructs as contiguous cDNA sequences, including leader sequences required for proper surface expression and/or secretion. Examples of the basic design for such expression vectors with enhancer elements are depicted in FIG. 4a. Preferably the heavy chains encode human γ1 heavy chain isotypes and the light chains κ light chain isotypes, however, it is to be understood that any other heavy and light chain isotypes of human or other vertebrate species may be employed in order to realize the invention. In such retroviral cDNA expression vectors it is preferred to include a unique restriction enzyme at the junction between the variable and constant coding regions, which would allow the replacement of only $V_H$ and $V_L$ coding regions in order to alter the specificity of the expressed antibodies, or which allows the insertion of a multitude of $V_H$ and $V_L$ coding regions for the expression of diverse retroviral antibody libraries in the target cells. In a preferred embodiment the restriction enzyme site introduced at the borders of $V_H$—Cγ1 and $V_L$—$C_κ$ is an Eco47III site (FIGS. 4a, b), which does not alter the amino acid composition of the expressed heavy chains and would only lead to a conserved threonine to serine amino acid change at the first position of the constant κ coding region, which does not affect the binding properties of retrovirally expressed human $IgG_1$ molecules.

As an alternative to retroviral constructs containing the coding information for heterologous, preferably fully human antibodies in cDNA configuration, retroviral expression vectors may be employed containing the coding regions in genomic configuration, with the typical exon-intron structure found for immunoglobulin heavy and light chains in the germline. As retroviral vectors will be transcribed into mRNA upon retroviral particle packaging, such an organization of expression constructs requires that the transcriptional organization of the coding regions runs in opposite direction to the transcriptional orientation of the 5'LTR of the retroviral genome, because otherwise the retroviral transfer vector would already be spliced, upon which the exon-intron structure would be lost before transduction and stable integration of the recombinant construct into the target cells. However, these constructs offer the functionality that antibodies may be expressed as either membrane bound or as secreted antibodies, depending on the nature of the target cell for transduction, and the ability of the target cell to either terminate transcription at the internal stop codon for secreted antibodies, or by alternative splicing of a splice donor upstream of the stop codon for secreted antibodies, to splice acceptors of the membrane spanning exons of membrane bound immunoglobulin.

A preferred aspect of the invention is the generation and utilization of retroviral expression constructs for human antibodies or any heterologous antibody or fragment thereof, in which the variable coding region of the heavy and/or the light chain still needs to be assembled in the target cells from V, optionally D, and J gene segments in "quasi-germline" configuration by the process of V(D)J recombination. Illustrations of the basic design of such expression vectors are depicted in FIG. 4 b, which still share the feature of the non-rearrangeable constructs that "germline" V-D-J or V-J cassettes for heavy and light chains can be replaced by unique restriction enzyme sites, including preferably Eco47III at the 3' border of the J-element coding region. The V, D and J-elements contained in such vectors are flanked by conserved recombination signal sequences (RSSs) known to be recognition motifs for the recombination activating genes (RAG) 1 and 2. Upon co-expression of RAG1 and RAG2 in any vertebrate cell, such vectors will site-specifically recombine V, optionally D and J gene segments in order to generate the $V_H$ and $V_L$ regions encoding the variable domains of antibody heavy and light chains, respectively. The expression of RAG-1 and RAG-2 genes, thus V(D)J recombination activity, is normally restricted to early precursor lymphocytes. Therefore, the preferred use of precursor lymphocyte to realize the invention automatically provides the activity for V(D)J recombination. However, it is known that upon RAG-1 and RAG-2 over-expression, any somatic vertebrate cell line can be rendered proficient for V(D)J recombination, and any person skilled in the art may therefore also realize this aspect of the invention with any non-precursor lymphocyte cell line, by conferring ectopic expression of RAG-1 and RAG-2. As an alternative even RAG-1 or RAG-2 deficient cell lines may be employed in which the RAG-1 or RAG-2 deficiency is complemented by overexpression of the corresponding RAG gene or a fragment thereof.

Such V(D)J rearrangeable constructs have the advantage that from a single retroviral expression construct that is stably transduced into a vertebrate host cell a diverse repertoire of antibody specificities can be generated via RAG-1 and RAG-2 mediated V(D)J recombination.

Although it is known that the joining of V, D and J gene elements involves a great degree of imprecision that contributes significantly to the diverse amino acid sequences found in $V_H$ and $V_L$ complementarity determining region $(CDR)_3$, it is preferred to employ a collection of V-D-J-Cγ1 and V-J-Cγ retroviral construct, representing several V-region families, D and J elements, in order to increase the variability already at the level of germline gene segment sequences provided. Nevertheless, would the preferred use of retroviral construct allowing the somatic assembly of V, optionally D, and J gene segments mediated by the process of V(D)J recombination allow the generation of a large diversity of variable domain binding regions upon transduction into precursor lymphocytes in situ, so that diverse collection of IgH and IgL chains can be generated from single or limited numbers of constructs.

The diversity generated by imprecise joining of V, D and J gene segments is greatly increased by the presence of the precursor lymphocyte specifically expressed gene terminal deoxynucleotidyl transferase (TdT), which is the only DNA polymerase that is able to add nucleotides to 3' DNA ends without a complementary template DNA strand. In order to increase junctional diversity it is preferred to either employ cells with high endogenous TdT expression levels, or, alternatively, to ectopically express TdT in the target host cells used for retrocyte display, by methods known in the art.

Another embodiment of the invention is the use of V(D)J rearrangeable retroviral constructs containing more than one V, or D or J gene segment, such that by the process of V(D)J recombination different V, D and J gene segments may be used in different rearranged clones from the same construct. The incorporation of a multitude of different V, D and J gene segments into such constructs is only restricted by the total capacity of retroviral vectors accepting DNA, which is reported to be maximally in the range of 8-10 kilobases.

Although the employment of V(D)J recombination competent retroviral constructs (FIGS. 4a,b lower panels) for the expression of heterologous antibodies or fragments thereof is an aspect of the current invention, it is clear that the generation of a diverse repertoire via this approach is mainly restricted to the generation of diversity in the CDR3 regions of immunoglobulin heavy and light chains, very similar to the characteristic of a primary antibody repertoire generated during early B lymphopoiesis.

A hallmark of the adaptive immune system is its capability of affinity maturation of antibody variable domains, which is based on the somatic hypermutation of variable domain coding regions. Somatic hypermutation is known to be strongly enhanced by the enzyme activation induced cytidine deaminase (AID). High-level somatic hypermutation additionally depends on the presence of cis-regulatory enhancer elements from the immunoglobulin gene locus, and a beneficial effect has most clearly been described for combinations of the Igκ intron and 3'κ enhancer elements. An aspect of the current invention is therefore the employment of retroviral expression constructs containing these cis-regulatory elements to retrovirally express such immunoglobulin expression constructs in target cells endogenously or ectopically expressing the AID enzyme, either constitutively or inducibly, by methods known in the art.

The application of 'Retrocyte Display' in the context of somatic hypermutation competent retroviral constructs and in the context of AID expressing host cells allows for a further diversification of an antibody in situ, after transduction into AID expressing host cells.

The combination of these aspects of the invention recapitulates all molecular and genetic events occurring in the adaptive immune system, namely the generation of a primary antibody repertoire from one or a limited number constructs comprising a limited number of V, D and J gene segments and the additional AID-mediated somatic hypermutation of the coding regions for antigen-binding variable domains of antibodies.

The specific selection of higher affinity antibody binders to desired antigens can be accomplished by Retrocyte Display via increased binding to desired antigens of choice detected by standard FACS based technology, followed by high-speed preparative cell sorting of strong antigen binders. Strong binders can thus be selectively isolated, and the antibody genes encoded by the retroviral vectors can be re-isolated, cloned and sequenced from selected cells or cell clones by standard molecular biology methods, known in the art, including, but not limited to genomic and RT-PCR.

In a preferred embodiment the final cell sorting step is performed as a single cell sort, allowing the clonal isolation and final expansion of antigen reactive cell clones, which facilitates cloning and sequence determination of the coding region of cognate IgH and IgL chain pairs from selected binders.

Figure 1:
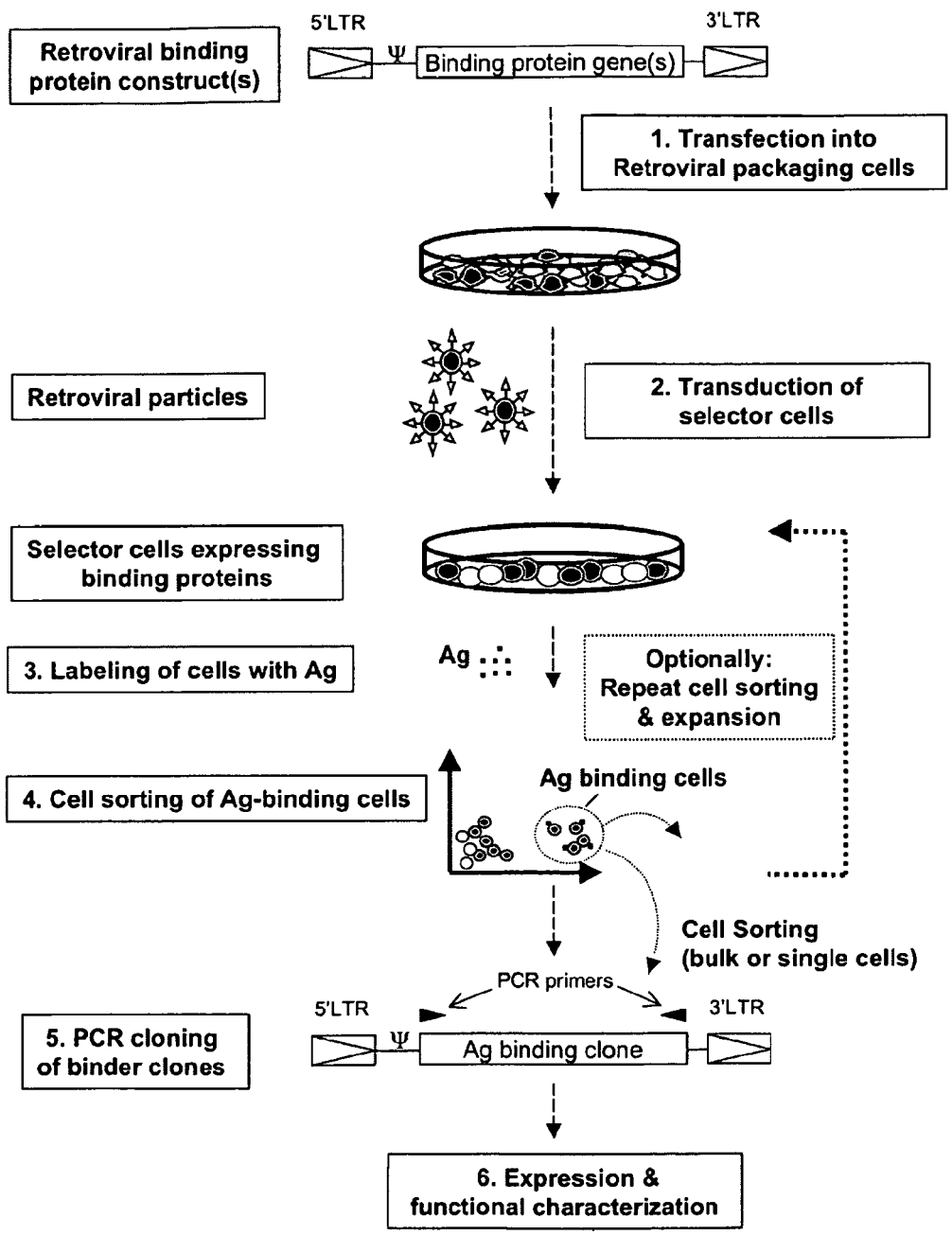
FIG. 1: This figure illustrates the principle of 'Retrocyte Display' allowing the identification and isolation of a binding protein such as an antibody, specific for a desired antigen or ligand. In a first step, at least one retroviral expression construct that can give rise to expression of a diverse collection of binding proteins is stably transduced into suitable vertebrate host cells ("selector cells"). This is accomplished by transfecting at least one retroviral vector encoding at least one binding protein into retroviral packaging cells (step 1), which may either constitutively or transiently express retroviral proteins Gag, Pol and Env. Packaging cells transfected with the at least one retroviral binding protein construct will then produce recombinant retroviral particles within 24-72 hours post transfection, containing the at least one retroviral expression construct. The resulting retroviral particles accumulate in the cell culture supernatant of the retroviral packaging cells, and can be used to transduce suitable vertebrate host cells ("selector cells") (step 2), which then express the binding protein. In the preferred method, the binding proteins such as antibodies or fragments thereof are expressed on the cell surface of the "selector cells" and the cells then are labelled with a desired antigen or ligand (step 3). Antigen- or ligand binding cells are then preferably analyzed by fluorescent activated cell sorting (FACS) and cells that exhibit specific antigen binding, are separated from the non-binding cell population preferably by preparative, high-speed FACS (step 4). Antigen- or ligand reactive cells may optionally be expanded in tissue culture again, and due to the stable expression phenotype of retrovirally transduced cells, cycles of antigen-directed cell sorting and tissue culture expansion may be repeated, up to the point that a detectable antigen- or ligand reactive cell population is obtained. This antigen- or ligand reactive cell population may be subjected to a final, preferable, single-cell sorting step, or may directly be used for cloning of binding protein encoding genes on a population basis. In the next step (step 5), the coding regions of relevant binding domains are cloned from the antigen- or ligand-selected cell pools or cell clones, by RT-PCR or genomic PCR using primer pairs binding to sequences specific for the binding protein library and/or specific for other vector sequences, by standard methods known in the art. Cloned and sequenced coding regions for binding proteins may then optionally be expressed as recombinant proteins in any expression system of choice for further functional characterization and to confirm antigen- or ligand binding specificity (step 6).

If desired, FACS-enriched cells can be expanded in culture and can optionally again be subjected to antigen binding and repeated high-speed cell sorting of highly reactive cells, a process that can optionally be applied repeatedly, until desired staining intensity and hence expected binding specificity for a desired antigen is achieved (FIG. 1). This selective enrichment and in vitro expansion of antigen reactive cells mimic the selective outgrowth of higher affinity binders occurring in T cell dependent immune reactions.

It should be noted that high-speed cell sorter assisted enrichment of antigen-reactive cells is only a preferred method of realizing the invention, but that other ways of selecting and isolating cells for antigen reactivity, like for instance, but not limited to, panning methods, where cells are bound to immobilized antigens on a solid support, may also be applied. Furthermore, it is possible to enrich antigen-reactive cells by micromanipulative approaches, e.g., but not limited to, growing cells under limiting dilution conditions in microtiter plates or as cell clones in semi-solid medium, which allows specific antigen-staining and/or labelling of cell clones and their identification by microscope assisted ways followed by manual and/or roboter assisted picking of antigen reactive clones.

A further embodiment of the invention is to perform repetitive cycles of antigen-selection/FACS-sorting/expansion of antigen-reactive cells in the presence of mutagenizing conditions, specifically targeting mutations to the coding regions of variable antibody binding domains. By this approach higher affinity mutants, which are generated in situ, are generated in each round of cell amplification. Upon cell sorting and enrichment of cells showing increased antigen binding upon retrocyte display, higher affinity mutants can selectively be enriched and expanded. A high mutation rate targeted to antibody variable region domains can be achieved by over-expressing the AID enzyme in the antibody expressing cells, in particular, when the expression constructs contain cis-regulatory promoter and enhancer elements, including, but not limited to immunoglobulin κ intron and 3'κ enhancer elements, that are known to confer AID mediated somatic hypermutation to antibody variable regions (FIGS. 4a and b). While such an approach could be realized using cells that constitutively express AID, either endogenously or ectopically, one aspect of the invention utilises AID expression vectors, in which AID expression can be induced and again switched off using inducible promoters, e.g., but not limited to, tetracycline and/or doxycycline inducible promoter systems (Gossen & Bujard, 1992), in which the expression of a gene of interest is controlled by a minimal CMV promoter flanked by tandem repeats of the prokaryotic tet-operon, and which can be induced or suppressed for expression using a HSV-VP16-Tet-repressor fusion protein, whose binding to the tet-operon is allosterically controlled by tetracycline or tetracycline derivatives.

In the following non-limiting examples, the present invention is explained in more detail.

Example 1

Cloning of Retroviral Expression Vectors for Fully Human Immunoglobulin Heavy (IgH) and Immunoglobulin Light (IgL) Chains Containing HygromycinB and Puromycin Antibiotic Drug Selection Markers, Respectively As mentioned before, the invention can be realized with retroviral expression vectors for binding proteins of different design (compare e.g. FIGS. 4a-c). As an example of one of the vector designs that can be used to realize the invention, the detailed cloning strategy for retroviral expression vectors is described herein allowing the expression of fully human IgG$_1$/κL antibodies, and the selection for the stable maintenance of these vectors in target cells using antibiotic resistance markers.

a) Construction of retroviral expression vectors for human immunoglobulin heavy (IgH) chains As a starting point for construction of retroviral human immunoglobulin heavy expression vectors, the commercially available retroviral vector pLHCX was used (BD-Clontech, Mountain View, Calif.) (FIG. 5a). pLHCX contains an hygromycinB resistance marker gene driven by the 5'LTR promoter of the retroviral backbone. In addition, pLHCX contains the CMV-immediate early promoter followed by simple multiple cloning site (MCS) for insertion of genes of interest to be expressed. In addition, the pLHCX backbone contains a convenient unique BglII restriction enzyme site upstream of the CMV promoter (FIG. 5a), into which additional genetic elements can be cloned.

It is a preferred embodiment of the invention to use the Eco47III restriction enzyme for in-frame cloning of human V$_H$ coding regions to the human constant γ1 heavy chain coding regions, as this particular restriction enzyme site can be introduced at the junction between V$_H$ and Cγ1 coding regions without changing the amino acid composition of expressed IgH chains. However, pLHCX contains one Eco47III restriction enzyme site in the ψ packaging signal (FIG. 5a) that would preclude the straightforward use of Eco47III for the above-mentioned V$_H$ region cloning strategy. In order to remove this inconvenient Eco47III restriction enzyme site from the pLHCX vector backbone, the following first preparatory cloning step was performed as detailed in FIG. 5a. The Eco47III site in the ψ packaging signal was removed by site-directed mutagenesis using a commercial Quikchange™ kit (Stratagene, La Jolla, Calif.) replacing the third C nucleotide of the Eco47III recognition sequence AGCGCT with an A, using specific primer pairs conferring the desired mutation according to the instructions of the manufacturer. The modified vector was designated pLHCX-m1 and it was verified that this single-basepair substitution in the ψ (Psi) packaging signal did not affect the retroviral transduction efficiency of the modified vector pLHCX-m1 (data not shown).

Into the pLHCX-m1 backbone, cDNAs encoding the constant region for human Cγ1 either with or without membrane spanning coding regions M1 and M2 have been cloned in parallel. The Cγ1-m and Cγ1-s DNA fragments were amplified by RT-PCR using cDNA of human peripheral blood lymphocytes as template and forward and reverse primers Seq-ID1, Seq-ID2, Seq-ID3 (see below). For the RT-PCR amplification of the membrane bound form of human IgG, the primer combination Seq-ID1 and Seq-ID2 was used and for the cloning of the secreted version of human IgG, the primer combination Seq-ID1 and Seq-ID3 was used. The forward and reverse PCR amplification primers contained HindIII and ClaI restriction enzyme sites, respectively, allowing directional cloning of the PCR-amplified fragments into the unique HindIII and ClaI sites downstream of the CMV promoter in pLHCX-m1 (FIG. 5a). The forward PCR amplification primer additionally contained an internal Eco47III site useful for in-frame fusion of V$_H$ regions to the constant regions, without changing the amino acid composition of the expressed full-length IgG$_1$ heavy chains. The reverse PCR amplification primers Seq-ID2 and Seq-ID3 contained additional internal NotI sites, which allowing the restriction enzyme digestion of the construct directly downstream of the coding region, for general cloning purposes, e.g. the exchange of the constant region coding region for the expression of different Ig isotypes.

Seq-ID1:
5'-GATCAAGCTTAGCGCTTCCACCAAGGGCCCATCGGTCTTCCC-3'
    HindIII/Eco47III The primer Seq-ID2 was used as a reverse primer for PCR amplification of the secreted version of human IgG$_1$ together with Seq-ID1, and contained a unique NotI site (underlined) for cloning purposes.

Seq-ID2:
5'-GATCATCGATGCGGCCGCTCATTTACCCGGAGACAGGGAGAGG-3'
          ClaI/NotI

The primer Seq-ID3 was used as a reverse primer for PCR amplification of the membrane bound version of human IgG₁ together with Seq-ID1, and contained a unique NotI site (underlined) for cloning purposes.

Seq-ID3:
5'-GATCATCGATGCGGCCGCTAGGCCCCCTGCCTGATCATGTTC-3'
          ClaI/NotI

The resulting PCR-products of ca. 1.0 kb for the secreted version of human Cγ1 and of ca. 1.2 kb for the membrane bound version of human Cγ1 were digested with HindIII and ClaI restriction enzymes and were in parallel directionally cloned into the compatible restriction enzyme sites pLHCX-m1, resulting in plasmids pLHCX-m1-Cγ1-s and pLHCX-m1-Cγ1-m, respectively (see also FIG. 5b). $V_H$ chain regions could then be cloned in-frame to the coding regions for secreted or membrane-bound human Cγ1 using unique restriction enzymes HindIII and Eco47III, flanking $V_H$ region fragments (FIG. 5b). This combination of restriction enzymes is only very rarely found in human $V_H$ coding regions of all 7 human V-gene segment families.

In order to construct a complete human IgG1 heavy chain expression vector, a human $V_H$ coding region from a previously identified fully human antibody, specific for NIP-Ovalbumin, was inserted into the constructs pLHCX-m1-Cγ1s and pLHCX-m1-Cγ1m as a HindIII-Eco47III fragment resulting in plasmids pLHCX-m1-VHCγ1s and pLHCX-m1-VHCγ1m, respectively (FIG. 5c). The $V_H$ coding region for the NIP-Ovalbumin specific human antibody including leader sequence and 5'-HindIII and 3'Eco47III cloning sites is provided in Seq-ID4. It should be noted that two additional C nucleotides had been added upstream of the start-ATG for improved translation (approximation of a Kozak-consensus sequence):

Seq-ID4:
AAGCTTCCATGGAGTTTGGGCTcAGCTGGGTTTTCCTTGTTGCTCTT

TTAAGAGGTGTCCAGTGTCAGGTGCAGCTGGTGGAGTCTGGGGGAGG

CGTGGTCCAGCCTGGGAGGTCCCTGAGACTCTCCTGTGCAGCCTCTG

GATTCACCTTCAGTAGCTATGCTATGCACTGGGTCCGCCAGGCTCCA

GGCAAGGGGCTGGAGIGGGIGGCAGTTATATCATATGATGGAAGCAA

TAAATACTACGCAGACTCCGTGAAGGGCCGATTCACCATCTCCAGAG

ACAATTCCAAGAACACGCTGTATCTGCAAATGAACAGCCTGAGAGCT

GAGGACACGGCTGTGTATTACTGTGCGAGAATGGTCGACCACGCGGA

AAGCTACTACTACTACTACGGTATGGACGTCTGGGGCCAAGGGACAA

TGGTCACCGTCTCTAGCGCT

HindIII and Eco47III restriction enzyme sites for cloning are underlined in Seq-ID4. The start ATG of the leader sequence starts at position 9.

While this human IgG₁ heavy chain expression vectors depicted in FIG. 5c are already sufficient to realize the invention and to perform retrocyte display in combination with retroviral IgL chain expression vectors, the functionality of targeting somatic hypermutation to $V_H$ coding regions requires the presence of certain cis-regulatory enhancer elements of the immunoglobulin light or heavy chain gene loci. As the κ intron and 3'κ enhancer elements of the κ light chain gene locus are known to be capable of targeting somatic hypermutation to V regions located downstream of an active promoter, the basic retroviral human Ig heavy chain expression vectors pLHCXm1-VHCg1m and pLHCXm1-VHCg1s (FIG. 5c) have additionally been modified to contain κ intron and 3'κ enhancer elements in the following way. The sequence of the murine κ intron enhancer (κiE) is located within a ca. 2.3 kb long intergenic region located between the Jκ5 element and the constant κ coding region, whose sequence can de derived from NCBI-Genbank entry V00777. The core κiE comprises only about 0.5 kb within this intergenic region and its sequence can be derived from NCBI Genbank entry X00268. The entire 2.3 kb fragment from Jκ5 to Cκ, including the κiE region, contains an internal BglII site, precluding the use of this restriction enzyme for cloning of a PCR amplified genomic fragment into the pLHCX-m1-VHCγ1-s and pLHCX-m1-VHCγ1-m vectors. However, there is no internal BamHI restriction enzyme fragment in this region, therefore allowing the cloning of a genomic PCR fragment flanked by BamHI site into BglII linearized vectors pLHCX-mod 1-VHCγ1s and pLHCX-m1-VHCγ1m (FIG. 5c). Vectors have been constructed containing both the entire ca. 2.3 kb intergenic region between Jκ5 to Cκ by PCR amplification of this genomic fragment from mouse genomic DNA using forward and reverse primers Seq-ID5 and Seq-ID6, both containing additional BamHI restriction enzyme sites (underlined) for cloning into the unique BglII restriction enzyme site of pLHCX-m1-VHCγ1s and pLHCX-m1-VHCγ1m, resulting in plasmids pLHCX-m1-VHCγ1s-κiE and pLHCX-m1-VHCγ1m-κiE, respectively (FIG. 5d).

Seq-ID5:
5'-GATCGGATCCGTACACTTTTCTCATCTTTTTTTATGTG-3'
        BamHI

Seq-ID6:
5'-GATCGGATCCCTGAGGAAGGAAGCACAGAGGATGG-3'
        BamHI

In addition to inserting the entire ca. 2.3 kb κiE containing genomic fragment from the mouse κ light chain gene locus, also a shorter, ca. 0.8 kb genomic PCR fragment (position 3634-4394 of V00777, Seq-ID7), containing the core κiE has been cloned into the unique BglII site of pLHCX-m1-VHCγ1-s and pLHCX-m1-VHCγ1-m (not shown). The forward and reverse PCR primers used for PCR amplification of this genomic DNA fragment are depicted in Seq-ID8 and Seq-ID9.

Seq-TD7:
5'-GAAAAATGTTTAACTCAGCTACTATAATCCCATAATTTTGAAA
ACTATTTATTAGCTTTTGTGTTTGACCCTTCCCTAGCCAAAGGCAA
CTATTTAAGGACCCTTTAAAACTCTTGAAACTACTTTAGAGTCATT
AAGTTATTTAACCACTTTTAATTACTTTAAAATGATGTCAATTCCC
TTTTAACTATTAATTTATTTTAAGGGGGGAAAGGCTGCTCATAATT
CTATTGTTTTCTTGGTAAAGAACTCTCAGTTTTCGTTTTTACTAC
CTCTGTCACCCAAGAGTTGGCATCTCAACAGAGGGGACTTTCCGAG
AGGCCATCTGGCAGTTGCTTAAGATCAGAAGTGAAGTCTGCCAGTT
CCTCCAAGGCAGGTGGCCCAGATTACAGTTGACCTGTTCTGGTGTG
GCTAAAAATTGTCCCATGTGGTTACAAACCATTAGACCAGGGTCTG
ATGAATTGCTCAGAATATTTCTGGACACCCAAATACAGACCCTGGC
TTAAGGCCCTGTCCATACAGTAGGTTTAGCTTGGCTACACCAAAGG
AAGCCATACAGAGGCTAATATCAGAGTATTCTTGGAAGAGACAGGA
GAAAATGAAAGCCAGTTTCTGCTCTTACCTTATGTGCTTGTGTTCA

```
-continued
GACTCCCAAACATCAGGAGTGTCAGATAAACTGGTCTGAATCTCTG
TCTGAAGCATGGAACTGAAAAGAATGTAGTTTCAGGGAAGAAAGGC
AATAGAAGGAAGCCTGAGAATATCTTCAAAGGG-3'

Seq-ID8:
5'-GATCGGATCCGAAAAATGTTTAACTCAGCTAC-3'
     BamHI

Seq-ID9:
5'-GATCGGATCCCCCTTTGAAGATATTCTCAGGCTTCC-3'
     BamHI
```

The ca. 0.8 kb fragment core κiE containing genomic PCR fragment was also cloned as a BamHI digested PCR fragment both into the unique BglII restriction enzyme site of vectors pLHCX-m1-VHCγ1-s and pLHCX-m1-VHCγ1-m (not shown here).

The sequence of the murine 3'κ enhancer element deposited can be retrieved under NCBI-Genbank reference number X15878, and is contained in an 808 bp gene sequence located ca. 8.7 kb downstream of the constant κ coding region in the mouse genome.

The murine 3'κ enhancer does not contain an internal ClaI site and was therefore PCR-amplified from mouse genomic DNA using forward and reverse PCR primers Seq-ID10 and Seq-ID11, respectively, containing additional ClaI restriction enzyme sites for cloning into the unique ClaI site of retroviral vectors pLHCX-m1-VHCγ1s-3'κ E and pLHCX-m1-VHCγ1m-3'κ E (FIG. 5d).

```
Seq-ID10: 5'-GAGAATCGATAGCTCAAACCAGCTTAGGCTACAC-3'
              ClaI

Seq-ID11: 5'-GAGAATCGATTAGAACGTGTCTGGGCCCCATG-3'
              ClaI
```

This resulted in the final Igγ₁H chain expression vectors pLHCX-m1-VHCγ1s-3'κE-κiE and pLHCX-m1-VHCγ1m-3'κE-κiE (FIG. 5e) encoding either Ig heavy chains that, upon IgL chain co-expression, lead to the production of secreted or to membrane bound human IgG₁ antibodies, respectively.

Both vectors additionally contain κiE and 3'κE cis regulatory elements upstream and downstream of the Igγ₁H chain expression cassette, conferring somatic hypermutation to the V$_H$ regions of the expressed Igγ₁H chains.

b) Cloning of retroviral expression vectors for human Igκ light chains

As a starting point for construction of retroviral human immunoglobulin light chain expression vectors allowing antibiotic selection for retroviral integration, the commercially available retroviral vector pLPCX (BD-Clontech, Mountain View, Calif.) has been used (FIG. 6a). This vector contains an antibiotic selection marker conferring puromycin resistance, driven by the 5'LTR promoter of the retroviral backbone. Although similar in design as the pLHCX backbone (see Example 1a), pLPCX contains two Eco47III sites and a MCS with more restriction enzyme sites, but lacks the convenient unique BglII site upstream of the CMV promoter (FIG. 6a).

In order to remove the Eco47III restriction enzymes from the pLPCX vector backbone and at the same time to introduce a unique BglII restriction enzyme upstream of the CMV promoter, the following preparatory cloning steps were performed: In a first step, the Eco47III sites in the packaging signals of pLHCX was removed by site-directed mutagenesis using a commercial Quikchange™ kit (Stratagene, La Jolla, Calif.) replacing the third C nucleotide of the Eco47III recognition sequence AGCGCT with an A, using specific primer pairs conferring the desired mutation according to the instructions of the manufacturer (FIG. 6a). It was verified that this single-base pair substitution in the ψ (Psi) packaging signal did not affect the retroviral transduction efficiencies of the mutated vectors (data not shown). The mutated vector was designated pLPCX-m1 (FIG. 6a). In order to obtain a pLPCX vector backbone completely devoid of Eco47III sites and additionally including a unique BglII site upstream of the CMV promoter, an AscI-NcoI fragment from pLPCX-m1, in which the NcoI digested DNA end had been filled-in by Klenow enzyme, was cloned into an AscI-BlpI digested pLHCX backbone, in which the BlpI digested DNA end had been filled in by Klenow enzyme (FIG. 6b), thereby generating a vector designated pLPCX-m2, in which essentially only the hygromycinB gene of pLHCX had been replaced by the puromycin resistance marker of pLPCX (FIG. 6b).

For the construction of the IgκL chain expression vector, the constant κ light chain coding region was PCR cloned from human peripheral blood lymphocyte cDNA using forward and reverse primers Seq-ID12 and Seq-ID13, containing HindIII and ClaI restriction enzyme sites, respectively for directional cloning into pLPCX-m2 (FIG. 6b). As described under section a.), the forward primer Seq-ID12 additionally contained an Eco47III site allowing in-frame fusion of V$_L$ coding regions to the constant κ light chain coding region, only resulting in one conserved threonine to serine amino acid substitution at the first position of the human constant κ light chain. The reverse primer contained an additional internal NotI site to facilitate later cloning procedures, like e.g. the exchange of the constant κ coding region.

```
Seq-ID12:
5'-GATCAAGCTTAGCGCTCTGTGGCTGCACCATCTGTCTTCATC-3'
       HindIII/Eco47III Seq-ID13:
5'-GATCATCGATGCGGCCGCCTAACACTCTCCCCTGTTGAAGCT-3'
       ClaI/NotI
```

The insertion of the constant κ light chain coding region flanked by HindIII/Eco47III sites at the 5' end and NotI/ClaI sites at the 3' end into pLPCX-m2 resulted in plasmid pLPCX-m2-Cκ.

In order to construct a complete human IgκL heavy chain expression vector, a human Vκ coding region from a previously identified fully human antibody, specific for NIP-Ovalbumin, was inserted into the construct pLPCX-m2-Cκ as a HindIII-Eco47III fragment (FIG. 6c). The Vκ coding region for the NIP-Ovalbumin specific human antibody including leader sequence and 5'-HindIII and 3'Eco47III cloning sites is provided in Seq-ID14. It should be noted that two additional C nucleotides had been added upstream of the start-ATG for improved translation (approximation of a Kozak-consensus sequence):

```
Seq-ID14:
5'-AAGCTTCCATGGATATGAGGGTCCCCGCTCAGCTCCTGGGGCTCCTG

CTACTCTGGCTCCGAGGTGCCAGATGTGACATCCAGATGACCCAGTCTCC

ATCCTCCCTGTCTGCATCTGTAGGAGACAGAGTCACCATCACTTGCCGCG

CAACTCACACCATTACCAGCTATTTAAATTCCTATCACCAGAAACCAGGG

AAAGCCCCTAAGCTCCTGATCTATGCTGCATCCAGTTTGCAAAGTGGGGT

CCCATCAAGGTTCAGTGGCAGTGGATCTGGGACAGATTTCACTCTCACCA

TCAGCAGTCTGCAACCTGAAGATTTTGCAACTTACTACTGTcAACAGAGT
```

-continued

```
TACAGTACCCCCACTTTCGGCCAAGGGACCAAGGTGGAAATCAAGCGC
T-3'
```

HindIII and Eco47III restriction enzyme sites for cloning are underlined in Seq-ID14. The start ATG of the leader sequence starts at position 9. Insertion of this HindIII-Eco47111 fragment into HindIII-Eco47III linearized pLPCX-m2-Cκ resulted in expression construct pLPCX-m2-VκCκ (FIG. 6c).

While this retroviral κ light chain expression vector is already sufficient to realize the invention and to perform retrocyte display upon co-expression with retroviral Ig heavy chain expression vectors, additional vectors have been cloned also containing κiE and 3'κE elements, following the same cloning strategy as for the Ig heavy chain expression constructs. Thus, the mouse κiE was inserted into the unique BglII site in pLPCX-m2-Vκ-Cκ, upstream of the CMV promoter, either as a ca. 2.3 kb genomic, BamHI digested PCR fragment amplified with primer pairs Seq-ID5 and Seq-ID6 (see above), or as a ca. 0.8 kb genomic, BamHI digested PCR fragment amplified with primer pairs Seq-ID8 and Seq-ID9 (see above). Only the cloning of the ca. 2.3 kb genomic mouse κiE containing fragment into pLPCX-m2-VκCκ is depicted here, resulting in plasmid pLPCX-m2-VκCκ-κiE (FIG. 6d).

Finally, and in analogy to the construction κiE and 3'κE containing IgH chain retroviral expression vectors described in Example 1a above, the murine 3'κE was inserted as a ClaI digested genomic PCR fragment amplified with primer pairs Seq-ID10 and Seq-ID11 into the unique ClaI restriction site downstream of the κ light chain coding region in order to generate the retroviral expression vector pLPCX-m2-Vκ-Cκ-κiE-3'κE (FIG. 6d).

Like the IgH chain expression vector containing κiE and 3'κE elements, this vector now contains all cis-regulatory elements required to confer somatic hypermutation to any Vκ coding region cloned into the construct (see below).

Example 2

Generation of a Cell Line Over-Expressing Activation Induced Cytidine Deaminase (AID)

It has been demonstrated that the activated B cell specific protein activation induced cytidine deaminase (AID) is a unique trans-activating factor that is required and sufficient to confer a somatic hypermutation phenotype to any vertebrate cell line. In cells expressing AID, somatic hypermutation can specifically be targeted to transcriptionally active gene loci, if they are arranged in correct context to cis-regulatory enhancer elements, in particular κiE and 3'κE elements of the immunoglobulin κ light chain locus. In order to obtain cell lines stably expressing AID, first, a retroviral expression construct encoding murine AID was constructed in the following way:

The murine AID cDNA was PCR amplified using high-fidelity Pfx-polymerase (Invitrogen, Carlsbad, Calif.) from total mouse spleen cDNA according to the instruction of the manufacturer, using forward and reverse PCR primers Seq-ID15 and Seq-ID16, containing additional XhoI cloning sites for ligation of the PCR amplified fragment into compatible vectors. In addition, the forward primer contained additional two C nucleotides (highlighted in italics) downstream of the XhoI site and upstream of the start ATG codon of the murine AID ORF, in order to approximate a Kozak translational initiation sequence and thereby ensuring proper translation of the cloned cDNA.

```
Seq-ID15:
5'-AATACTCGAGCCATGGACAGCCTTCTGATGAAGCAAAAG-3'
      XhoI

Seq-ID16:
5'-AATACTCGAGTCAAAATCCCAACATACGAAATGCATC-3'
      XhoI
```

The resulting 620 bp RT-PCR product was digested with XhoI and was ligated into XhoI digested and alkaline phosphatase treated pLPCX, from BD-Clontech (Mountain View, Calif.). Ligation products containing the insert in correct orientation were determined by diagnostic restriction enzyme digestion. A clone with correct restriction enzyme pattern containing the murine AID cDNA insert in correct orientation was verified by DNA sequencing and was designated pLPCX-mAID and (FIG. 7).

The sequence of the murine AID cDNA cloned corresponded exactly to the published murine AID cDNA ORF provided in NCBI-Genbank entry AF132979.

Next, 10 μg of PvuI linearised pLPCX-mAID construct was transfected into 5×10$^6$ FA-12 Abelson transformed preB cells resuspended in 800 μl plain RPMI medium by electroporation at 300V, 960 μF at ambient temperature. Transfected cells were resuspended in 20 ml growth medium containing FCS and were plated into ten 96 well plates at 200 μl/well. 48 hours post transfection, stably transfected cells were selected by adding 2 μg/ml puromycin antibiotic to the growth medium.

After 10-14 days post transfection, dozens of puromycin resistant colonies were detectable and selected clones were transferred into fresh culture medium containing 2 μg/ml puromycin. The puromycin resistant clones were further expanded and a selected number of clones were tested for expression of murine AID protein by ECL Western-blotting using a commercial anti-mouse AID antibody as recommended by the manufacturer (see FIG. 9a).

A specific AID protein band was detectable in ca. 80% of the analyzed FA-12-AID transfected cell clones and displayed an apparent molecular weight of 25 kD, as expected. From this it was concluded that several cell lines were obtained constitutively over-expressing the murine AID protein.

Example 3

Demonstration of Somatic Hypermutation Targeted to a Reporter Gene in Retroviral Human Immunoglobulin Expression Constructs Containing Cis-Regulatory κiE and 3'κE Elements Next, it was demonstrated, that human antibody variable regions in retroviral expression constructs, as disclosed in this invention, are targets for AID mediated somatic hypermutation. For this, a reporter construct was generated, in which the V-region ORF of a human IgH chain was replaced with a mutated EGFP ORF, in which a stop codon had been introduced in the context of a RGYW sequence motif that is known to be a hotspot for somatic hypermutation (Bachl & Olsson, 1999).

The stop mutation was introduced at codon 107 of the EGFP ORF changing a tyrosine codon to a TAG stop codon. In addition, codon 108 was modified, thereby generating a novel diagnostic SpeI restriction site within in the mutated EGFP sequence, such that upon reversion of the stop-mutation in codon 107 the SpeI site would be destroyed, thereby facilitating the identification and characterization of revertants. The sequence modification introduced into the EGFP ORF is depicted in FIG. 10a, the entire mutated EGFP ORF is provided in FIG. 10b.

The reporter construct for demonstrating somatic hypermutation was constructed as follows:

The EGFP ORF was PCR amplified from plasmid pIRES-EGFP (BD-Clontech, Mountain View, Calif.) as a template with high-fidelity Pfx-Polymerase (Invitrogen, Carlsbad, Calif.) and forward primers Seq-ID17 and Seq-ID18, each containing additional HindIII and Eco47III restriction enzyme sites allowing replacement of the $V_s$-region in pLH-CXm1-VHCγ-s-κiE-3'κE with a EGFP ORF. The forward primer contained additional two C nucleotides upstream of the ATG start-codon, highlighted in italics, which approximates a Kozak translation initiation consensus sequence and ensures proper translational initiation at the correct ATG start codon.

```
Seq-ID17:
5'-CGCAAGCTTCCATGGTGAGCAAGGGCGAGGAGCTGTTC-3'
     HindIII

Seq-ID18:
5'-TAGAGCGCTCTTGTACAGCTCGTCCATGCCGAGAGTG-3'
     Eco47III
```

The Pfx amplified EGFP PCR fragment of 737 bp was directly cloned into the pCR4-Topo vector, which is part of a Zero-Blunt PCR cloning kit (Invitrogen, Carlsbad, Calif.) resulting in the pCR4-Topo-EGFP vector (FIG. 11). Next, a sequence-verified clone of pCR4-Topo-EGFP was mutated at codons 107 and 108 of the EGFP ORF as depicted in FIG. 10 using a Quikchange™ kit (Stratagene, La Jolla, Calif.) according to the manufacturer's instructions using specific primer pairs conferring the desired mutations, thereby generating plasmid pCR4-Topo-EGFPmut.

The sequence verified, mutated EGFP ORF of pCR4-Topo-EGFPmut was recovered from the plasmid by double restriction enzyme digestion using restriction enzymes HindIII and Eco47111. The digested fragment was ligated into HindIII and Eco47III double digested plasmid pLHCXm1-VHCγ-s-κiE-3'κE (FIG. 5e) and into HindIII and Eco47III double digested plasmid pLHCXm1-VHCγ-s (FIG. 5c), not containing enhancer elements. Thereby, in both vectors the $V_H$ coding regions were replaced with the mutated EGFP ORF, which were fused in-frame to the $C\gamma_1$ regions, resulting in reporter plasmid pLHCXm1-E(mut)-Cγ-s-κiE-3'κE, and in control reporter plasmid pLHCXm1-E(mut)-Cγ-s (FIG. 11).

Both plasmids were transduced into puromycin-resistant FA-12 AID transfectant clones 3 (AID expressing) and 5 (no AID expression) as control. Transduced cells were cultured under 2 mg/ml hygromycin B selection beginning 24 hours after transduction, and cells were analyzed for emergence of green auto-fluorescent cells after 6, 8 and 10 days of culture. Only in the experiment, in which a mutated EGFP reporter construct was expressed in the context with κiE and 3'κE (i.e. using plasmid pLHCXm1-E(mut)-Cγ-s-κiE-3'κE) and in FA-12 AID transfectant, in which AID expression was detectable by Western-blotting (i.e. FA-12 AID transfectant clone3), could green auto fluorescent cells be detected after 6, 8 and 10 days of culture, when a steady-state frequency of ca. 0.2% (FIG. 9b) green cells were detectable by FACS. In none of the control experiments (no AID expression, and/or no enhancer elements present in the constructs, data not shown), could green cells be detected within the 10 days duration of the experiment.

From the 0.2% EGFP positive population, 192 single cells were sorted into individual wells of two 96 wells, and 100 clones from these single-sorted clones were analyzed by FACS for green fluorescence after sufficient cells had been grown up. From 100 clones analyzed, 95 clones displayed a homogenous fluorescence pattern, similar in intensity as the fluorescence detected in the single-sorted cells, i.e. at ca. $10^2$ log fluorescence (auto fluorescence of FA-12 cells control cells remained below the $10^1$ log fluorescence levels, indicated by the threshold-line). 4 clones displayed a heterogeneous fluorescence pattern with ca. half of the cells being negative and half of the cells being positive for EGFP expression. Only one out of 100 clones analyzed displayed practically no EGFP fluorescence, although also this clone was slightly above background auto-fluorescence levels. The 5 clones with heterogeneous and negative EGFP pattern could be due to (partial) positional silencing of EGFP expression of retroviral integrants, or the results could be due to single cell sorting artefacts. Nevertheless, in the majority of clones (95%) EGFP expression was clearly detectable. 24 of these clones were analyzed by PCR using the cloning primers Seq-ID17 and Seq-ID18 in order to re-amplify the EGFP gene from the stably transduced cells.

In contrast to a PCR product from the reporter vector containing the mutated EGFP ORF, none of the 24 PCR products from EGFP expressing clones could be digested with SpeI restriction enzyme, suggesting a reversion of the TAG stop mutation in codon 107 of the mutated EGFP ORF (data not shown).

Ten of the PCR products have been analyzed by DNA sequencing, confirming that all of the ten clones contained a G->C mutation of the G nucleotide in the RGYW motif introduced into the EGFP ORF, as described before in the literature (Bachl & Olsson, 1999).

This demonstrates, that dependent on the presence of cis-regulatory genetic elements, like κiE and 3'κE elements, and dependent on AID expression, elevated levels of somatic mutation, and thus mutagenesis, can be targeted to the DNA regions downstream of an active promoter, and, thus, to the $V_H$ coding regions of human antibody chains in the context of the disclosed retroviral expression constructs.

In terms of estimating the level of AID dependent somatic mutation in the κiE and 3'κE constructs, the estimated mutation rate was in the range of ca. 3×10 mutations/bp/generation. This value is still lower as somatic hypermutation rates that have been reported in vivo which can reach rates of up to $10^{-4}$ or even $10^{-3}$/bp/generation. Nevertheless, the detected mutation rate was still significantly higher than the background mutation rate reported in vertebrate cells that is estimated to be in the range of $10^{-8}$ mutations/bp/generation. Thus, it is concluded that high somatic mutation rates are specifically targeted to regions downstream of an active promoter in the disclosed retroviral constructs in an enhancer and AID dependent fashion, thereby allowing the application of Retrocyte Display under in vivo mutagenizing conditions based on somatic hypermutation mediated by AID expression.

Example 4

Demonstration of In Situ Generation of Human Antibody Encoding Regions by Using V(D)J Recombination Competent Retroviral Expression Vectors a) Cloning of a Retroviral Human Heavy (IgH) Chain Expression Vector Requiring V(D)J Recombination Prior to IgH Chain Expression.

As an alternative approach to retrovirally expressing heavy (H) and light (L) chains from cDNA expression vectors described in Example 1, a different retroviral IgH chain vector class has been constructed, in which the variable coding region is encoded by separate V, D and J gene segments in "quasi-germline" configuration, that still need to be assembled by the process of V(D)J recombination prior to expression. V(D)J recombination mediates site specific, but slightly imprecise assembly of V, D and J gene segments, such that diverse V coding regions can be generated from a single expression construct upon transduction into V(D)J recombination active cells in situ, like e.g. precursor B cells.

For this, germline $V_H3.30$, $D_H1.26$ and $J_H3$ gene segments have been PCR cloned individually from genomic DNA derived from B cell depleted human peripheral blood mononuclear cells (PBMCs). The PCR primers used for the amplification of the germline V, D and J gene segments were chosen such that flanking DNA sequences comprising conserved recombination signal sequences (RSSs) and additional intervening DNA sequences were included allowing proper assembly of V, D and J gene segments. All PCR amplicons were generated using proofreading thermostable DNA polymerase Pfx (Invitrogen, Carlsbad, Calif.) and were initially subcloned into a pSC-B PCR cloning vector (Stratagene, La Jolla, Calif.), in both cases according to the instruction of the suppliers. PCR fragments, subcloned into pSC-B, were verified by DNA sequencing and fragments were only used for further cloning, if the DNA sequence had been sequence verified.

For the PCR amplification of a germline human $V_H3.30$ fragment, DNA primers Seq-ID19 and Seq-ID20 were used containing BamHI and NheI restriction enzyme sites (as indicated) allowing further subcloning of the PCR cloned DNA fragments.

```
Seq-ID19:  5'-ATTTGGATCCCACCATGGAGTTTGGGCTGAGCTGGGTTTTCCTCG-3'
                BamHI
Seq-ID20:  5'-CCCGCTAGCTCCTGACAGGAAACAGCCTCCATCTGCACCT-3'
              NheI
```

This way a PCR amplicon of 623 bp length containing the germline VH3.30 gene segment with flanking DNA was obtained (Seq-ID21), see FIG. 11a.

```
Seq-ID21:
5'atttGGATCCCACCATGGAGTTTGGGCTGAGCTGGGTTTTCCTCGTTG
CTCTTTTAAGAGGTGATTCATGGAGAAATAGAGAGACTGAGTGTGAGTGA
ACATGAGTGAGAAAAACTGGATTTGTGTGGCATTTTCTGATAACGGTGTC
CTTCTGTTTGCAGGTGTCCAGTGTCAGGTGCAGCTGGTGGAGTCTGGGGG
AGGCGTGGTCCAGCCTGGGAGGTCCCTGAGACTCTCCTGTGCAGCCTCTG
GATTCACCTTCAGTAGCTATGCTATGCACTGGGTCCGCCAGGCTCCAGGC
AAGGGGCTAGAGTGGGTGGCAGTTATATCATATGATGGAAGTAATAAATA
CTACGCAGACTCCGTGAAGGGCCGATTCACCATCTCCAGAGACAATTCCA
AGAACACGCTGTATCTGCAAATGAACAGCCTGAGAGCTGAGGACACGGCT
GTGTATTACTGTGCGAGAGACACAGTGAGGGGAAGTCATTGTGCGCCCAG
ACACAAACCTCCCTGCAGGAACGCTGGGGGGAAATCAGCGGCAGGGGGCG
CTCAGGAGCCACTGATCAGAGTCAGCCCTGGAGGCAGGTGCAGATGGAGG
CTGTTTCCTGTCAGGAGCTAGCggg3'
```

Next, PCR amplification of a human genomic DNA fragment containing the human DH1.26 fragment with flanking genomic DNA was achieved using primer pair Seq-ID22 and Seq-ID23, containing sites for restriction enzymes NheI and XhoI, respectively (FIG. 11a).

```
Seq-ID22:
  5'-GGAGCTAGCGGGCTGCCAGTCCTCACCCCACACCTAAGGT-3'
        NheI

Seq-ID23:
  5'-GGGCTCGAGTCCTCACCATCCAATGGGGACACTGTGGAGC-3'
        XhoI
```

This way a PCR amplicon of 336 bp length containing the germline DH1.26 gene segment with flanking DNA was obtained (Seq-ID24).

```
Seq-ID24:
5'ggaGCTAGCGGGCTGCCAGTCCICACCCCACACCTAAGGTGAGCCACA
GCCGCCAGAGCCTCCACAGGAGACCCCACCCAGCAGCCCAGCCCCTACCC
AGGAGGCCCCAGAGCTCAGGGCGCCTGGGTGGATTCTGAACAGCCCCGAG
TCACGGTGGGTATAGTGGGAGCTACTACCACTGTGAGAAAAGCTATGTCC
AAAACTGTCTCCCGGCCACTGCTGGAGGCCCAGCCAGAGAAGGGACCAGC
CGCCCGAACATACGACCTTCCCAGACCTCATGACCCCCAGCACTTGGAGC
TCCACAGTGTCCCCATTGGATGGTGAGGACTCGAGccc3'
```

Last, PCR amplication of a human genomic DNA fragment containing the human JH3 fragment with flanking genomic DNA was achieved using primer pair Seq-ID25 and Seq-ID26, containing sites for restriction enzymes SalI and XbaI/HindIII, respectively, as indicated (FIG. 11a). ment into the BamHI-NheI linearised shuttle vector, then NheI-XhoI digested fragment Seq-ID24 was ligated into Seq-ID25: 5'-GGAGTCGACCCCTGCCTGGGTCTCAGCCCGGGGGTCTGTG-3'
              SalI Seq-ID26: 5'-TATATCTAGAATATAAGCTTAGCCATCTTACCTGAAGAGACGGTGACC-3'
                XbaI     HindIII This way a PCR amplicon of 239 bp length containing the germline JH3 gene segment with flanking DNA was obtained (Seq-ID27).

Seq-ID27:
5'ggaGTCGACCCCTGCCTGGGTCTCAGCCCGGGGGTCTGTGTGGCTGGG

GACAGGGACGCCGGCTGCCTCTGCTCTGTGCTTGGGCCATGTGACCCATT

CGAGTGTCCTGCACGGGCACAGGTTTGTGTCTGGGCAGGAACAGGGACTG

TGTCCCTGTGTGATGCTTTTGATATCTGGGGCCAAGGGACAATGGTCACC

GTCTCTTCAGGTAAGATGGCAAGCTTatatTCTAGAtata3'

The three DNA fragments Seq-ID21, Seq-ID24 and Seq-ID27 have been cloned sequentially into a shuttle vector containing unique BamHI, NheI, XhoI and XbaI restriction enzyme sites, such that a cassette containing gene segments VH3.30, DH1.26 and JH3 could be assembled by sequential ligation of the DNA fragments via the compatible restriction enzyme sites. Seq-ID21 was ligated as a BamHI-NheI fragment into BamHI-NheI linearised shuttle vector. Seq-ID24 was ligated as a NheI-XhoI fragment into NheI-XhoI linearised shuttle vector, already containing Seq-ID21, and last, SalI-XbaI digested fragment Seq-ID27 was ligated into XhoI-XbaI linearised shuttle vector already containing cloned Seq-ID21 and Seq-ID24, thereby generating an artificial VH3.30-DH1.26-JH3 cassette in a shuttle vector (FIG. 11a).

The entire "quasi-germline" cassette containing the artificially assembled VH3.30, DH1.26 and JH3 gene segments was then cloned into the retroviral vector MigR1 (Pear et al. 1998) already containing the coding region for a human pH chain (Seq-ID28, see below) cloned into the unique BglII and HpaI sites of the MigR1 vector (construct MigR1-muH, FIG. 11b). A unique XhoI site separating the VH coding region from the constant pH chain coding region in MigR1-muH (highlighted in boldface print in the middle of Seq-ID28) could be used to ligate the VH3.30-DH1.26-JH3 cassette in-frame to the constant pH chain coding region, without affecting the amino acid sequence at the transition form JH to the constant coding region.

Seq-ID28:
5'AGATCTACCATGGAGTTTGGGCTGAGCTGGGTTTTCCTTGTTGCGATTTTAGAAGGTGTC

CAGTGTGAGGTGCAGCTGGTGGAGTCTGGGGGAGGCTTGGTACAGCCCGGCAGGTCCCTGAG

ACTCTCCTGTGCGGCCTCTGGATTCACCTTTGATGATTATGCCATGCACTGGGTCCGGCAAG

CTCCAGGGAAGGGCCTGGAATGGGTCTCAGCTATCACTTGGAATAGTGGTCACATAGACTAT

GCGGACTCTGTGGAGGGCCGATTCACCATCTCCAGAGACAACGCCAAGAACTCCCTGTATCT

GCAAATGAACAGTCTGAGAGCTGAGGATACGGCCGTATATTACTGTGCGAAAGTCTCGTACC

TTAGCACCGCGTCCTCCCTTGACTATTGGGGCCAAGGTACCCTGGTCACCGTCTCGAGCGCT

AGTGCATCCGCCCCAACCCTTTTCCCCCTCGTCTCCTGTGAGAATTCCCCGTCGGATACGAG

CAGCGTGGCCGTTGGCTGCCTCGCACAGGACTTCCTTCCCGACTCCATCACTTTCTCCTGGA

AATACAAGAACAACTCTGACATCAGCAGCACCCGGGGCTTCCCATCAGTCCTGAGAGGGGGC

AAGTACGCAGCCACCTCACAGGTGCTGCTGCCTTCCAAGGACGTCATGCAGGGCACAGACGA

ACACGTGGTGTGCAAAGTCCAGCACCCCAACGGCAACAAAGAAAAGAACGTGCCTCTTCCAG

TGATTGCCGAGCTGCCTCCCAAAGTGAGCGTCTTCGTCCCACCCCGCGACGGCTTCTTCGGC

AACCCCCGCAAGTCCAAGCTCATCTGCCAGGCCACGGGTTTCAGTCCCCGGCAGATTCAGGT

GTCCTGGCTGCGCGAGGGGAAGCAGGTGGGGTCTGGCGTCACCACGGACCAGGTGCAGGCTG

AGGCCAAAGAGTCTGGGCCCACGACCTACAAGGTGACCAGCACACTGACCATCAAAGAGAGC

GACTGGCTCAGCCAGAGCATGTTCACCTGCCGCGTGGATCACAGGGGCCTGACCTTCCAGCA

GAATGCGTCCTCCATGTGTGTCCCCGATCAAGACACAGCCATCCGGGTCTTCGCCATCCCCC

CATCCTTTGCCAGCATCTTCCTCACCAAGTCCACCAAGTTGACCTGCCTGGTCACAGACCTG

ACCACCTATGACAGCGTGACCATCTCCTGGACCCGCCAGAATGGCGAAGCTGTGAAAACCCA

CACCAACATCTCCGAGAGCCACCCCAATGCCACTTTCAGCGCCGTGGGTGAGGCCAGCATCT

GCGAGGATGACTGGAATTCCGGGGAGAGGTTCACGTGCACCGTGACCCACACAGACCTGCCC

TCGCCACTGAAGCAGACCATCTCCCGGCCCAAGGGGGTGGCCCTGCACAGGCCCGATGTCTA

```
                        -continued
CTTGCTGCCACCAGCCCGGGAGCAGCTGAACCTGCGGGAGTCGGCCACCATCACGTGCCTGG

TGACGGGCTTCTCTCCCGCGGACGTCTTCGTGCAGTGGATGCAGAGGGGGCAGCCCTTGTCC

CCGGAGAAGTATGTGACCAGCGCCCCAATGCCTGAGCCCCAGGCCCCAGGCCGGTACTTCGC

CCACAGCATCCTGACCGTGTCCGAAGAGGAATGGAACACGGGGGAGACCTACACCTGCGTGG

TGGCCCATGAGGCCCTGCCCAACAGGGTCACCGAGAGGACCGTGGACAAGTCCACCGAGGGG

GAGGTGAGCGCCGACGAGGAGGGCTTTGAGAACCTGTGGGCCACCGCCTCCACCTTCATCGT

CCTCTTCCTCCTGAGCCTCTTCTACAGTACCACCGTCACCTTGTTCAAGGTGAAATGAGCGG

CCGCTTTACGCGTTAAC3'
```

BglII-HpaI restriction enzyme sites at the 5' and 3' ends of the insert, respectively, are also highlighted in boldface print and are underlined, and indicate the transition to the MigR1 vector backbone (Pear et al. 1998).

In order to replace the V-coding region in Seq-ID28 contained in the MigR1 retroviral backbone, with the VH3.30-DH1.26-JH3 "quasi-germline" cassette, the ca. 1.1 kb VH3.30-DH1.26-JH3 fragment needed to be re-amplified by PCR using a BglII containing forward and a XhoI containing reverse primers Seq-ID29 and Seq-ID30, respectively (FIG. 11a).

```
Seq-ID29:  5'-GAAGATCTCACCATGGAGTTTG-3'
                 BglII

Seq-ID30:  5'-ATCTTACCTCTCGAGACGGTGA-3'
                         XhoI
```

The resulting ca. 1.1 kb PCR-fragment was digested with BglII and XhoI and was ligated into BglII-XhoI linarized pH-chain containing MigR1 vector, thereby resulting in the V-D-J recombination competent retroviral expression vector pVDJ-muH-MigR1 (FIG. 11b).

b) Demonstration of Bona Fide V(D)J Recombination Occurring in Retroviral V-D-J Vectors Generating Diverse Sequences Upon Transduction in Precursor B Cells.

As a proof-of-concept, to demonstrate that proper V(D)J recombination can occur in retroviral vectors containing V, D and J gene segments in "quasi-germline" configuration, the vector pVDJ-muH-MigR1 was co-transduced into A-MuLV-transformed preB cell line 230-238 together with a retroviral IgL chain expression vector, as described in Example 1b. Only, if a V(D)J recombination event occurs on the pVDJ-muH-MigR1 construct, that results in the in-frame rearrangement of the V, D and J gene segments, can a full-length human IgM antibody be expressed on the cell surface of the double-transduced cells. Transduction efficiency of the pVDJ-muH-MigR1 vector can be monitored by co-expression of the IRES-coupled EGFP marker gene. As can be seen in FIG. 12(a), a very small population of 0.04% of cells that were transduced with at least the pVDJ-muH-MigR1 construct (efficiency of transduction was 44.7%), displayed detectable IgM expression on the cell surface, as measured by FACS-staining with an anti-kappa light chain antibody. Notably, practically no IgM expressing cells were detectable in the cell population not transduced with the pVDJ-muH-MigR1 construct (lower right quadrant in FIG. 12(a)), demonstrating the specificity of the staining.

The rare IgM expressing cells detectable in the upper right quadrant of FIG. 12(a) have been sorted by preparative cell sorting using a FACS-Aria high speed cell sorter (BD, Franklin Lakes, N.J.) and have been expanded in tissue culture for 8 days, in order to expand the cells for characterization of retroviral integrants. The FACS profile for EGFP expression (indicative of integrated pVDJ-muH-MigR1 construct) and surface IgM after 8 days of expansion showed possibly few clonally expanded cells that displayed IgM on the cell surface and contained the pVDJ-muH-MigR1 construct (as measured by green fluorescence, FIG. 12(b)). Distinct cell populations in the upper right area of the FACS-plot of FIG. 12(b) have been sorted and genomic DNA has been prepared from pooled cell populations.

Genomic DNA was analyzed by a diagnostic PCR using primers binding in the pVDJ-muH-MigR1 construct upstream of the VH and downstream of the JH region. As expected, the diagnostic PCRs resulted in two discrete bands of almost equal intensity, indicative of unrearranged V, D and J gene segments (ca. 1.2 kb fragment) and a smaller, ca. 0.5 kb fragment, indicative of V(D)J recombined gene segments (data not shown). Sequencing of the larger PCR band confirmed that this PCR amplicon represented the unrearranged V-D-J cassette, still in "quasi-germline" configuration. These unrearranged constructs were still detectable in IgM positive cells, if the cells were transduced with more than one construct, of which not all might be accessible for V(D)J recombination. The smaller PCR amplicon did not result in a unique sequence upon sequencing of the PCR product and needed to be subcloned into the pSC-B PCR cloning vector for sequence analysis of individual PCR fragments.

From 6 plasmids analyzed, 2 contained identical bona-fide V(D)J recombination sequences, that showed all characteristic features of site-directed joining of V, D and J gene segments by V(D)J recombination, including nucleotide loss at the coding regions and addition of non-templated sequences (N-regions) that are catalyzed by the precursor lymphocyte specific enzyme terminal deoxynucleotidyl transferase (TdT) (FIG. 12(b)).

Already the two recovered sequences, represented by sequence of clone 225 (FIG. 12b), are firm evidence for the capacity of the V, D, and J gene segment containing retroviral expression vectors to undergo V(D)J recombination in precursor B lymphocytes, as there is no other explanation of how these sequences, showing all signs of a bona fide V(D)J recombination event, could have been generated otherwise, even if the efficiency at this point appeared to be low. It is concluded that upon increase of the efficiency of V(D)J recombination in the context of retroviral transduction of precursor lymphocytes a diverse collection of antibody sequences can be generated from a limited number of retroviral vectors containing V, D and J gene segments in "quasi-germline" configuration.

Example 5

Identification and Characterization of Suitable Selector Murine B Cell Lines for Retrocyte Display a) The expression of endogenous antibodies in B cell lines can potentially hamper their utilization as selector cells in retrocyte display, as pairing of endogenous mouse immunoglobulin chains with recombinant fully antibody chains could negatively affect their cell-surface display, or can lead to the expression of mixed human-mouse immunoglobulins with undefinable binding specificities. Therefore, a panel of Abelson murine leukemia virus (A-MuLV) transformed murine pre-B cell lines described in the literature, were examined for intracellular expression of endogenous IgM heavy chains (μH) using anti-murine IgM heavy chain antibodies coupled to FITC (Southern Biotech). These cells included the lines 40E1, 230-238, 204-1-8 (Alt et al., 1981), 18-81, 18-81 subclone 8-11 (Rosenberg & Baltimore 1978), 63-12 (here called FA-12) cells from RAG-2 deficient mice (Sinkai et al., 1992), and 1624-5, 1624-6 from triple surrogate light chain knockout mice (Shimizu et al., 2002). Cells were permeabilized using the Fix/Perm-kit (Caltech) following the manufacturer's instructions. As depicted in FIG. 14, cell lines FA-12, 40E1, and 18-81 subclone 8-11, 1624-5 and 1624-6, showed the least or no signal for intracellular IgM staining qualifying them as suitable selector cells for Retrocyte Display.

b) As Retrocyte Display is based on retrovirus vector-mediated gene transfer, the panel of murine, A-MuLV transformed pre-B cell lines was further examined for their susceptibility to retroviral transduction using ecotropic MLV-derived vector particles containing a green fluorescent protein (GFP) marker gene 9FIG. 13). $1 \times 10^5$ cells were transduced at an MOI of 0.5 using a vector preparation having packaged the reporter gene GFP encompassing transfer vector LEGFP-N1 (Clontech) previously titrated on 18-81 subclone 8-11 pre-B cells by limiting dilution. Vector particles were generated as described below. Transduction was performed by spin-infection, essentially using centrifugation in 1.5 ml-Eppendorf tubes at 3.300 rpm and 30° C. for 3 hours. Two days post transduction, gene transfer was analyzed by determining the frequency of CFP expressing cells by FACS-analysis. Untreated, naïve target cells served as negative controls. As illustrated in FIG. 13, only original 18-81 cells showed very low permissiveness to MLV vector transduction (<10%). All other cell lines revealed gene transfer efficiencies of 40%. Notably, with FA-12, 40E1 and 1624-5 cells gene transfer efficiencies were maximal and reached >50% in the current experiment.

Taken together, FA12, 40E1 and 1624-5 cells were found to be best suitable for Retrocyte Display considering both criteria, a) low or absent endogenous murine immunoglobulin expression and b) susceptibility for retroviral transduction. However, as it is desired to express immunoglobulins composed of recombinant heavy and light chains, B cells are preferred that lack expression of surrogate light chain components as well (expressible from λ5, or VpreB1, or VpreB2 genes) as those may also compete for heavy chain association with recombinant light chains in wild-type preB cells. Thus, 1624-5 cells derived from surrogate light chain triple knockout mice are expected to be the best-suited cells for further retrocyte display technology. However, it shall be understood, that any other cell line, including the additional cell lines analyzed here, which satisfy the criteria for no/low endogenous immunoglobulin expression and retroviral transducibility, may be used to realize the method disclosed herein.

Example 6

Generation of Selector Cells Clonally and Stably Expressing Fully Human Antibody Libraries To generate vector particles having packaged transfer vectors encoding fully human antibody chains and libraries thereof and their subsequent employment for the transduction of murine B cell lines, infection experiments were performed by the following method. Human embryonic kidney 293T-HEK cells were plated at $2 \times 10^6$ in 10 ml of Dulbeccos Modified Eagle Medium (DMEM), supplemented with 10% fetal calf serum (FCS) and L-Glutamin per 10 cm tissue culture dish, 16 to 24 hours prior to transfection. Mixtures of 5 µg of the respective transfer vectors IgL(245)-LIB-IRES-YFP and IgH(650)-LIB-IRES-GFP (encoding libraries of heavy or light chains linked by an IRES to GFP or YFP expression, FIG. 15), 3 µg of pVPack-GP (an expression construct harboring gag and pol genes of MLV) and 2.5 µg of pVPack-Eco (an expression construct encompassing the env gene of ecotropic MLV, both STRATAGENE) were prepared and incubated with 30 µl of Fugene (Roche) in 1 ml serum-free DMEM, and were left standing for 15 to 30 minutes at room temperature. The Fugene/DNA mix was then gently added to the 293T-HEK cells seeded in the 10 cm dishes. Heavy and light chain-encoding transfer vectors were transfected into separate transient packaging cells.

48 hours post transfection, vector particle-containing supernatants were collected from transient packaging cells and centrifuged at 3,000 rpm to remove contaminating cells. $1.5 \times 10^6$ 1624-5 murine B cells were suspended in 1 ml of media supplemented with different quantities of vector particles (diluted 1:1; 1:5; 1:20; 1:50; 1:100; 1:200) having packaged the heavy or light chain-encoding regions of antibodies. Transduction was performed by centrifugation in 1.5 ml-Eppendorf cups at 3.300 rpm and 30° C. for 3 hours. Unused supernatants were stored at −80° C. for utilization at a later time-point. To ensure that single copies of transfer vectors integrated into the host cell genome, cells revealing four days post infection gene transfer efficiency lower than 10% (detected by expression of GFP or YFP) were enriched using FACS (FIG. 16). The cells were expanded for six days and subjected to a second transduction procedure employing previously frozen vector particles having packaged the light chain coding regions of antibodies at a dilution of 1:5 as described above. Here, GFP-positive cells selected for heavy chain expression were infected with vector particles transducing the light chain-IRES-YFP library and vice versa (FIGS. 15 & 16). Four days post infection, successfully transduced cells expressing GFP and YFP were enriched using FACS. Approximately 20% of the cells showed GFP and YFP expression after the second transduction. To secure that only single vector integrations occurred per cell about one third of the populations were enriched that revealed only low or moderate expression of the reporter gene transduced in the second round (approx. 8%, see FIG. 16).

Example 7

Detection and Enrichment of Antigen-Reactive Human Antibody Expressing Cells by Retrocyte Display a) As a preparation for a Retrocyte Display proof of concept experiment, firstly the optimal staining and detection conditions for IL-15 binding antibodies retrovirally expressed on selector cells was determined. 1624-5 A-MuLV transformed preB cells co-expressing a human IgH and IgL chain library were mixed at a ratio of 2:1 with 1624-5 A-MuLV transformed preB cells expressing retroviral expression vectors encoding a human anti-IL-15 antibody on the cell surface. Mixed cell samples were incubated with various concentrations of recombinant human IL-15 (0.1 to 2.5 µg/ml), and various concentrations of a polyclonal, biotinylated anti-hu-IL-15 antibody (1.0 and 3.0 µg/ml), as indicated, which was eventually revealed with streptavidin-phycoerythrin (strep-PE). To discriminate cells displaying antibodies from non-immunoglobulin expressing cells, samples were additionally counter-stained with an anti-hu-IgκL-APC antibody. As can be seen in the two upper-right FACS panels of FIG. 17, IL-15 reactive cells were most efficiently detected (20.1 and 20.4%) using a combination of 0.1 and 0.5 µg/ml of recombinant IL-15 as a primary reagent, and 3.0 µg/ml of the biotinylated anti-hu-IL-15 antibody as a secondary staining reagent.

b) Next, a proof-of-concept experiment was performed, in which a reference antibody specific for human IL-15 was spiked into a pool of cells expressing a diverse library of human antibodies, upon which the spiked-in antigen-reactive cells have been analyzed by FACS. In preparation of this experiment, a library of antibodies retrovirally expressed in 1624-5 cells (see Example 6), was stained for surface Ig expression and for IL-15 binding (NC), alongside with a 1624-5 cell line expressing reference antibody specific for the human IL-15 antigen (PC). FACS analyses on these NC and PC cell lines are shown in FIG. 18, and demonstrate the specific IL-15 staining of the anti-IL-15 reference antibody displayed on the surface of the PC cells. In order to analyze, whether the reference anti-IL-15 Ab expressing cell line is still quantitatively detectable by FACS, if the PC cells are spiked into the NC cell line expressing a random collection of human antibodies, different dilutions of PC cells in the NC library were analyzed by FACS for specific IL-15 binding using the optimized IL-15 staining conditions determined above. FACS-analysis of negative control cells revealed only a small population exhibiting IL-15-binding activity. In contrast, more than 60% of the positive control population was demonstrated to bind IL-15. Upon mixing both above populations at ratios of 10, 12.5, 25, 37.5, and 50%, a correlation between the percentages of positive control cells mixed into the antibody library cell pool with the fraction of cells shown to bind IL-15 was observed. Thus, it is concluded that IL-15 reactive cells can quantitatively be detected by FACS staining in mixtures with other non-specific antibody expressing cells.

c) Next a proof of concept experiment was performed, in which rare IL-15 reactive cells were enriched by Retrocyte Display. For this, a highly diverse collection of human antibodies expressed in 1624-5 preB cells was generated by retroviral transduction of an IL-15 IgH chain (coupled to GFP), and co-transduction of a complex collection (complexity approximately $7\times10^4$) of human IgκL chains (coupled to YFP). Thus, a Retrocyte Display antibody library was created by shuffling of a diverse collection of human IgκL chains against a single IgH chain from a human anti-IL-15 specific antibody. Cells were stained for IL-15 reactivity using optimized conditions as determined before. IL-15 reactive cells were enriched by three consecutive rounds of high-speed FACS cell sorting, followed by cell culture expansion. After three rounds of Retrocyte Display enrichment, a cell population could be obtained expressing human antibodies and that essentially stained quantitatively for the antigen IL-15 from an initial cell population in which IL-15 reactive cells were hardly detectable (FIG. 19). This experiment demonstrated that repeated rounds of Retrocyte Display enrichment could efficiently be used to enrich IL-15 binding cells.

d) Confirmation of IL-15 binding specificity of individual cell clones established from a 3×IL-15 enriched cell pool (see previous example). Next, from the cell pool which was 3 times subjected to IL-15-specific Retrocyte Display enrichment, 25 individual cell clones have been established by single cell sorting. These 25 cell clones have been characterized for their IL-15 specificity by IL-15 staining, using the previously optimized staining conditions (see Example 7a). As a control for the specificity of the IL-15 staining, all clones were also incubated with all staining reagents, except for the IL-15 antigen. The majority of the single cell clones displayed a highly specific IL-15 staining pattern that was lost when the IL-15 antigen was left out of the staining reaction. Representative IL-15 specific stainings are shown in FIG. 19 with 4 selected individual cell clones. Stainings for these clones are representative of altogether 25 cell clones (termed in alphabetical order A to Y) established from a 3×IL-15 antigen enriched cell population, which all tested positive for IL-15 antigen binding. Negative and positive controls for the specificity of the stainings are provided in FIG. 19, as indicated.

Example 8

Chain Shuffling or Guided Evolution Approach: Detection and Iterative Enrichment of Antigen Specific Human Antibody Expressing Cells by High-Speed Cell Sorting, Cloning of the Variable Region Coding Regions from Antigen Selected Cells and Confirmation of Antigen-Specificity As described above (Example 6), a cell library was generated expressing a library of human IgκL chains with a complexity of approximately $1.2\times10^5$ in combination with the heavy chain of reference antibody SK48-E26 (Young et al., WO 95/07997 A1) directed against the target antigen human IL-1β. The retroviral vector backbone harbouring these chains is depicted in more detail in FIGS. 4c and 11 (see also Example 4). For this, $3\times10^6$ 1624-5 A-MuLV transformed 1624-5 preB cells were transduced with the SK48-E26 IgH chain-encoding transfer vector harbouring particles at a MOI less than 0.1. One day after transduction CFP-positive cells were enriched by standard high speed cell sorting using a FACSAria from BD. Sorted cells were expanded in tissue culture in a humidified incubator for five days. Following expansion, the cell population was transduced with particles having packaged the IgκL chain library at a MOI of 1.5 by standard spin infection as described above (Example 5), and cells were allowed to recover from transduction for two days in tissue culture. Following the two days recovery and expansion period, $5\times10^5$ cells co-expressing GFP and YFP, and thus harbouring at least one heavy and one light chain construct, were enriched using preparative cell sorting using a FACSAria from BD. The cell population now enriched for co-expression of IgH and IgL chain constructs was expanded for another four days in tissue culture. After this final expansion, an aliquot of $2\times10^6$ cells expressing the IgH/IgL-chain library were stained with 2 µg/ml in a volume of 100 µl with recombinant human IL-1β (R&D Systems) for 30 minutes on ice followed by two washing steps using phosphate buffered saline (PBS) supplemented with 1% fetal calf serum (FCS). After incubation with polyclonal antibodies directed against IL-1β and conjugated to biotin, cells were washed again twice and subsequently stained with streptavidin-APC for detection of antigen-binding cells and their subsequent enrichment using flow cytometry. After a first round of cell sorting by FACS, cells were expanded for five days and subjected to another round of anti-IL-1β staining and enrichment of positively staining cells as described above. This selection was repeated three times (FIG. 21). The cell population obtained after three rounds of Retrocyte Display enrichment, was again stained for IL-1β binding as described above, but this time reactive cells were not enriched as bulk populations as previously, but individual cell clones were sorted into 96 well plates by means of single cell sorting using a FACSAria from BD. Following seven days of cultivation and expansion, individual cell clones were again analysed for IL-1β antigen-specificity using the described protocol and, in addition, as a negative control, with all secondary reagents, except the antigen IL-1β. As expected and demonstrated using flow cytometry, some clones showed specific binding to the target antigen as revealed by a specific FACS signal in the presence of the antigen, but not in the absence of it (excluding background binding of the clones to any of the secondary detection reagents). However, some clones showed a staining signal irrespective of the presence of the antigen indicating that these clones non-specifically bound to any of the secondary reagents used for the detection of IL-1β reactivity. In total, genomic DNA of 24 cell clones was isolated and served as a template for standard genomic PCR employing oligonucleotides Seq-ID31 and Seq-ID32, specifically binding up- and down-stream of the variable region of human light chains encoded in the retroviral light chain library, respectively.

```
Seq-ID31:  5'-CCTTGAACCTCCTCGTTCGACCC-3'

Seq-ID32:  5'-AGGCACAACAGAGGCAGTTCCAG-3'
```

PCR amplicons of expected size were obtained from each analyzed cell clone, and the PCR amplicons were directly subjected to DNA sequence analysis. Of the 24 clones analysed twelve were shown to harbour an identical, but novel IgκL chain, termed LCB24, and, as expected also harboured the IgH chain of SK48-E26, as determined separately.

As expected, all 12 clones expressing the LCB24 IgL chain in combination with the SK48-E26 IgH chain displayed specific IL-1β-signals using flow cytometry as mentioned above.

A selected PCR amplicon containing the amplified novel LCB24 IgκL chain was digested with the restriction enzymes HindIII and Eco47III flanking the variable coding region (FIG. 4c), and the fragment was cloned into a retroviral IgκL chain expression vector with compatible restriction enzyme sites allowing the in-frame fusion of the LCB24 $V_L$ coding region to the constant human kappa light chain coding region. Thus, the resultant vector encoded a novel, fully human IgκL chain.

The re-cloned, and sequence verified retroviral expression vector for the LCB24 Ig L chain was transduced together with the SK48E26 IgH chain of the IL-1β reference antibody SK48-E26 into 1624-5 cells. After expansion in tissue culture for 2 days, GFP+/YFP+ cells were enriched by high-speed cell sorting using a FACSAria from BD. The resulting, Ig expressing cells were first tested for their ability to bind IL-1β as described. As expected their reactivity mediated by display of LCB24 together with the heavy chain of SK48-E26 was confirmed (FIG. 22). To exclude that the novel antibody was generally cross-reactive to other antigens or proteins, the cells expressing the LCB24 IgL/SK48-E26 IgH combination were assayed for IL-15 reactivity, as described before. As depicted in FIG. 23, no reactivity for IL-15 could be detected for the novel IgL LCB24/HC SK48-E26 antibody, indicating the target antigen-specificity of the novel antibody. Further controls included a cell line expressing an anti-IL-15 specific reference antibody (as positive control) and the original SK48-E26 IL-1β antibody. While the anti-IL-15 antibody expressing cells, as expected, showed specific staining to IL-15, no reactivity was detected for the SK48-E26 IL-1β antibody or for cells (FIG. 23).

In summary, a novel light chain mediating antigen-specific reactivity was identified in a screening experiment employing a library of light chains shuffled against the heavy chain of an IL-1β specific reference antibody SK48-E26.

Example 9

Retrocyte Display Screening on Shuffled IgH and IgL Chain Libraries. Detection and Iterative Enrichment of Antigen Specific Human Antibody Expressing Cells by High-Speed Cell Sorting, Cloning of the Variable Region Coding Regions from Antigen Selected Cells and Confirmation of Antigen-Specificity As described above (Example 6), a cell library was generated expressing a library of heavy chains with a complexity of approximately $6.5 \times 10^5$ (coupled to GFP) using a MOI of approximately 0.1. The retroviral vector backbone harbouring these chains is depicted in FIGS. 4c and 11 in more detail (see also Example 4). For this, $3 \times 10^6$ 1624-5 A-MuLV transformed 1624-5 preB cells were transduced with the above-mentioned IgH chain-library encoding transfer vector harbouring particles at a MOI less than 0.1. Two days after transduction, GFP-positive cells were enriched by standard high speed cell sorting using a FACSAria from BD. After sorting of GFP+ cells, the cells were expanded in tissue culture for two additional days. After expansion, the GFP+ cell population was transduced with particles having packaged a light chain library consisting of 245 fully sequence characterized light chains at a MOI >1 as described before. Two days post transduction, GFP+/YFP+ double transduced cells were enriched by high speed cell sorting and the cell population, now harbouring both IgH and IgL chain libraries in the majority of the cells were again expanded for three days in tissue culture. After this, an aliquot of $2.5 \times 10^5$ cells was stained with a cocktail of antigens including inter alia SAV (streptavidin)-APC-Cy7 as described above (see Example 8), and enriched for reactivity of the target antigen using flow cytometry. In parallel, the cell population expressing the antibody IgH/IgL library was stained using anti-IgL kappa specific antibodies. Approximately 75% of these cells were found to display human antibodies on the cell surface (data not shown). Antigen-reactive cells have been sorted by high-speed cell sorting using a FACSAria from BD, and enriched cells were expanded in tissue culture for seven days. The same staining and cell enrichment procedures, as described above were repeated twice more. After three Retrocyte Display selection rounds the resultant cell population was again stained to assess binding of the target antigen SAV-APC-Cy7 and analysed using flow cytometry. As depicted in FIG. 24, the bulk population obtained showed binding to SAV-APC-Cy7 indicating the successful selection of antibodies with antigen-specificity to SAV-APC-Cy7. To assess the specificity of reactivity against the target antigen SAV-APC-Cy7 the three-times enriched library expressing cells were also stained with the antigens SAV-APC and SAV-PerCP-Cy5.5 (FIG. 25). Similar to un-transduced cells and unselected library expressing cells serving as negative controls, these antigens were not bound by the three-times SAV-APC-Cy7 enriched cells. However, the later cells did again reveal strong reactivity to SAV-APC-Cy7, indicating that the antigen-specificity of the selected cell population was directed against the Cy7 fluorochrome of the SAV-APC-Cy7 tandem dye.

Genomic DNA of the 3-times enriched cell population was isolated and served as a template for standard genomic PCR employing oligonucleotides Seq-ID31 (see above) and Seq-ID33 specifically binding up- and down-stream of the coding regions of human light and heavy chains encoded in the retroviral libraries.

```
Seq-ID33: 5'-CGGTTCGGGGAAGTAGTCCTTGAC-3')
```

PCR amplicons for the heavy chains and light chains of expected size were obtained and were separately subcloned into a standard PCR-fragment cloning vector pSC-B (Stratagene), as recommended by the manufacturer. pSC-B plasmid clones harbouring the cloned heavy and light chain regions were isolated from 10 bacterial clones each resulting from the IgH PCR fragment subcloning and the IgL PCR fragment subcloning, which were all subjected to DNA sequence analysis. DNA sequencing revealed two different IgH chain sequences termed HC49, HC58 and two different IgL chain sequences termed LC4 and LC10.

DNA fragments containing the $V_H$ and $V_L$ coding regions were isolated from sequence verified clones by HindIII and Eco47III digestion, as these restriction enzyme sites flank the variable regions (see FIG. 4c) of the respective $V_H$ and $V_L$ regions of HC49, HC58, LC4 and LC10. The isolated $V_H$ and $V_L$ regions of HC49, HC58, LC4 and LC10 were cloned into a retroviral recipient vector harbouring the constant regions of a human Igγ1H chain (expression IRES coupled to GFP) and a human IgκL chain (expression IRES coupled to YFP), respectively, as described above. Thus, retroviral expression vector constructs were generated encoding fully human IgH and IgL chains for the novel HC49 and HC58 IgH chains, LC4 and LC10 IgL chains. Upon co-transduction of these vectors into 1624-5 preB cells and expansion for 8 days, GFP+/YFP+ cells were enriched using flow cytometry as before. Resultant cells were first tested for their ability to bind SAV-APC-Cy7 as described. As depicted in FIG. 26, reactivity of cells expressing the antibodies HC49/LC4 and HC/LC10 did not show significant binding activity against SAV-APC-Cy7. In contrast, reactivity mediated by antibodies HC58/LC4 and HC58/LC10 was readily detected. This provides a proof of concept for the successful identification of novel antigen-specific antibodies by Retrocyte Display based on the shuffling of diverse collections of IgH chains and IgL chains, without the need of either a known IgH or IgL chain from a reference antibody with known antigen-specificity.

REFERENCES

Alt F, Rosenberg N, Lewis S, Thomas E, Baltimore D (1981) "Organization and reorganization of immunoglobulin genes in A-MULV-transformed cells: rearrangement of heavy but not light chain genes" Cell 27, 381-390.

Bachl J and Olsson C (1999) "Hypermutation targets a green fluorescent protein-encoding transgene in the presence of immunoglobulin enhancers" Eur J. Immunol. 29, 1383-1389.

Baker M (2005) "Upping the ante on antibodies" Nature Biotechnology 23, 1065-1072.

Boder E T, Midelfort K S, Wittrup K D (2000) "Directed evolution of antibody fragments with monovalent femtomolar anigen-binding affinity" Proc. Natl. Acad. Sci. USA 97, 10701-5.

Clackson T, Hoogenboom H, Griffiths A D, Winter G (1991) "Making antibody fragments using phage display libraries" Nature 352, 624-628.

Clark M (2000) "Antibody humanization: A case of the 'Emperor's new clothes'?" Immunol. Today 21, 397-402.

Dunn I S (1995) "Assembly of functional bacteriophage lambda virions incorporating C-terminal peptide or protein fusions with the major tail protein" J. Mol. Biol. 248, 497-506.

Efimov V P, Nepluev I V, Mesyanzhinov V V (1995) "Bacteriophage T4 as a surface display vector" Virus Genes 10, 173-7.

Gossen M and Bujard H (1992) "Tight control of gene expression in vertebrate cells by tetracycline-responsive promoters" Proc. Natl. Acad. Sci. USA 89, 5547-5551.

Grawunder U, West R B, Lieber M R (1998) "Antigen receptor gene rearrangement" Curr. Opin. Immunol. 10: 172-180.

Green L L and Jakobovits A (1998) "Regulation of B cell development by variable gene complexity in mice reconstituted with human immunoglobulin yeast artificial chromosomes" J. Exp. Med. 188, 483-495.

Hanes J and Pluckthun A (1997) "In vitro selection and evolution of functional proteins by using ribosome display" Proc. Natl. Acad. Sci. USA 94, 4937-4942.

Hanes J, Schaffitzel C, Knappik A & Pluckthun A (2000) "Picomolar affinity antibodies from a fully synthetic naïve library selected and evolved by ribosome display" Nature Biotech. 18, 1287-1292.

Hoogenboom H R and Chames P (2000) "Natural and designer binding sites made by phage display technology" Immunol. Today 21, 371-378.

Kitamura T, Onishi T, Kinoshita S, Shibuya A, Miyajima A, Nolan GP (1995) "Efficient screening of retroviral cDNA expression libraries" Proc. Natl. Acad. Sci. USA. 92, 9146-9150.

Köhler G and Milstein C (1975) "Continuous cultures of fused cells secreting antibody of predefined specificity" Nature 256, 495-497.

Li Y S, Hayakawa K, Hardy R R (1993) "The regulated expression of B lineage associated genes during B cell differentiation in bone marrow and fetal liver" J. Exp. Med. 178, 951-960.

Li M (2000) "Applications of display technology in protein analysis" Nature Biotechnology 18, 1251-6.

Lipovsek D & Pluckthun A (2004) "In-vitro protein evolution by ribosome display and mRNA display" J. Immunol. Methods 290, 51-67.

Maruyama I N, Maruyama H I, Brenner S (1994) "Lambda foo: a lambda phage vector for the expression of foreign proteins" Proc. Natl. Acad. Sci. USA 91, 8273-7.

Papavasiliou F N and Schatz D G (2002) "Somatic hypermutation of immunoglobulin genes: merging mechanisms for genetic diversity" Cell 109, Suppl: S35-S44.

Pear W S, Miller J P, Xu L, Pui J C, Soffer B, Quackenbush R C, Pendergast A M, Bronson R, Aster J C, Scott M L, Baltimore D (1998) "Efficient and rapid induction of a chronic myelogenous leukemia-like myeloproliferative disease in mice receiving P210 bcr/abl-transduced bone marrow" Blood 92, 3780-92.

Ren Z J, Lewis G K, Wingfield P T, Locke E G, Steven A C, Black L W (1996) "Phage display of intact domains at high copy number: a system based on SOC, the small outer capsid protein of bacteriophage T4" Protein Sci. 5, 1833-43.

Rosenberg N and Baltimore D (1978) "The effect of helper virus on Abelson virus-induced transformation of lymphoid cells" J. Exp. Med. 147, 1126-1141.

Rosenberg A (1996) "T select phage display system: a powerful new protein display system based on the bacteriophage T7" Innovations 6, 1-6.

Santini C, Brennan D, Mennuni C, Hoess R H, Nicosia A, Cortese R, Luzzago A (1998) "Efficient display of an HCV cDNA expression library as C-terminal fusion to the capsid protein D of bacteriophage lambda" J. Mol. Biol. 282, 125-35.

Shimizu T, Mundt C, Licence S, Melchers F, Martensson I L (2002) "VpreB1/VpreB2/lambda 5 triple-deficient mice show impaired B cell development but functional allelic exclusion of the IgH locus" J. Immunol. 168, 6286-6293.

Shinkai Y, Rathbun G, Lam K P, Oltz E M, Stewart V, Mendelsohn M, Charron J, Datta M, Young F, Stall A M, et al. (1992) "RAG-2-deficient mice lack mature lymphocytes owing to inability to initiate V(D)J rearrangement" Cell 68, 855-867.

Smith G P (1985) "Filamentous fusion phage: novel expression vectors that display cloned antigens on the viron surface" Science 228, 1315-17.

Sternberg N & Hoess R H (1995) "Display of peptides and proteins on the surface of bacteriophage lambda" Proc. Natl. Acad. Sci. USA 92(5), 1609-13.

Stitz J, Krutzik P O, Nolan G P (2005) "Screening of retroviral cDNA libraries for factors involved in protein phosphorylation in signaling cascades" Nucleic Acids Res. 33, e39.

Traggiai E, Chicha L, Mazzucchelli L, Bronz L, Piffaretti J C, Lanzavecchia A, Manz M G (2004) "Development of a human adaptive immune system in cord blood cell-transplanted mice" Science 304, 104-107.

EP 1 041 143 A: Jensen M R, Pedersen F S, Mouritzen S, Hindersson P, Duch M, Soerensen M S, Dalum I, Lund A H "A method for identification of biologically active peptides and nucleic acids".

WO 89/12823 A1: Mosier D E and Wilson D B "Human immune system in non-human animal".

WO 90/13660 A2: Lang A B, Larrick J W, Cryz S J "Human monoclonal antibodies to sero-specific determinants of gram-negative bacteria".

WO 92/01047 A1: McCafferty J, Pope A R, Johnson K S, Hoogenboom H R J M, Griffiths A D, Jackson R H, Holliger, K P, Marks J D, Clackson T P, Chiswell D J, Winter G P, Bonnert T P "Methods for producing members of specific binding pairs".

WO 92/02551 A1: Schrader J W "Methods for the production of proteins with a desired function".

WO 95/01997 A1: Young P R, Gross M S, Jonak Z L, Theisen T W, Hurle M R, Jackson J R "Recombinant and humanized IL-1beta antibodies for treatment of IL-1 mediated inflammatory disorders in man".

WO 98/24893 A2: Jakobovits A, Kucherlapati R, Klapholz S, Mendez M, Green L "Transgenic mammals having human Ig loci including plural $V_H$ and $V_k$ regions and antibodies produced therefrom".

WO 02/066630 A1: Murphy A J and Yancopoulos G D "Methods of modifying eukaryotic cells".

WO 02/102855 A2: Zauderer M and Smith E S "In vitro methods for producing and identifying immunoglobulin molecules in eukaryotic cells".

WO 03/017935 A2: van der Winkel J G J, van Dijk M A, Schuurman J, Gerritsen A F, Baadsgaard O "Human antibodies specific for interleukin 15 (IL-15)".

WO 03/054197 A2: Perabo L, Boning H, Enssle J, Reid M, Hallek M "A library of modified structural genes or capsid modified particles useful for the identification of viral clones with desired cell tropism".

WO 03/068819 A1: Grawunder U and Melchers G F "Method for the generation of genetically modified vertebrate precursor lymphocytes and use thereof for the production of heterologous binding proteins".

WO 03/083075 A2: Bremel R D, Bleck G T, Imboden M, Eakle K "Retrovirus-based genomic screening".

WO 04/051266 A1: Muraguchi A, Kishi H, Tamiya E, Suzuki M "Microwell array chip for detecting antigen-specific lymphocyte, method of detecting antigen-specific lymphocyte and method of cloning antigen-specific lymphocyte antigen receptor gene".

WO 04/076677 A2: Lanzavecchia A "Monoclonal antibody production by EBV transformation of B cells".

WO 04/106377 A1: Lawson A D G and Lightwood D J "Methods for producing antibodies".

WO 08/055,795 A1: Beerli R, Bachmann M, Bauer M "Selection of human monoclonal antibodies by mammalian cell display".

The invention claimed is:

1. A plurality of stably transduced vertebrate host cells, wherein each member of the plurality of stably transduced vertebrate host cells (i) comprises a stably integrated retroviral expression vector encoding a full-length antibody heavy chain polypeptide, a stably integrated retroviral expression vector encoding a full-length antibody light chain polypeptide, and a screening marker, and (ii) expresses on the cell surface a full-length antibody that is encoded by the stably integrated retroviral expression vectors, wherein each member of the plurality of stably transduced vertebrate host cells comprises a different full-length antibody heavy chain polypeptide or a different full-length antibody light chain polypeptide, and wherein the plurality of stably transduced vertebrate host cells is generated by:

(a) transducing a first library of replication incompetent retroviral expression constructs encoding a plurality of full-length antibody heavy chain or light chain polypeptides into a population of vertebrate host cells such that a first library of stably transduced vertebrate host cells is generated, wherein the first library of replication incompetent retroviral expression constructs comprise a murine stem cell virus (MSCV) long terminal repeat (LTR), wherein the retroviral transduction is performed at a multiplicity of infection of equal to or less than 0.1, wherein each member of the first library of stably transduced cells comprises at least one retroviral expression construct from the first library of retroviral expression constructs stably integrated into the host cell genome and wherein the vertebrate host cells are Abelson-murine leukemia virus transformed precursor B lymphocytes that do not express lamda-5, VpreB1, and VpreB2 surrogate light chain genes;

(b) transducing the first library of stably transduced cells of step (a) with a second library of replication incompetent retroviral expression constructs encoding a plurality of full-length antibody heavy chain or light chain polypeptides such that a second library of stably transduced vertebrate host cells is generated, wherein the first library of retroviral expression constructs encodes a plurality of full-length antibody heavy chain polypeptides and the second library of retroviral expression constructs encodes a plurality of full-length antibody light chain polypeptides, or the first library of retroviral expression constructs encodes a plurality of full-length antibody light chain polypeptides and the second library of retroviral expression constructs encodes a plurality of full-length antibody heavy chain polypeptides such that the first and the second library of retroviral expression constructs encode antibody heavy and light chain combinations, wherein the first or the second library of retroviral expression constructs further comprise at least one screening marker which is a fluorescent protein or cell surface marker, wherein the second library of replication incompetent retroviral expression constructs comprise a murine stem cell virus (MSCV) long terminal repeat (LTR), wherein the retroviral transduction is performed at a multiplicity of infection of equal to or less than 0.1, and wherein each member of the second library of stably transduced cells comprises at least one retroviral expression construct from the first library of retroviral expression constructs stably integrated into the host cell genome and at least one retroviral expression construct from the second library of retroviral expression constructs stably integrated into the host cell genome; and (c) allowing expression of the first and second stably integrated retroviral expression constructs in the second library of stably transduced vertebrate host cells such that full-length antibodies are expressed on the surface of the second library of stably transduced vertebrate host cells, thereby producing the plurality of stably transduced vertebrate host cells.

2. The plurality of stably transduced vertebrate host cells of claim 1, wherein the full-length antibody is selected from the group consisting of a fully human antibody, a humanized antibody, and a chimeric antibody.

3. The plurality of stably transduced vertebrate host cells of claim 1, wherein the population of vertebrate host cells are derived from a cartilaginous fish, bony fish, amphibian, reptile, bird, or mammal.

4. The plurality of stably transduced vertebrate host cells of claim 3, wherein the mammal is a mouse, rat, rabbit, guinea pig.

5. The plurality of stably transduced vertebrate host cells of claim 4, wherein the mammal is a mouse.

6. The plurality of stably transduced vertebrate host cells of claim 1, wherein the second library of vertebrate host cells ectopically express Igα and Igβ molecules.

7. The plurality of stably transduced vertebrate host cells of claim 1, which has a complexity of at least $6 \times 10^5$.

8. The plurality of stably transduced vertebrate host cells of claim 1, wherein the fluorescent protein is selected from the group consisting of green fluorescent protein (GFP), yellow fluorescent protein (YFP), red fluorescent protein (RFP) and blue fluorescent protein (BFP).

9. The plurality of stably transduced vertebrate host cells of claim 1, wherein the cell surface marker is selected from the group consisting of CD7, CD34 and the low affinity nerve growth factor receptor.

10. The plurality of stably transduced vertebrate host cells of claim 1, 8 or 9, wherein the first and second library of retroviral expression constructs comprise different screening markers.

11. The plurality of stably transduced vertebrate host cells of claim 1, 8 or 9, wherein the at least one screening marker is operably linked to the nucleotide sequence encoding the full-length antibody heavy chain polypeptide or the full-length antibody light chain polypeptide using at least one internal ribosomal entry sequence (IRES).

12. The plurality of stably transduced vertebrate host cells of claim 1, wherein the first or second library of retroviral expression constructs further comprise at least one antibiotic selection marker.

13. The plurality of plurality transduced vertebrate host cells of claim 12, wherein the first and second library of retroviral expression constructs comprise different antibiotic selection markers.

14. The plurality of plurality transduced vertebrate host cells of claim 12 or 13, wherein the at least one antibiotic selection marker is operably linked to the nucleotide sequence encoding the full-length antibody heavy chain polypeptide or the full-length antibody light chain polypeptide using at least one internal ribosomal entry sequence (IRES).

* * * * *

SEQUENCE LISTING

```
<160> NUMBER OF SEQ ID NOS: 47

<210> SEQ ID NO 1
<211> LENGTH: 42
<212> TYPE: DNA
<213> ORGANISM: Artificial Sequence
<220> FEATURE:
<223> OTHER INFORMATION: Primer

<400> SEQUENCE: 1
gatcaagctt agcgcttcca ccaagggccc atcggtcttc cc                    42

<210> SEQ ID NO 2
<211> LENGTH: 43
<212> TYPE: DNA
<213> ORGANISM: Artificial Sequence
<220> FEATURE:
<223> OTHER INFORMATION: Primer
```

```
<400> SEQUENCE: 2
gatcatcgat gcggccgctc atttacccgg agacagggag agg                43

<210> SEQ ID NO 3
<211> LENGTH: 42
<212> TYPE: DNA
<213> ORGANISM: Artificial Sequence
<220> FEATURE:
<223> OTHER INFORMATION: Primer

<400> SEQUENCE: 3
gatcatcgat gcggccgcta ggcccctgc ctgatcatgt tc                  42

<210> SEQ ID NO 4
<211> LENGTH: 443
<212> TYPE: DNA
<213> ORGANISM: Homo sapiens
<220> FEATURE:
<223> OTHER INFORMATION: VH coding region for NIP-Ovalbumin specific
      human antibody

<400> SEQUENCE: 4
aagcttccat ggagtttggg ctcagctggg ttttccttgt tgctcttttta agaggtgtcc    60 agtgtcaggt gcagctggtg gagtctgggg gaggcgtggt ccagcctggg aggtccctga   120
gactctcctg tgcagcctct ggattcacct tcagtagcta tgctatgcac tgggtccgcc   180
aggctccagg caaggggctg gagtgggtgg cagttatatc atatgatgga agcaataaat   240
actacgcaga ctccgtgaag ggccgattca ccatctccag agacaattcc aagaacacgc   300
tgtatctgca aatgaacagc ctgagagctg aggacacggc tgtgtattac tgtgcgagaa   360
tggtcgacca cgcggaaagc tactactact actacggtat ggacgtctgg ggccaaggga   420
caatggtcac cgtctctagc gct                                          443

<210> SEQ ID NO 5
<211> LENGTH: 38
<212> TYPE: DNA
<213> ORGANISM: Artificial Sequence
<220> FEATURE:
<223> OTHER INFORMATION: Primer

<400> SEQUENCE: 5
gatcggatcc gtacactttt ctcatctttt tttatgtg                      38

<210> SEQ ID NO 6
<211> LENGTH: 35
<212> TYPE: DNA
<213> ORGANISM: Artificial Sequence
<220> FEATURE:
<223> OTHER INFORMATION: Primer

<400> SEQUENCE: 6
gatcggatcc ctgaggaagg aagcacagag gatgg                         35

<210> SEQ ID NO 7
<211> LENGTH: 766
<212> TYPE: DNA
<213> ORGANISM: Mus musculus
<220> FEATURE:
<223> OTHER INFORMATION: Genomic PCR fragment

<400> SEQUENCE: 7
gaaaaatgtt taactcagct actataatcc cataattttg aaaactattt attagctttt    60
gtgtttgacc cttccctagc caaaggcaac tatttaagga cccttttaaaa ctcttgaaac  120
```

-continued

```
tactttagag tcattaagtt atttaaccac ttttaattac tttaaaatga tgtcaattcc    180
cttttaacta ttaatttatt ttaagggggg aaaggctgct cataattcta ttgtttttct    240
tggtaaagaa ctctcagttt tcgtttttac tacctctgtc acccaagagt tggcatctca    300
acagagggga ctttccgaga ggccatctgg cagttgctta agatcagaag tgaagtctgc    360
cagttcctcc aaggcaggtg gcccagatta cagttgacct gttctggtgt ggctaaaaat    420
tgtcccatgt ggttacaaac cattagacca gggtctgatg aattgctcag aatatttctg    480
gacacccaaa tacagaccct ggcttaaggc cctgtccata cagtaggttt agcttggcta    540
caccaaagga agccatacag aggctaatat cagagtattc ttggaagaga caggagaaaa    600
tgaaagccag tttctgctct taccttatgt gcttgtgttc agactcccaa acatcaggag    660
tgtcagataa actggtctga atctctgtct gaagcatgga actgaaaaga atgtagtttc    720
agggaagaaa ggcaatagaa ggaagcctga gaatatcttc aaaggg                   766
```

<210> SEQ ID NO 8
<211> LENGTH: 32
<212> TYPE: DNA
<213> ORGANISM: Artificial Sequence
<220> FEATURE:
<223> OTHER INFORMATION: Primer

<400> SEQUENCE: 8
gatcggatcc gaaaaatgtt taactcagct ac                                   32

<210> SEQ ID NO 9
<211> LENGTH: 36
<212> TYPE: DNA
<213> ORGANISM: Artificial Sequence
<220> FEATURE:
<223> OTHER INFORMATION: Primer

<400> SEQUENCE: 9
gatcggatcc ccctttgaag atattctcag gcttcc                               36

<210> SEQ ID NO 10
<211> LENGTH: 34
<212> TYPE: DNA
<213> ORGANISM: Artificial Sequence
<220> FEATURE:
<223> OTHER INFORMATION: Primer

<400> SEQUENCE: 10
gagaatcgat agctcaaacc agcttaggct acac                                 34

<210> SEQ ID NO 11
<211> LENGTH: 32
<212> TYPE: DNA
<213> ORGANISM: Artificial Sequence
<220> FEATURE:
<223> OTHER INFORMATION: Primer

<400> SEQUENCE: 11
gagaatcgat tagaacgtgt ctgggcccca tg                                   32

<210> SEQ ID NO 12
<211> LENGTH: 42
<212> TYPE: DNA
<213> ORGANISM: Artificial Sequence
<220> FEATURE:
<223> OTHER INFORMATION: Primer

<400> SEQUENCE: 12

```
gatcaagctt agcgctctgt ggctgcacca tctgtcttca tc                     42
```

```
<210> SEQ ID NO 13
<211> LENGTH: 42
<212> TYPE: DNA
<213> ORGANISM: Artificial Sequence
<220> FEATURE:
<223> OTHER INFORMATION: Primer

<400> SEQUENCE: 13
gatcatcgat gcggccgcct aacactctcc cctgttgaag ct                     42

<210> SEQ ID NO 14
<211> LENGTH: 396
<212> TYPE: DNA
<213> ORGANISM: Homo sapiens
<220> FEATURE:
<223> OTHER INFORMATION: Vkappa coding region for NIP-Ovalbumin specific
      human antibody

<400> SEQUENCE: 14
aagcttccat ggatatgagg gtccccgctc agctcctggg gctcctgcta ctctggctcc    60
gaggtgccag atgtgacatc cagatgaccc agtctccatc ctccctgtct gcatctgtag   120
gagacagagt caccatcact tgccgggcaa gtcagagcat tagcagctat ttaaattggt   180
atcagcagaa accagggaaa gcccctaagc tcctgatcta tgctgcatcc agtttgcaaa   240
gtggggtccc atcaaggttc agtggcagtg gatctgggac agatttcact ctcaccatca   300
gcagtctgca acctgaagat tttgcaactt actactgtca acagagttac agtacccccc   360
ctttcggcca agggaccaag gtggaaatca agcgct                            396

<210> SEQ ID NO 15
<211> LENGTH: 39
<212> TYPE: DNA
<213> ORGANISM: Artificial Sequence
<220> FEATURE:
<223> OTHER INFORMATION: Primer

<400> SEQUENCE: 15
aatactcgag ccatggacag ccttctgatg aagcaaaag                          39

<210> SEQ ID NO 16
<211> LENGTH: 37
<212> TYPE: DNA
<213> ORGANISM: Artificial Sequence
<220> FEATURE:
<223> OTHER INFORMATION: Primer

<400> SEQUENCE: 16
aatactcgag tcaaaatccc aacatacgaa atgcatc                            37

<210> SEQ ID NO 17
<211> LENGTH: 38
<212> TYPE: DNA
<213> ORGANISM: Artificial Sequence
<220> FEATURE:
<223> OTHER INFORMATION: Primer

<400> SEQUENCE: 17
cgcaagcttc catggtgagc aagggcgagg agctgttc                           38

<210> SEQ ID NO 18
<211> LENGTH: 37
<212> TYPE: DNA
```

<213> ORGANISM: Artificial Sequence
<220> FEATURE:
<223> OTHER INFORMATION: Primer

<400> SEQUENCE: 18
tagagcgctc ttgtacagct cgtccatgcc gagagtg                          37

<210> SEQ ID NO 19
<211> LENGTH: 45
<212> TYPE: DNA
<213> ORGANISM: Artificial Sequence
<220> FEATURE:
<223> OTHER INFORMATION: Primer

<400> SEQUENCE: 19
atttggatcc caccatggag tttgggctga gctgggtttt cctcg                 45

<210> SEQ ID NO 20
<211> LENGTH: 40
<212> TYPE: DNA
<213> ORGANISM: Artificial Sequence
<220> FEATURE:
<223> OTHER INFORMATION: Primer

<400> SEQUENCE: 20
cccgctagct cctgacagga aacagcctcc atctgcacct                       40

<210> SEQ ID NO 21
<211> LENGTH: 623
<212> TYPE: DNA
<213> ORGANISM: Homo sapiens
<220> FEATURE:
<223> OTHER INFORMATION: Genomic DNA fragment

<400> SEQUENCE: 21
atttggatcc caccatggag tttgggctga gctgggtttt cctcgttgct cttttaagag    60
gtgattcatg gagaaataga gagactgagt gtgagtgaac atgagtgaga aaaactggat   120
ttgtgtggca ttttctgata acggtgtcct tctgtttgca ggtgtccagt gtcaggtgca   180
gctggtggag tctggggag gcgtggtcca gcctgggagg tccctgagac tctcctgtgc   240
agcctctgga ttcaccttca gtagctatgc tatgcactgg gtccgccagg ctccaggcaa   300
ggggctagag tgggtggcag ttatatcata tgatggaagt aataaatact acgcagactc   360
cgtgaagggc cgattcacca tctccagaga caattccaag aacacgctgt atctgcaaat   420
gaacagcctg agagctgagg acacggctgt gtattactgt gcgagagaca cagtgagggg   480
aagtcattgt gcgcccagac acaaacctcc ctgcaggaac gctgggggga atcagcggc   540
agggggcgct caggagccac tgatcagagt cagccctgga ggcaggtgca gatggaggct   600
gtttcctgtc aggagctagc ggg                                          623

<210> SEQ ID NO 22
<211> LENGTH: 40
<212> TYPE: DNA
<213> ORGANISM: Artificial Sequence
<220> FEATURE:
<223> OTHER INFORMATION: Primer

<400> SEQUENCE: 22
ggagctagcg ggctgccagt cctcacccca cacctaaggt                       40

<210> SEQ ID NO 23
<211> LENGTH: 40
<212> TYPE: DNA

```
<213> ORGANISM: Artificial Sequence
<220> FEATURE:
<223> OTHER INFORMATION: Primer

<400> SEQUENCE: 23
gggctcgagt cctcaccatc caatggggac actgtggagc                          40

<210> SEQ ID NO 24
<211> LENGTH: 336
<212> TYPE: DNA
<213> ORGANISM: Homo sapiens
<220> FEATURE:
<223> OTHER INFORMATION: Genomic DNA fragment

<400> SEQUENCE: 24
ggagctagcg ggctgccagt cctcacccca cacctaaggt gagccacagc cgccagagcc    60
tccacaggag accccaccca gcagcccagc ccctacccag gaggcccccag agctcagggc  120 gcctgggtgg attctgaaca gccccgagtc acggtgggta tagtgggagc tactaccact   180
gtgagaaaag ctatgtccaa aactgtctcc cggccactgc tggaggccca gccagagaag   240
ggaccagccg cccgaacata cgaccttccc agacctcatg accccagca cttggagctc    300 cacagtgtcc ccattggatg gtgaggactc gagccc                             336

<210> SEQ ID NO 25
<211> LENGTH: 40
<212> TYPE: DNA
<213> ORGANISM: Artificial Sequence
<220> FEATURE:
<223> OTHER INFORMATION: Primer

<400> SEQUENCE: 25
ggagtcgacc cctgcctggg tctcagcccg ggggtctgtg                          40

<210> SEQ ID NO 26
<211> LENGTH: 48
<212> TYPE: DNA
<213> ORGANISM: Artificial Sequence
<220> FEATURE:
<223> OTHER INFORMATION: Primer

<400> SEQUENCE: 26
tatatctaga atataagctt agccatctta cctgaagaga cggtgacc                 48

<210> SEQ ID NO 27
<211> LENGTH: 239
<212> TYPE: DNA
<213> ORGANISM: Homo sapiens
<220> FEATURE:
<223> OTHER INFORMATION: Genomic DNA fragment

<400> SEQUENCE: 27
ggagtcgacc cctgcctggg tctcagcccg ggggtctgtg tggctgggga cagggacgcc    60
ggctgcctct gctctgtgct tgggccatgt gacccattcg agtgtcctgc acgggcacag   120
gtttgtgtct gggcaggaac agggactgtg tccctgtgtg atgcttttga tatctggggc   180
caagggacaa tggtcaccgt ctcttcaggt aagatggcta agcttatatt ctagatata    239

<210> SEQ ID NO 28
<211> LENGTH: 1875
<212> TYPE: DNA
<213> ORGANISM: Homo sapiens
<220> FEATURE:
<223> OTHER INFORMATION: Coding region for a human uH chain
```

<400> SEQUENCE: 28

```
agatctacca tggagtttgg gctgagctgg gttttccttg ttgcgatttt agaaggtgtc      60
cagtgtgagg tgcagctggt ggagtctggg ggaggcttgg tacagcccgg caggtccctg    120
agactctcct gtgcggcctc tggattcacc tttgatgatt atgccatgca ctgggtccgg    180
caagctccag ggaagggcct ggaatgggtc tcagctatca cttggaatag tggtcacata    240
gactatgcgg actctgtgga gggccgattc accatctcca gagacaacgc caagaactcc    300
ctgtatctgc aaatgaacag tctgagagct gaggatacgg ccgtatatta ctgtgcgaaa    360
gtctcgtacc ttagcaccgc gtcctcccct gactattggg gccaaggtac cctggtcacc    420
gtctcgagcg ctagtgcatc cgccccaacc cttttccccc tcgtctcctg tgagaattcc    480
ccgtcggata cgagcagcgt ggccgttggc tgcctcgcac aggacttcct tcccgactcc    540
atcactttct cctggaaata caagaacaac tctgacatca gcagcacccg ggcttccca     600
tcagtcctga gaggggcaa gtacgcagcc acctcacagg tgctgctgcc ttccaaggac    660
gtcatgcagg gcacagacga acacgtggtg tgcaaagtcc agcaccccaa cggcaacaaa    720
gaaaagaacg tgcctcttcc agtgattgcc gagctgcctc ccaaagtgag cgtcttcgtc    780
ccacccccgcg acggcttctt cggcaaccc cgcaagtcca agctcatctg ccaggccacg    840
ggtttcagtc cccggcagat tcaggtgtcc tggctgcgcg aggggaagca ggtgggtct    900
ggcgtcacca cggaccaggt gcaggctgag gccaagagt ctgggcccac gacctacaag    960
gtgaccagca cactgaccat caaagagagc gactggctca gccagagcat gttcacctgc    1020
cgcgtggatc acagggggcct gaccttccag cagaatgcgt cctccatgtg tgtccccgat    1080
caagacacag ccatccgggt cttcgccatc cccccatcct tgccagcat cttcctcacc    1140
aagtccacca agttgacctg cctggtcaca gacctgacca cctatgacag cgtgaccatc    1200
tcctggaccc gccagaatgg cgaagctgtg aaaaccccaca ccaacatctc cgagagccac    1260
cccaatgcca ctttcagcgc cgtgggtgag gccagcatct gcgaggatga ctggaattcc    1320
ggggagaggt tcacgtgcac cgtgacccac acagacctgc cctcgccact gaagcagacc    1380
atctcccggc caaggggggt ggccctgcac aggcccgatg tctacttgct gccaccagcc    1440
cgggagcagc tgaacctgcg ggagtcggcc accatcacgt gcctggtgac gggcttctct    1500
cccgcggacg tcttcgtgca gtggatgcag agggggcagc ccttgtcccc ggagaagtat    1560
gtgaccagcg ccccaatgcc tgagccccag gccccaggcc ggtacttcgc ccacagcatc    1620
ctgaccgtgt ccgaagagga atggaacacg ggggagacct acacctgcgt ggtggcccat    1680
gaggccctgc caacagggt caccgagagg accgtggaca agtccaccga ggggggagtg    1740
agcgccgacg aggagggctt tgagaacctg tgggccaccg cctccacctt catcgtcctc    1800
ttcctcctga gcctcttcta cagtaccacc gtcaccttgt tcaaggtgaa atgagcggcc    1860
gctttacgcg ttaac                                                     1875
```

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29

```
gaagatctca ccatggagtt tg                                               22
```

<210> SEQ ID NO 30

```
<211> LENGTH: 22
<212> TYPE: DNA
<213> ORGANISM: Artificial Sequence
<220> FEATURE:
<223> OTHER INFORMATION: Primer

<400> SEQUENCE: 30
atcttacctc tcgagacggt ga                                              22

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
ccttgaacct cctcgttcga ccc                                             23

<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32
aggcacaaca gaggcagttc cag                                             23

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
cggttcgggg aagtagtcct tgac                                            24

<210> SEQ ID NO 34
<211> LENGTH: 18
<212> TYPE: DNA
<213> ORGANISM: Unknown
<220> FEATURE:
<223> OTHER INFORMATION: Description of Unknown: EGFP oligonucleotide
<220> FEATURE:
<221> NAME/KEY: CDS
<222> LOCATION: (1)..(18)

<400> SEQUENCE: 34 ggc aac tac aag acc cgc                                               18
Gly Asn Tyr Lys Thr Arg
1               5

<210> SEQ ID NO 35
<211> LENGTH: 6
<212> TYPE: PRT
<213> ORGANISM: Unknown
<220> FEATURE:
<223> OTHER INFORMATION: Description of Unknown: EGFP peptide

<400> SEQUENCE: 35

Gly Asn Tyr Lys Thr Arg
1               5

<210> SEQ ID NO 36
<211> LENGTH: 717
<212> TYPE: DNA
```

<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(318)
<220> FEATURE:
<221> NAME/KEY: CDS
<222> LOCATION: (322)..(717)

<400> SEQUENCE: 36

```
atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
50                  55                  60 ctg acc tac ggc gtg cag tgc ttc agc cgc tac ccc gac cac atg aag     240
Leu Thr Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                85                  90                  95 cgc acc atc ttc ttc aag gac gac ggc aac tag tat acc cgc gcc gag     336
Arg Thr Ile Phe Phe Lys Asp Asp Gly Asn     Tyr Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac     480
Asn Tyr Asn Ser His Asn Val Tyr Ile Met Ala Asp Lys Gln Lys Asn
145                 150                 155 ggc atc aag gtg aac ttc aag atc cgc cac aac atc gag gac ggc agc     528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc     576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg     624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc     672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag         717
Val Thr Ala Ala Gly Ile Thr Leu Gly Met Asp Glu Leu Tyr Lys
        225                 230                 235
```

<210> SEQ ID NO 37
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

Met Val Ser Lys Gly Glu Glu Leu Phe Thr Gly Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn
            100                 105

<210> SEQ ID NO 38
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Tyr Thr Arg Ala Glu Val Lys Phe Glu Gly Asp Thr Leu Val Asn Arg
1               5                   10                  15

Ile Glu Leu Lys Gly Ile Asp Phe Lys Glu Asp Gly Asn Ile Leu Gly
            20                  25                  30

His Lys Leu Glu Tyr Asn Tyr Asn Ser His Asn Val Tyr Ile Met Ala
        35                  40                  45

Asp Lys Gln Lys Asn Gly Ile Lys Val Asn Phe Lys Ile Arg His Asn
    50                  55                  60

Ile Glu Asp Gly Ser Val Gln Leu Ala Asp His Tyr Gln Gln Asn Thr
65                  70                  75                  80

Pro Ile Gly Asp Gly Pro Val Leu Leu Pro Asp Asn His Tyr Leu Ser
                85                  90                  95

Thr Gln Ser Ala Leu Ser Lys Asp Pro Asn Glu Lys Arg Asp His Met
            100                 105                 110

Val Leu Leu Glu Phe Val Thr Ala Ala Gly Ile Thr Leu Gly Met Asp
        115                 120                 125

Glu Leu Tyr Lys
    130

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(15)

<400> SEQUENCE: 39 tat tac tgt gcg aaa ga                                        17
Tyr Tyr Cys Ala Lys
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Tyr Tyr Cys Ala Lys
1               5

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggtatagtgg gagctactac                                              20

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (2)..(19)

<400> SEQUENCE: 42 t gat gct ttt gat atc tgg                                          19
  Asp Ala Phe Asp Ile Trp
  1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Ala Phe Asp Ile Trp
1               5

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(21)

<400> SEQUENCE: 44 tat tac tgt gcg aaa gat caa                                        21
Tyr Tyr Cys Ala Lys Asp Gln
1               5

<210> SEQ ID NO 45

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Tyr Tyr Cys Ala Lys Asp Gln
1               5

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(27)

<400> SEQUENCE: 46 tgg gag ctt gat gct ttt gat atc tgg                                27
Trp Glu Leu Asp Ala Phe Asp Ile Trp
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Trp Glu Leu Asp Ala Phe Asp Ile Trp
1               5
```